United States Patent
Kingston et al.

(10) Patent No.: US 8,558,019 B2
(45) Date of Patent: Oct. 15, 2013

(54) THIOLATED PACLITAXELS FOR REACTION WITH GOLD NANOPARTICLES AS DRUG DELIVERY AGENTS

(75) Inventors: David G. I. Kingston, Blacksburg, VA (US); Shugeng Cao, Waltham, MA (US); Jielu Zhao, Blacksburg, VA (US); Glullo F. Paciotti, Ellicott City, MD (US); Marja S. Hubta, Seattle, WA (US)

(73) Assignees: Virginia Tech Intellectual Properties, Inc., Blacksburg, VA (US); Cytimmune Sciences, Inc., Rockville, MD (US)

( * ) Notice: Subject to any disclaimer, the term of this patent is extended or adjusted under 35 U.S.C. 154(b) by 0 days.

(21) Appl. No.: 12/373,135

(22) PCT Filed: Nov. 10, 2008

(86) PCT No.: PCT/US2008/082956
§ 371 (c)(1),
(2), (4) Date: Aug. 27, 2010

(87) PCT Pub. No.: WO2009/062138
PCT Pub. Date: May 14, 2009

(65) Prior Publication Data
US 2011/0144163 A1    Jun. 16, 2011

Related U.S. Application Data

(60) Provisional application No. 60/986,527, filed on Nov. 8, 2007, provisional application No. 61/054,504, filed on May 20, 2008.

(51) Int. Cl.
*C07D 305/14* (2006.01)

(52) U.S. Cl.
USPC .......................................... 549/511

(58) Field of Classification Search
USPC .......................................... 514/468; 549/511
See application file for complete search history.

(56) References Cited

U.S. PATENT DOCUMENTS

| | | | |
|---|---|---|---|
| 6,593,292 B1 | 7/2003 | Rothbard et al. | |
| 6,821,529 B2 | 11/2004 | Nelson | |
| 2005/0085513 A1 | 4/2005 | Baloglu | |
| 2006/0222595 A1 | 10/2006 | Mukherjee | |
| 2008/0063724 A1* | 3/2008 | Desai et al. | 424/491 |
| 2009/0203889 A1* | 8/2009 | Vlahov et al. | 536/6.4 |

OTHER PUBLICATIONS

Paciotti, Colloidal Gold Nanoparticles: A Versatile Platform for Developing Tumor Targeted Cancer Therapies, May 8-12, 2005, NSTI Nanatech 2005, NSTI Nanotechnology Converence and Trade Show, vol. 1, p. 7-10.*
Paciotti, CA Plus Abstract No. 144:260320, 2005.*

* cited by examiner

*Primary Examiner* — Wu-Cheng Winston Shen
*Assistant Examiner* — Karen Cheng
(74) *Attorney, Agent, or Firm* — Whitham Curtis Christofferson & Cook, PC

(57) ABSTRACT

Thioloated taxane derivatives are linked to colloidal metal particles such as gold nanoparticles for use as antitumor agents. The antitumor agents may be targeted to tumors.

5 Claims, 17 Drawing Sheets

Figure 9 A-C

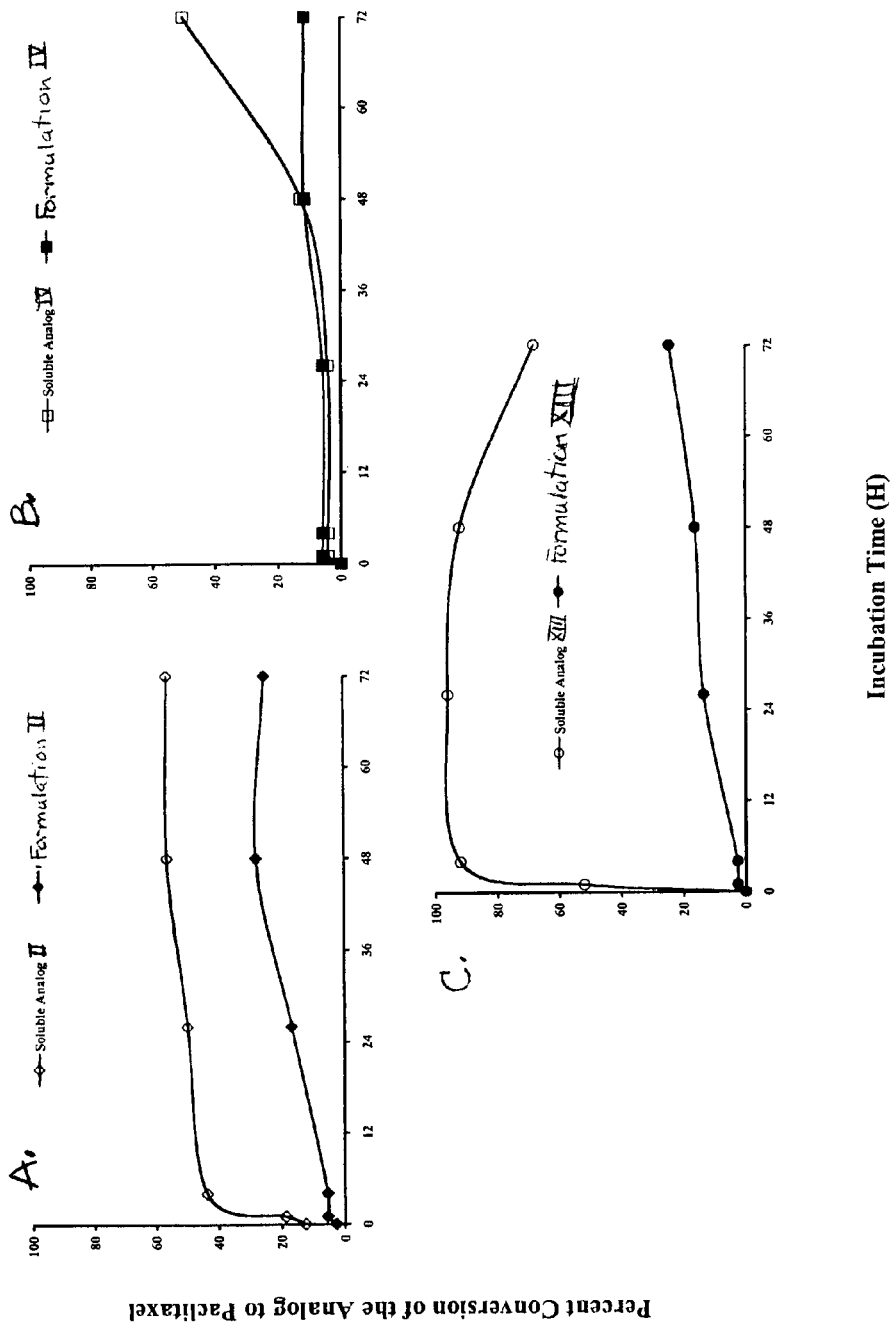
Figure 11 A-C

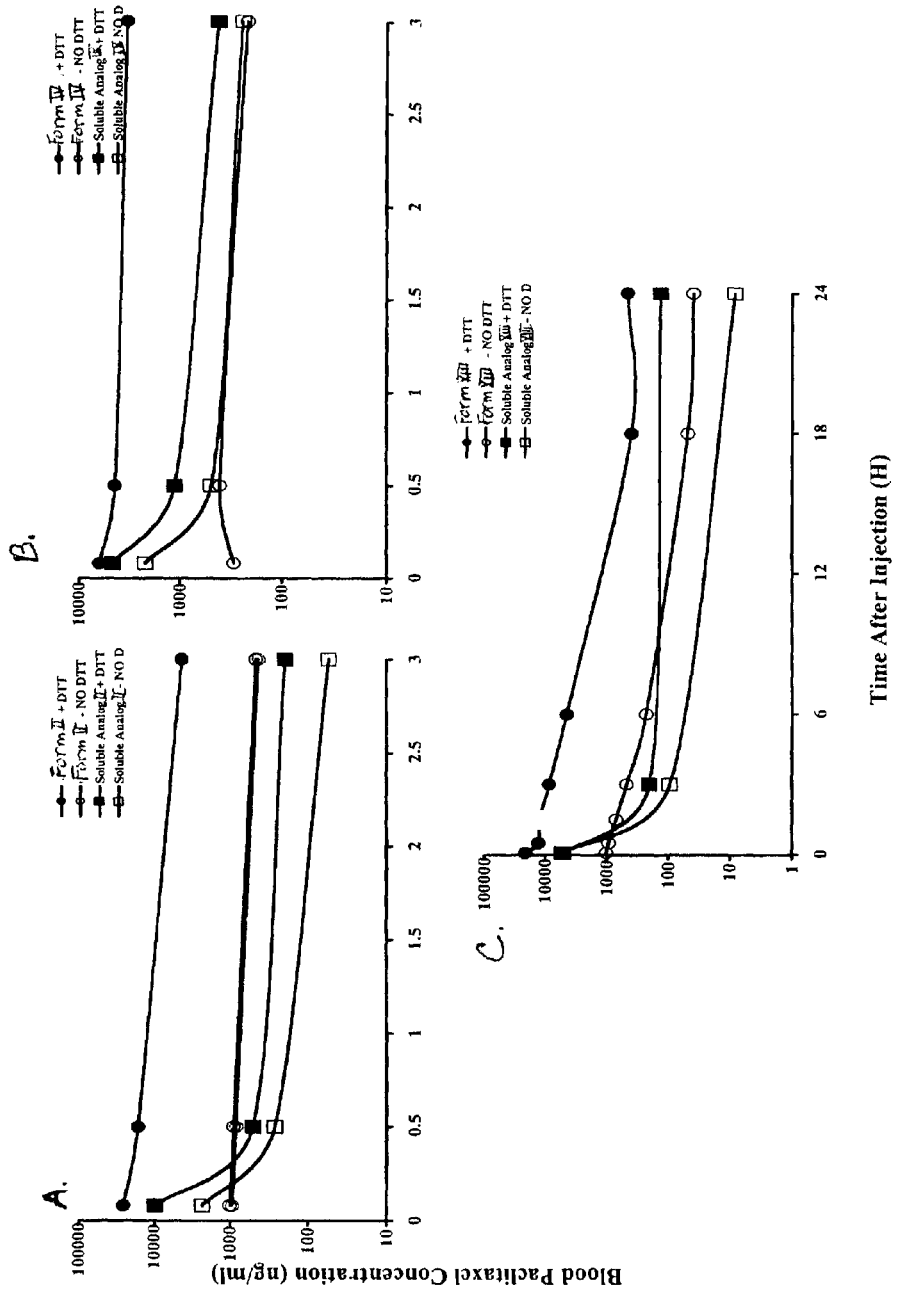
Figure 14A-C

THIOLATED PACLITAXELS FOR REACTION WITH GOLD NANOPARTICLES AS DRUG DELIVERY AGENTS

CROSS-REFERENCE TO RELATED APPLICATIONS

This application claims benefit of United States provisional patent applications 60/986,527 (filed Nov. 8, 2007) and US provisional patent application 61/054,504 (filed May 20, 2008) and International patent application PCT/US2008/082956 filed Nov. 10, 2008, the complete contents of each of which is hereby incorporated by reference.

BACKGROUND OF THE INVENTION

1. Field of the Invention

The present invention concerns antitumor compounds. More particularly, the invention provides novel thiolated taxane derivatives which are preferably linked to colloidial metal particles, such as gold nanoparticles, and used as antitumor agents, and which can be linked to gold nanoparticles to provide stable, extended delivery targeted drug compositions.

2. Background of the Invention

Cancer chemotherapy today still depends largely on cytotoxic agents that kill cancer cells by mechanisms such as disruption of the mitotic spindle or interacting with DNA. These therapies are effective in many cases, and have resulted in decreased cancer mortality, but they suffer from the major defect that they are relatively non-selective, and affect normal cells to some extent as well exerting their desired effect on cancer cells. The deleterious effects of the non-selectivity of these agents, such as paclitaxel, doxorubicin, vinblastine, bleomycin, and many other agents, could largely be abrogated if the drugs could be targeted directly to the tumor.

One of the most effective current clinical agents is Paclitaxel (Taxol™) a depiction of which is presented in FIG. 1. This compound is a natural product extracted from the bark of Pacific yew trees, *Taxus brevifolia*. It has been shown to have excellent antitumor activity in in vivo animal models, and studies have elucidated its unique mode of action, which involves abnormal polymerization of tubulin and disruption of mitosis (Schiff, P B, Fant, J, Horwitz, S B. "Promotion of microtubule assembly in vitro by taxol." Nature 1979 277:665-667). Paclitaxel has been approved for the treatment of ovarian and breast cancers, as well as Kaposi's sarcoma; and studies involving colon, and lung cancers have shown promising results. The results of paclitaxel clinical studies are reviewed in Nowak, A. K.; Wilcken, N. R. C.; Stockler, M. R.; Hamilton, A.; Ghersi, D. Systematic review of taxane-containing versus non-taxane-containing regimens for adjuvant and neoadjuvant treatment of early breast cancer. *The Lancet* 2004, 5, 372-830; in Crown, J.; O'Leary, M.; Ooi, W.-S. Docetaxel and paclitaxel in the treatment of breast cancer: A review of clinical experience. *The Oncologist* 2004, 9, 24-32; and in Brown, D. T., Preclinical and clinical studies of the taxanes. In Taxus: The genus *Taxus*, Itokawa, H., Lee, K. H., Eds.; Taylor and Francis: London, 2003; Vol. pp 387-435.

Various methods have been developed for the targeting of paclitaxel to tumors. These include the use of antibodies (Ojima, I. Guided Molecular Missiles for Tumor-Targeting Chemotherapy-Case Studies Using the Second-Generation Taxoids as Warheads. Acc Chem Res 2007), the use of peptides (Kumar, S K, Williams, S A, Isaacs, J T, Denmeade, S R, Khan, S R. Modulating paclitaxel bioavailability for targeting prostate cancer. Bioorg & Med Chem 2007 15:4973-4984), and the use of folic acid (Lee, J W, Lu, J Y, Low, P S, Fuchs, P L. Synthesis and Evaluation of Taxol-Folic Acid Conjugates as Targeted Antineoplastics. Bioorg Med Chem 2002 10:2397-2414) and the use of DHA (Bradley, M O, Swindell, C S, Anthony, F H, Witman, P A, Devanesan, P, Webb, N L, Baker, S D, Wolff, A C, Donehower, R C. Tumor Targeting by Conjugation of DHA to Paclitaxel. J Controlled Release 2001 74(1-3):233-236). The subject of improved drug delivery methods for paclitaxel has been discussed in a recent review (Ganesh, T. Improved biochemical strategies for targeted delivery of taxoids. Bioorg & Med Chem 2007 15:3597-3623), and prodrug strategies for paclitaxel delivery have also been reviewed (Skwarczynski, M, Hayashi, Y, Kiso, Y. Paclitaxel Prodrugs: Toward Smarter Delivery of Anticancer Agents. J Med Chem 2006 49:7253-7269).

The combination of gold nanoparticles with tumor necrosis factor (TNFα) targets the nanoparticles to tumors and provides a therapeutic effect. This effect is enhanced when paclitaxel is also linked to the nanoparticles (Paciotti, G F, Kingston, D G I, Tamarkin, L. Colloidal Gold Nanoparticles: A Novel Nanoparticle Platform for Developing Multifunctional Tumor-targeted Drug Delivery Vectors. Drug Devel Res 2006 67:47-54). Unfortunately, the currently available paclitaxel derivatives do not give the full therapeutic effect that is desired. It would therefore be beneficial to develop paclitaxel derivatives which have the desired properties for combining with gold nanoparticles, and which also exhibit the full desired therapeutic effect.

SUMMARY OF THE INVENTION

The invention is based on the development of novel paclitaxel derivatives. These derivatives can be delivered using colloidal metal particles such as gold nanoparticles. Importantly, the activity of the derivatives is not abrogated by attachment to gold, so that the impact of the paclitaxel on the targeted cells or tissue (e.g. tumor cells) is the same as or comparable to that of paclitaxel delivered by traditional methods. The novel compounds each contain a sulfur moiety that mediates attachment of the compound to a metallic nanoparticle, especially to gold nanoparticles. The invention thus also provides metallic nanoparticle-paclitaxel derivative complexes (i.e. metal nanoparticles to which at least one paclitaxel derivative is attached or bonded) and therapeutic compositions of such complexes.

It is an object of this invention to provide paclitaxel derivatives containing a thiol or a derivatized thiol group connected to paclitaxel by a variable linker, and suitable for binding to gold nanoparticles.

The invention provides compounds of formula 1

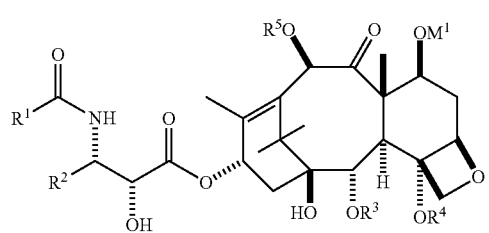

Wherein: $R^1$ is phenyl, tert-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$ where $R^x$ is: H;

$C_{1-6}$ alkyl, optionally substituted with one to six halogen atoms, which may be the same or different; $C_{3-6}$ cycloalkyl; or $C_{2-6}$ alkenyl or hydroxyl; $R^5$ is H; or methyl; or $C(O)R^x$, where $R^x$ is: H, $C_{1-6}$ alkyl, optionally substituted with one to six halogen atoms, which may be the same or different; $C_{3-6}$ cycloalkyl; $C_{2-6}$ alkenyl or hydroxyl; and M1 is a sulphur-bearing substituent as described herein.

The invention further provides compounds of formula 22

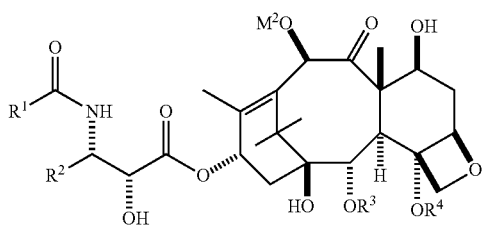

22 wherein: $R^1$ is phenyl, tert-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$ where $R^x$ is: H; $C_{1-6}$ alkyl, optionally substituted with one to six halogen atoms, which may be the same or different; $C_{3-6}$ cycloalkyl; or $C_{2-6}$ alkenyl or hydroxyl; where $R^x$ is: H, $C_{1-6}$ alkyl, optionally substituted with one to six halogen atoms, which may be the same or different; $C_{3-6}$ cycloalkyl; $C_{2-6}$ alkenyl or hydroxyl; and $M^2$ is a sulphur-bearing substituent as described herein.

The invention further provides compounds of formula 43

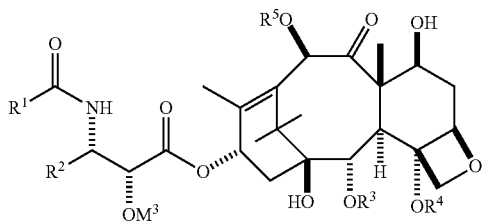

43 wherein: $R^1$ is phenyl, tert-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$ where $R^x$ is: H; $C_{1-6}$ alkyl, optionally substituted with one to six halogen atoms, which may be the same or different; $C_{3-6}$ cycloalkyl; or $C_{2-6}$ alkenyl or hydroxyl; $R^5$ is H; or methyl; or $C(O)R^x$, where $R^x$ is: H, $C_{1-6}$ alkyl, optionally substituted with one to six halogen atoms, which may be the same or different; $C_{3-6}$ cycloalkyl; $C_{2-6}$ alkenyl or hydroxyl; and $M^3$ is a sulphur-bearing substituent as described herein.

The invention also provides methods of treating cancer using compounds 1, 22 and 43.

In other embodiments, the invention provides a composition comprising: a paclitaxel derivative comprising at least one sulfur atom; and a colloidal metal particle. In this embodiment, the paclitaxel derivative is bound to the colloidal metal particle through the at least one sulfur atom. In vivo, the composition acts as a depot for the slow release of paclitaxel. The colloidal metal particle comprises gold, silver, aluminum, ruthenium, zinc, iron, nickel and calcium lithium, sodium, magnesium, potassium, scandium, titanium, vanadium, chromium, manganese, cobalt, copper, gallium, strontium, niobium, molybdenum, palladium, indium, tin, tungsten, rhenium, platinum, or gadolinium. In one embodiment, the colloidal metal particle comprises a gold nanoparticle.

In yet other embodiments, the invention provides an anticancer agent comprising: a paclitaxel derivative comprising at least one sulfur atom; and a colloidal metal particle. In this embodiment, the paclitaxel derivative is bound to the colloidal metal particle through the at least one sulfur atom, and the anticancer agent is stable under physiological conditions. The colloidal metal particle comprises gold, silver, aluminum, ruthenium, zinc, iron, nickel and calcium lithium, sodium, magnesium, potassium, scandium, titanium, vanadium, chromium, manganese, cobalt, copper, gallium, strontium, niobium, molybdenum, palladium, indium, tin, tungsten, rhenium, platinum, or gadolinium. In one embodiment, the colloidal metal particle comprises a gold nanoparticle.

The invention also provides a composition comprising a colloidal metal particle, an integrating molecule, and a therapeutic agent. The therapeutic agent comprises the compound of formula 1

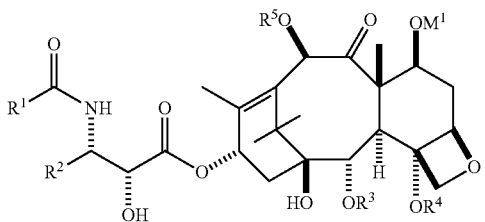

1

Wherein: $R^1$ is phenyl, tert-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$ where $R^x$ is: H; $C_{1-6}$ alkyl, optionally substituted with one to six halogen atoms, which may be the same or different; $C_{3-6}$ cycloalkyl; or $C_{2-6}$ alkenyl or hydroxyl; $R^5$ is H; or methyl; or $C(O)R^x$, where $R^x$ is: H, $C_{1-6}$ alkyl, optionally substituted with one to six halogen atoms, which may be the same or different; $C_{3-6}$ cycloalkyl; $C_{2-6}$ alkenyl or hydroxyl; and M1 is a sulphur-bearing substituent. In this embodiment, the colloidal metal particle comprises gold, silver, aluminum, ruthenium, zinc, iron, nickel and calcium lithium, sodium, magnesium, potassium, scandium, titanium, vanadium, chromium, manganese, cobalt, copper, gallium, strontium, niobium, molybdenum, palladium, indium, tin, tungsten, rhenium, platinum, or gadolinium. The colloidal metal particle may further comprise polyethylene glycol, PolyPEG®, polyoxypropylene polymers, polyvinylpyrrolidone polymers, rPEG, or hydroxyethyl starch; and may comprise a gold nanoparticle. In some embodiments, the gold nanoparticle is pegylated. In some embodiments, the integrating molecule comprises tumor necrosis factor, interleukins, growth factors, hormones, cofactors, enzyme substrates, immunoregulatory molecules, adhesion molecules, vascular markers, neovascular markers, molecular chaperones, or heat shock proteins. In some embodiments, the therapeutic agent comprises:

i) analog 2

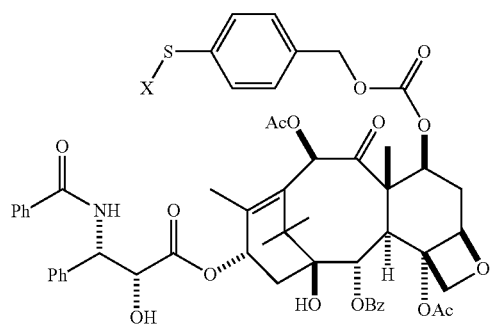

where X represents the colloidal metal particle to which the analog is attached; or
ii) analog 3

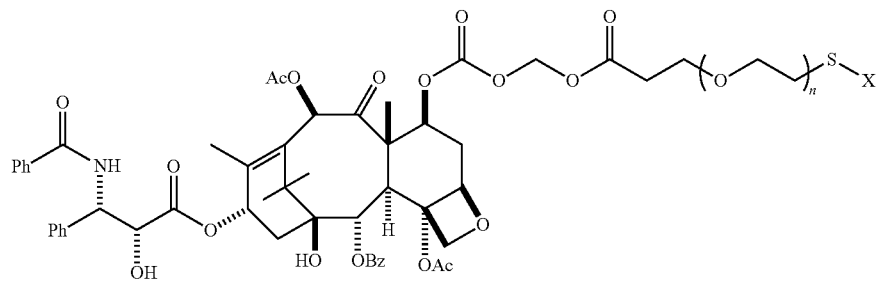

where n=8 and X represents the colloidal metal particle to which the analog is attached; or
iii) analog 16

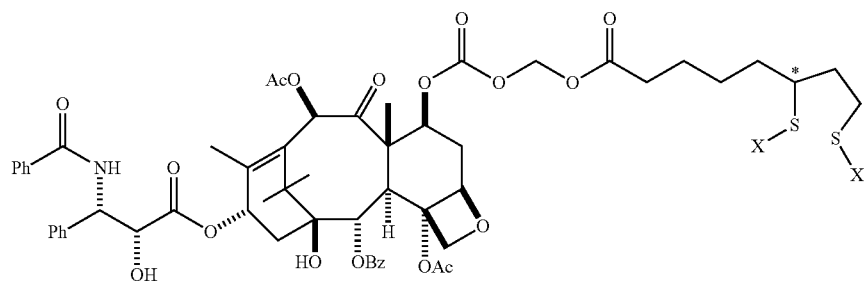

where $R^1$=phenyl and $R^2$=acetyl. Analog 16 is attached to the colloidal metal particle via the S atoms, and X represents the colloidal metal particle to which the analog is attached. Both X's may represent a single metal particle to which both thiols are attached, or the X's may represent two different metal particles, each thiol being attached to one of the two different metal particles, each of which is represented by X.

The invention further provides a composition comprising a colloidal metal particle, an integrating molecule, and a therapeutic agent. The therapeutic agent comprises the compound of formula 43

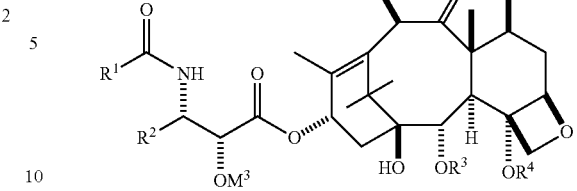

wherein: $R^1$ is phenyl, tert-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$ where $R^x$ is: H; $C_{1-6}$ alkyl, optionally substituted with one to six halogen atoms, which may be the same or different; $C_{3-6}$ cycloalkyl; or $C_{2-6}$ alkenyl or hydroxyl; $R^5$ is H; or methyl; or $C(O)R^x$, where $R^x$ is: H, $C_{1-6}$ alkyl, optionally substituted with one to six halogen atoms, which may be the same or different; $C_{3-6}$ cycloalkyl; $C_{2-6}$ alkenyl or hydroxyl; and M1 is a sulphur-bearing substituent. In some embodiments, the colloidal metal particle comprises gold, silver, aluminum, ruthenium, zinc, iron, nickel and calcium lithium, sodium, magnesium, potassium, scandium, titanium, vanadium, chromium, manganese, cobalt, copper, gallium, strontium, niobium, molybdenum, palladium, indium, tin, tungsten, rhenium, platinum, or gadolinium, and the colloidal metal particle may further comprise polyethylene glycol, PolyPEG®, polyoxypropylene polymers, polyvinylpyrrolidone polymers, rPEG, or hydroxyethyl starch. In some embodiments, the colloidal metal particle comprises a gold nanoparticle. The gold nanoparticle may be pegylated. The integrating molecule of the composition comprises tumor necrosis factor, interleukins, growth factors, hormones, cofactors, enzyme substrates, immunoregulatory molecules, adhesion molecules, vascular markers, neovascular markers, molecular chaperones, or heat shock proteins. In one embodiment, the therapeutic agent comprises i) analog 44,

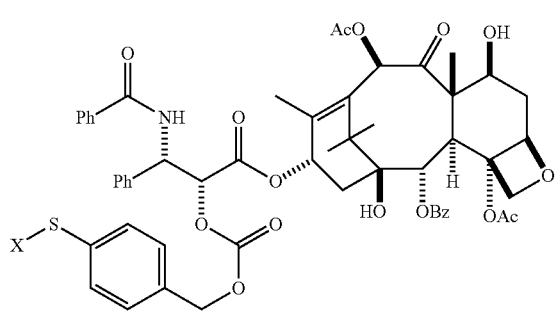

where X represents the colloidal metal particle to which compound 4 is attached (both X's may represent a single metal particle to which both thiols are attached, or the X's may represent two different metal particles, each thiol being attached to one of the two different metal particles, each of which is represented by X); or
ii) analog 54

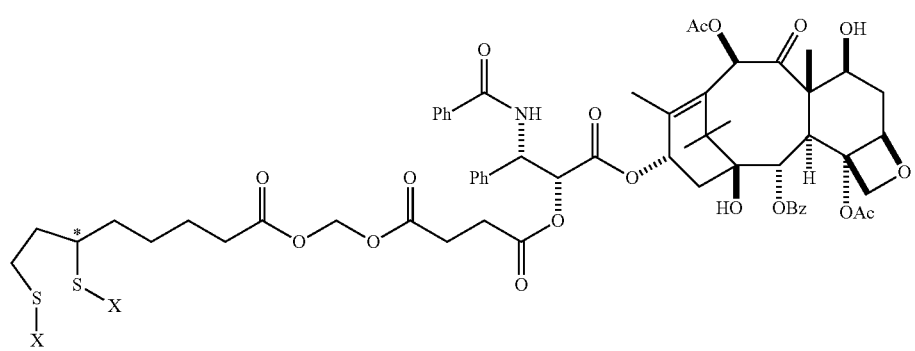

wherein the stereochemistry at the chiral center * is (R/S), (R), or (S); and wherein said analog 54 is attached to the metal particle via the S atoms, where X represents the colloidal metal particle to which the analog is attached (both X's may represent a single metal particle to which both thiols are attached, or the X's may represent two different metal particles, each thiol being attached to one of the two different metal particles, each of which is represented by X.); or
iii) analog 56

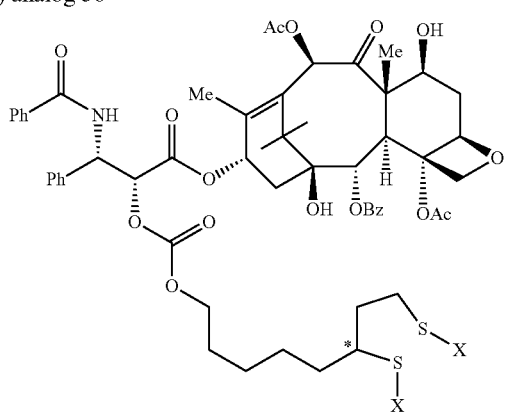

wherein the stereochemistry at the chiral center * is (R/S), (R), or (S); and wherein said analog 56 is attached to the metal particle via the S atoms, where X represents the colloidal metal particle to which the analog is attached; (both X's may represent a single metal particle to which both thiols are attached, or the X's may represent two different metal particles, each thiol being attached to one of the two different metal particles, each of which is represented by X.); or
iv) analog 57

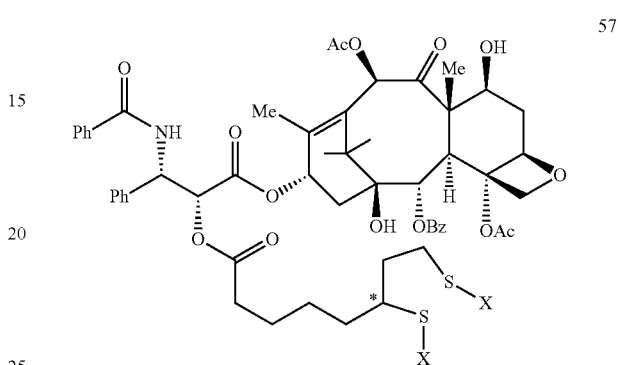

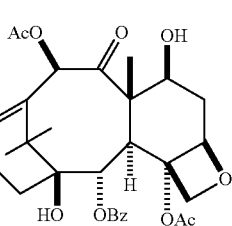

wherein the stereochemistry at the chiral center * is (R/S), (R), or (S); and wherein said analog 57 is attached to the metal particle via the S atoms, where X represents the colloidal metal particle to which the analog is attached (both X's may represent a single metal particle to which both thiols are attached, or the X's may represent two different metal particles, each thiol being attached to one of the two different metal particles, each of which is represented by X).

In yet another embodiment, the invention provides an anti-cancer agent, comprising a paclitaxel derivative comprising at least one sulfur atom; and an antibody, the paclitaxel derivative being bound to the antibody through the at least one sulfur atom.

BRIEF DESCRIPTION OF THE DRAWINGS

FIGS. 11A-C provide graphic representations showing the generation of paclitaxel from the soluble and colloidal gold bound analogs (formulations). A, analog and formulation II; B, analog and formulation IV; C, analog and formulation XIII.

FIGS. 14A-C provide pharmacokinetic data of unformulated soluble paclitaxel analogs or the analog-colloidal gold-based nanodrugs. Two representations for each formulation are shown. Those designated +DTT denotes total paclitaxel in the blood while groups with the No DTT designation represents the fraction of the total analogs that was converted to paclitaxel in the blood. A, analog and formulation II; B, analog and formulation IV; C, analog and formulation XIII.

DETAILED DESCRIPTION

The present invention provides sulphur-containing paclitaxel derivatives which can be attached to metallic nanoparticles, particularly to gold nanoparticles, as a means of delivering fully active paclitaxel to an in vivo site of activity. Attachment of the derivatives to nanoparticles provides a substance which can act as a cancer chemotherapeutic agent either directly, with the paclitaxel still bound to the nanoparticle, or by release of the paclitaxel from the nanoparticle through a chemical or biological conversion reaction. The conversion can occur by a hydrolysis reaction or by some other release mechanism. Since the nanoparticle can access a tumor because of the leaky vasculature associated with solid tumors, while it is less able to access other cell types, the delivery of a fully active form of paclitaxel to a desired site of action is more efficient than when the paclitaxel is delivered by conventional means, (e.g. when the drug is not attached to a nanoparticle). Gold nanoparticles in particular have a surface chemistry particularly suited to the attachment of sulphur-containing molecules, such as thiols, and the compounds of the invention possess at least one sulphur atom capable of attaching to metal particles such as gold. In some embodiments of the invention, the metal nanoparticle-paclitaxel derivative complexes also comprise a targeting element which is selective for a desired targeted cell or tissue type, such as a tumor.

Figure 1:
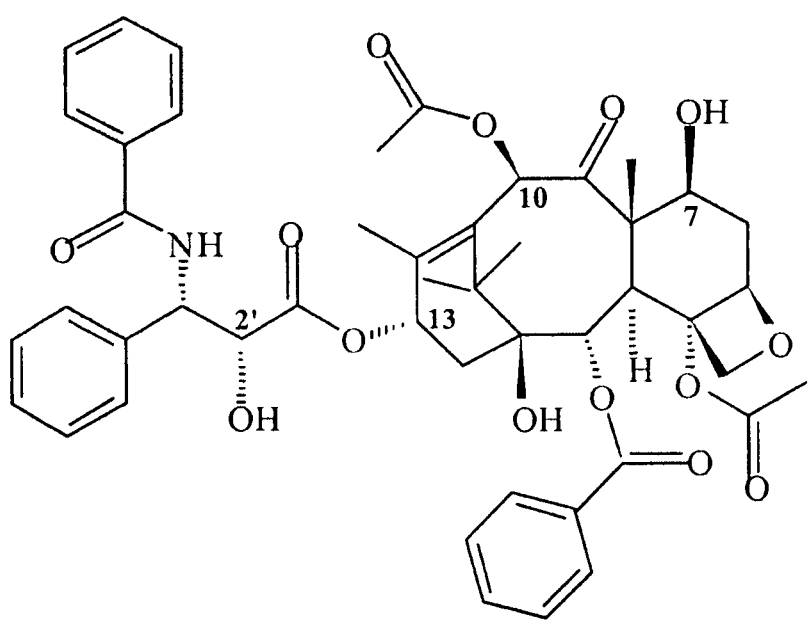
FIG. 1. Paclitaxel, highlighting locations for adding sulfur substituents.
Figure 2:
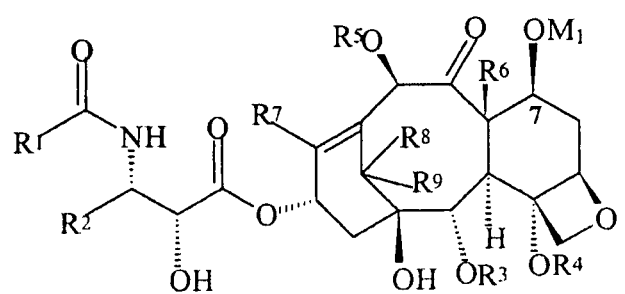
FIG. 2. Generic formula for paclitaxel derivative M1 with a sulfur substituent at C7.
Figure 3:
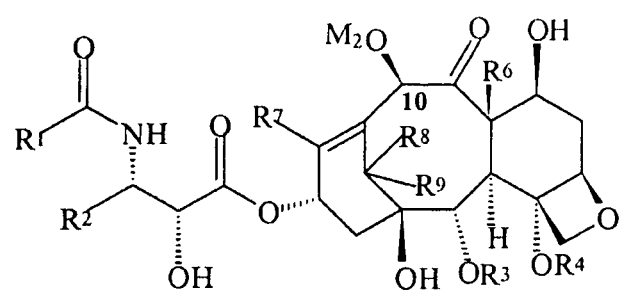
FIG. 3. Generic formula for paclitaxel derivative M2 with a sulfur substituent at C10.
Figure 4:
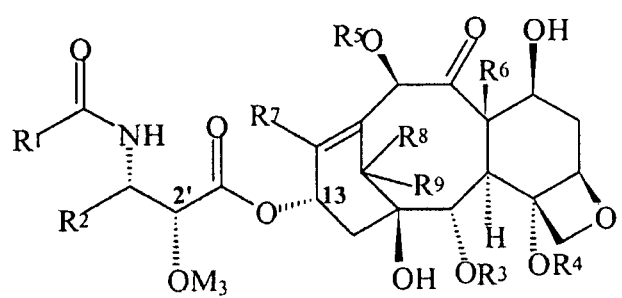
FIG. 4. Generic formula for paclitaxel derivative M3 with a sulfur substituent at C2'.

The paclitaxel derivatives of the invention are generally made by covalently attaching a sulphur-containing moiety to reactive groups located at the C7, C10 or C13 carbons of paclitaxel. In particular: 1) the hydroxyls attached to the C7 carbon of paclitaxel; or 2) the acyl group attached to the C10 carbon; or 3) the C2' of a substituted 3-amion-2-hydroxypropanoyloxy group attached to the C13 carbon, are modified. FIG. 1 depicts a paclitaxel molecule in which the C7, C10, C13 and C2' carbons are indicated. In addition, other substituents of the paclitaxel molecular scaffold may also be modified or substituted, as described in detail below.

C7 Derivatives

Formula MI depicts a generic paclitaxel derivative with a sulphur-containing moiety, $M_1$, attached to oxygen at the C7 carbon.

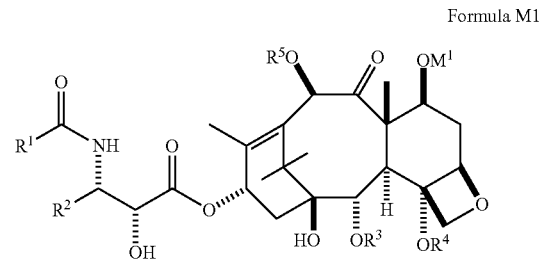

Formula M1

C10 Derivatives

In some embodiments of the invention, the sulphur containing substituent is attached to the oxygen of the C10 carbon of the paclitaxel scaffold, and shown in the following generic formula:

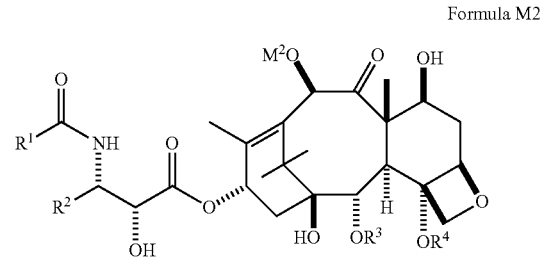

Formula M2

C13 Derivatives

In some embodiments of the invention, the sulphur containing substituent is attached to the oxygen of the C2' carbon of a substituted 3-amino-2-hydroxypropanoyloxy group attached to the $C_{1-3}$ carbon of the paclitaxel scaffold, and shown in the following generic formula:

Formula M3

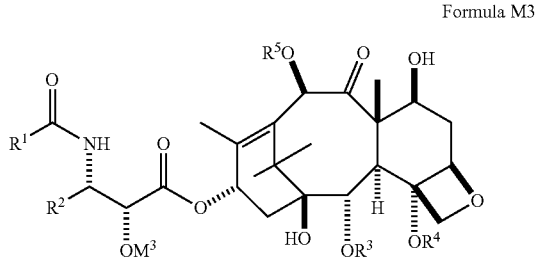

In formulas M1, M2 and M3, $R^1$ is phenyl, tert-butoxy, or $C_{1-6}$ alkyloxy;

$R^2$ is phenyl, 4-fluorophenyl, 4-methylphenyl, 2-furanyl, 2-theinyl, isopropyl, isobutenyl, cyclopropyl, 3-furanyl, 3-thienyl, or 2-propenyl;

$R^3$ is benzoyl, m-methoxybenzoyl, m-azidobenzoyl, or m-chlorobenzoyl;

$R^4$ is $C(O)R^x$ where $R^x$ is: H; $C_{1-6}$ alkyl, optionally substituted with one to six halogen atoms, which may be the same or different; $C_{3-6}$ cycloalkyl; or $C_{2-6}$ alkenyl; or $C_{1-6}$ alkyloxy;

$R^5$ is H; or methyl; or $C(O)R^x$, where $R^x$ is: H, $C_{1-6}$ alkyl, optionally substituted with one to six halogen atoms, which may be the same or different; $C_{3-6}$ cycloalkyl; $C_{2-6}$ alkenyl or hydroxyl;

$M^1$, $M^2$ and $M^3$ are the sulphur-bearing substituents described herein.

$M^1$, $M^2$ and $M^3$ are the varied sulphur-bearing substituents that can be utilized in the present invention. Most substituents can be used at all three substitution positions (i.e. at C7, C10 and C2'), although the effect of such substitution may vary with the position of substitution. For example, those of skill in the art will recognize that the 2' and 7 positions of the paclitaxel "scaffold" have different reactivities. Groups at C2' are more easily converted back to taxol than groups at C7. As a result, paclitaxels bearing simple ester substituents at C2' can be converted to paclitaxel in vivo, while similar substituents at C7 and C10 are not normally converted to paclitaxel under physiological conditions. However, paclitaxels substituted with simple ester groups at C7 and C10 still have value to the present invention, since paclitaxels substituted at these positions retain some or all of the bioactivity of the native drug (Kingston, D G I. Taxol, a Molecule for all Seasons. Chemical Communications 2001 867-880). Substituents at C7 that convert to paclitaxel under physiological conditions include those with the group C7-OCOOCH$_2$OCOYSX, where Y is a variable group (can be (CH$_2$)$_n$, PEG, etc.) and X is a chemical leaving group of interest. As noted above, simple ester groups of various kinds are suitable for use at C2'.

Examples of the sulphur-bearing substituents which are utilized to produce the compounds of the invention are described below as Substituents 1-23. In each case, the "free bond" at the end of each structure that is considered to be the bond through which the substituent is linked to the C7, C10, or C2' hydroxyl group; it does not represent a methyl group. Certain of the substituents contain a chiral center which may be in either the R or the S configuration, and the invention encompasses compounds containing these substitutents as either pure R enantiomers or as pure S enantiomers or as mixtures of R and S enantiomers (R/S).

Substituent 1

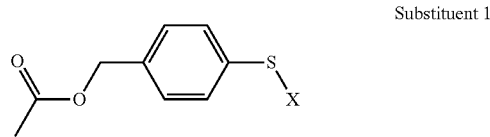

where X is hydrogen; a 2-thiopyridyl group; a halogen; a substituted sulfinate group —SO$_2$R where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl.

Substituent I is preferably incorporated into the compounds of the invention as follows:

M1 (see Example 1, Scheme 1.1 for exemplary synthesis),

M3 (see Example 1, Scheme 1.3 for exemplary synthesis).

Substituent 2

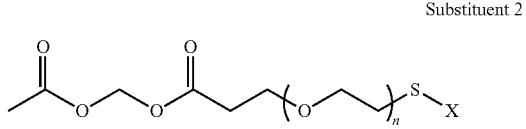

where n=1-50;

where X is hydrogen; a 2-thiopyridyl group; a halogen; a substituted sulfinate group —SO$_2$R where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1$CO, where $R_1$ is $C_{1-6}$ alkyl optionally substituted with one to six halogen atoms that may be the same or different, $C_{3-6}$ cycloalkyl; $C_{2-6}$ alkenyl, or phenyl.

Pegylated Substituent 2 is preferably incorporated into the compounds of the invention as follows:

M1 (see Example 2, Scheme 2.1 for exemplary synthesis);

M2 (see Example 2, Scheme 2.2A for hypothetical exemplary synthesis);

Substituent 3

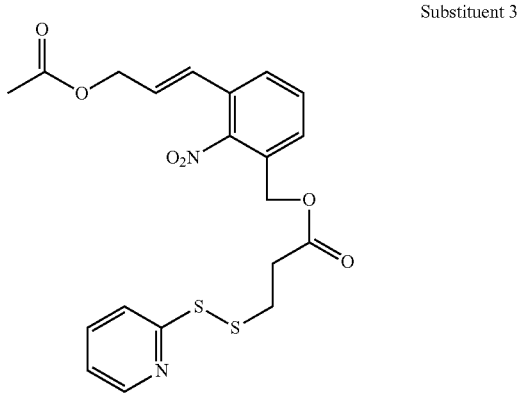 [SMILES: CC(=O)OC/C=C/c1cccc(COC(=O)CCSSc2ccccn2)c1[N+](=O)[O-]]

Substituent 3 is preferably incorporated into the compounds of the invention as follows:

M1 (see Example 3, Scheme 3.1 for exemplary synthesis);
M3 (see Example 3, Scheme 3.3 for exemplary synthesis)

Substituent 4

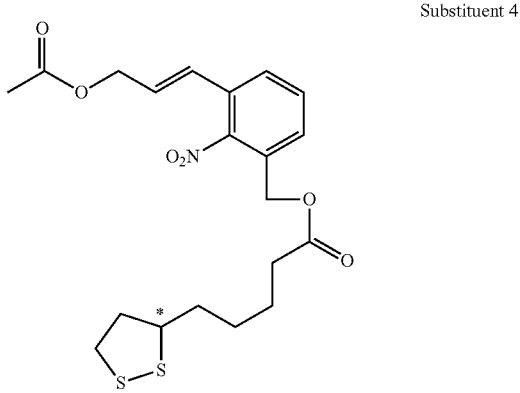 [SMILES: CC(=O)OC/C=C/c1cccc(COC(=O)CCCCC2CCSS2)c1[N+](=O)[O-]]

where * indicates a chiral center which may be in either the R, the S, or the RS configuration.

Substituent 4 is preferably incorporated into the compounds of the invention as follows:

M1 (see exemplary synthesis in Example 4, scheme 4.1);
M3 (see exemplary synthesis in Example 4, scheme 4.3).

In other embodiments, the sulphur-bearing substituent is a polyethylene glycol (PEG) acid.

In addition to Substituent 2 above and Substituents 21-22 below, other exemplary substituents of this type are depicted below:

Substituent 5

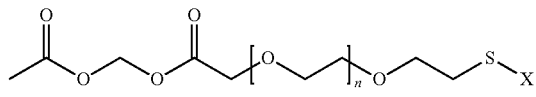

where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl, and where n=1-50.

Substituent 5 is preferably incorporated into the compounds of the invention as follows:

M1 (see exemplary synthesis in Example 5, scheme 5.1);
M2 (see exemplary synthesis in Example 5, scheme 5.2);

Substituent 6

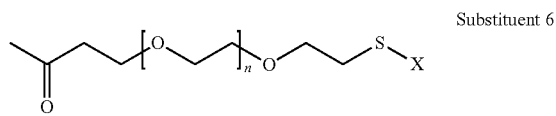

where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl, and where n=0-50. Substituent 7 is preferably incorporated into the compounds of the invention as follows:

M1 (see Example 6, Scheme 6.1, for an exemplary synthesis);
M2 (see Example 6, Scheme 6.2, for an exemplary synthesis);
M3 (see Example 6, Scheme 6.3, for an exemplary synthesis).

Substituent 7

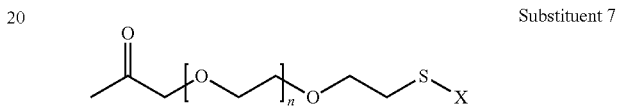

where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl, and where n=1-50.

Substituent 8

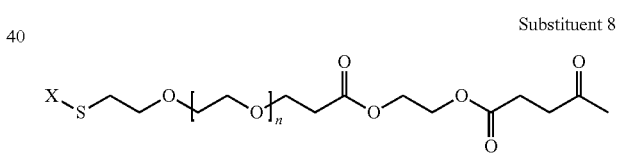

where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl, and where n=0-50, preferably 7

Substituent 8 is preferably incorporated into the compounds of the invention as follows:

M1 (see Example 8.1, Scheme 8.1, for an exemplary synthesis);
M2 (see Example 8.2, Scheme 8.2, for an exemplary synthesis);
M3 (see Example 8.3, Scheme 8.3, for an exemplary synthesis)

Substituent 9

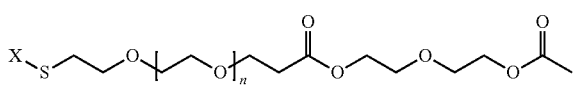

where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl, and where n=0-50, preferably 7.

Substituent 9 is preferably incorporated into the compounds of the invention as follows:

M1 (see Example 9.1, Scheme 9.1 for an exemplary synthesis)

M2 (a modification of Scheme 8.2 will give compounds of the M2 class for substituent 9)

M3 (see Example 9.3, Scheme 9.3 for an exemplary synthesis).

Other possible sulphur-bearing substituents include:

Substituent 10

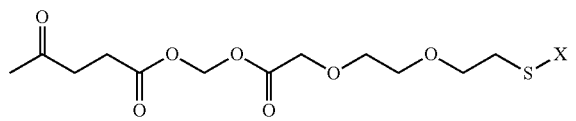

where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl.

Substituent 10 is preferably incorporated into the compounds of the invention as follows: (we have not prepared any compounds of this class; they are hypothetical only)

M1 (see Example 10.1, Scheme 10.1 for an exemplary synthesis).

M3 (see Example 10.3, Scheme 10.3 for an exemplary synthesis).

Substituent 11

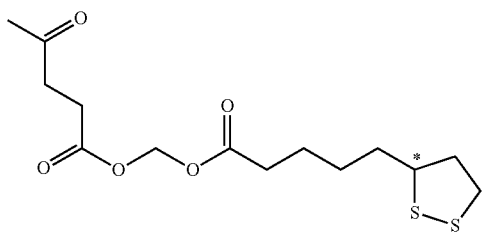

where * indicates a chiral center which may be in either the R, the S, or the RS configuration.

Substituent 11 is preferably incorporated into the compounds of the invention as follows:

M1 (see Example 11.1, Scheme 11.1 for an exemplary synthesis).

M3 (see Example 11.3, Scheme 11.3 for an exemplary synthesis).

Substituent 12

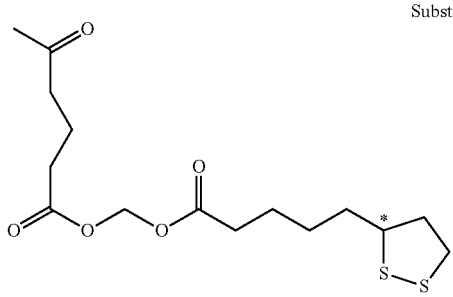

where * indicates a chiral center which may be in either the R, the S, or the RS configuration.

Substituent 12 is preferably incorporated into the compounds of the invention as follows:

M1 (see Example 12.1, Scheme 12.1 for an exemplary synthesis).

M3 (see Example 12.3, Scheme 12.3 for an exemplary synthesis).

Substituent 13

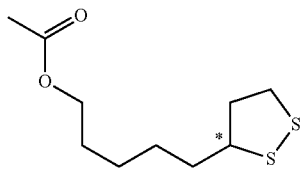

where * indicates a chiral center which may be in either the R, the S, or the RS configuration.

Substituent 13 is preferably incorporated into the compounds of the invention as follows:

M3 (see Example 13.3, Scheme 13.3 for an exemplary synthesis).

Substituent 14

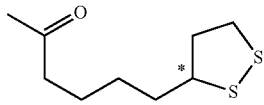

where * indicates a chiral center which may be in either the R, the S, or the RS configuration.

Substituent 14 is preferably incorporated into the compounds of the invention as follows:

M3 (see Example 14.3, Scheme 14.3 for an exemplary synthesis).

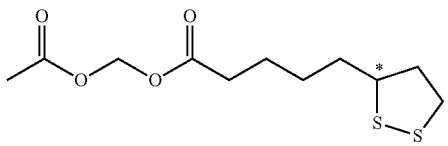

Substituent 15 where * indicates a chiral center which may be in either the R, the S, or the RS configuration.

Substituent 15 is preferably incorporated into the compounds of the invention as follows:

M1 (see Example 15.1, Scheme 15.1 for an exemplary synthesis);

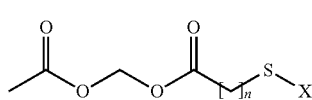

Substituent 16 where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl, and where n=1-10.

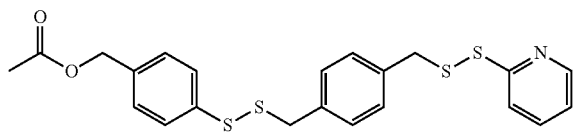

Substituent 17

Substituent 17 is preferably incorporated into the compounds of the invention as follows:

M1 (see Example 17.1, Scheme 17.1 for exemplary synthesis).

M3 (see Example 17.3, Scheme 17.3 for exemplary synthesis).

Compounds that are Dimers

In some embodiments of the invention, the sulphur-bearing substituent terminates in reactive terminal sulfur and can thereby be linked to another derivative that also bears a reactive terminal sulfur, forming a dimer. The derivative may, for example, be a PEGylated paclitaxel that links to another PEGylated paclitaxel to form the dimer. In some embodiments, the derivatives that are linked are identical, so that a symmetrical dimer is formed, although this need not always be the case (non-symmetrical dimers may occur). Examples of sulphur-bearing substituents suitable for use in this aspect of the invention include those that follow, in which the parentheses indicate the terminal sulphur bond through which the dimer is formed. In other words, the substituent unit: X—S—)$_2$ (where X represents the atoms of the substituent chain other than sulphur), forms a dimer with another substituent unit, in which the two sulphur atoms are bonded: X—S—S—X.

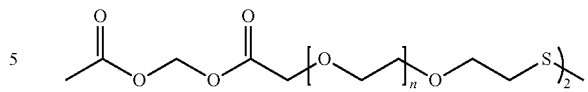

Substituent 17 where n ranges from 1-50.

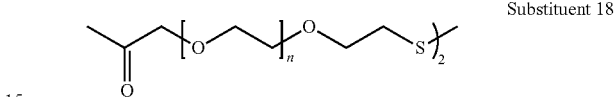

Substituent 18 where n ranges from 0-50.

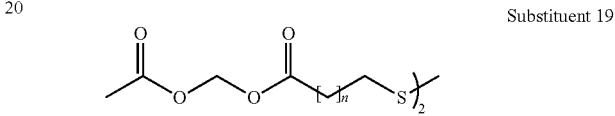

Substituent 19 where n ranges from 0-50.

Embodiments of the compounds of the invention include the following:

The invention provides compounds having formula I:

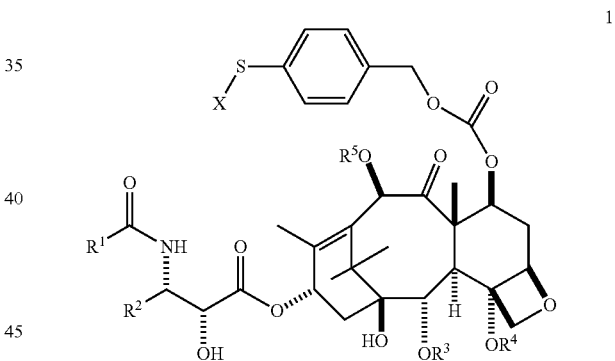

1 wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; and X is hydrogen or a leaving group, examples of which include but are not limited to a 2-thiopyridyl group; a halogen such as chlorine or bromine; a substituted sulfinate group, —$SO_2R$, where R is $C_{1-6}$ alkyl optionally substituted with one to six same or different halogen atoms, $C_{3-6}$ cycloalkyl, $C_{2-6}$ alkenyl, phenyl or 4-methylphenyl group; the group —SAr, where Ar is a benzene ring optionally substituted with nitro and/or carboxyl groups, for example, is 3-carboxy-4-nitrophenyl, or or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl.

In one embodiment, the compound is 2

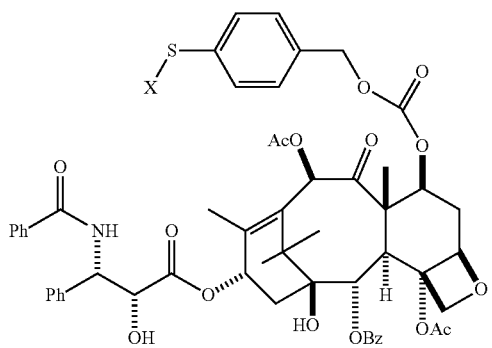

2

The synthesis of an exemplary compound 2 where X=a 2-thiopyridyl group, is illustrated in Scheme 1.1 in the Examples section below.

The invention also provides compounds having formula 3,

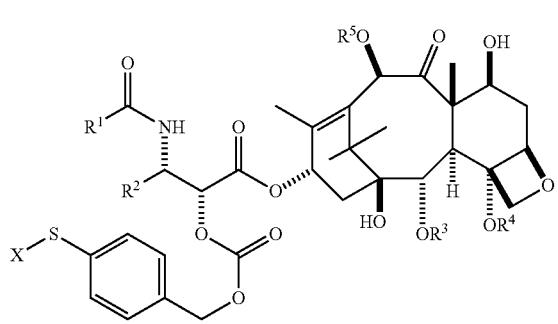

3 wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; and X is hydrogen or a leaving group, examples of which include but are not limited to: a 2-thiopyridyl group; a halogen such as chlorine or bromine; a substituted sulfinate group, $-SO_2R$, where R is $C_{1-6}$ alkyl optionally substituted with one to six same or different halogen atoms, $C_{3-6}$ cycloalkyl, $C_{2-6}$ alkenyl, phenyl or 4-methylphenyl group; the group $-SAr$, where Ar is a benzene ring optionally substituted with nitro and/or carboxyl groups, for example, is 3-carboxy-4-nitrophenyl, or or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl.

In one embodiment, the compound is 4

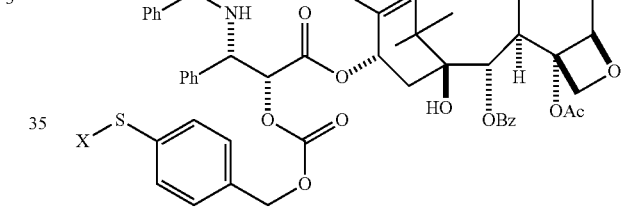

4

The synthesis of an exemplary compound 4 where X=a 2-thiopyridyl group, is illustrated in Scheme 1.3 in the Examples section below.

The invention further provides compounds having formula 5 below,

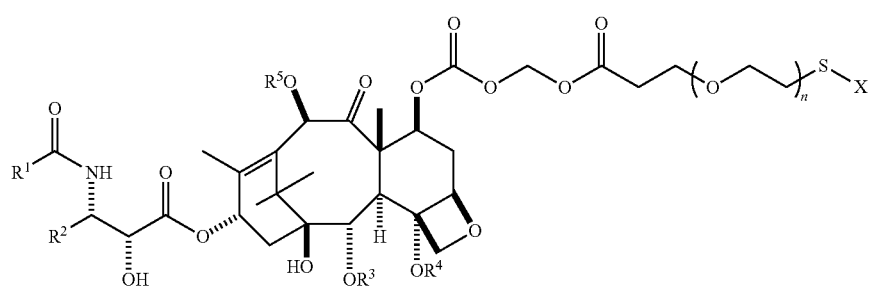

5 wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; n is any integer from 0-100; and X is hydrogen or a leaving group, examples of which include but are not limited to a 2-thiopyridyl group; a halogen such as chlorine or bromine; a substituted sulfinate group, —$SO_2R$, where R is $C_{1-6}$ alkyl optionally substituted with one to six same or different halogen atoms, $C_{3-6}$ cycloalkyl, $C_{2-6}$ alkenyl, phenyl or 4-methylphenyl group; the group —SAr, where Ar is a benzene ring optionally substituted with nitro and/or carboxyl groups, for example, is 3-carboxy-4-nitrophenyl, or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl.

In an embodiment, the compound is 6

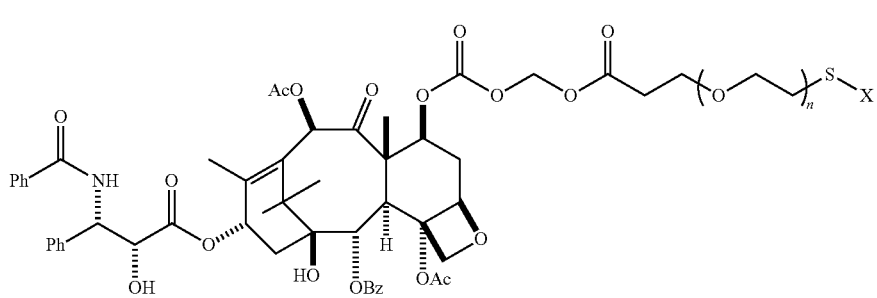

6

The invention further provides compounds having formula 7:

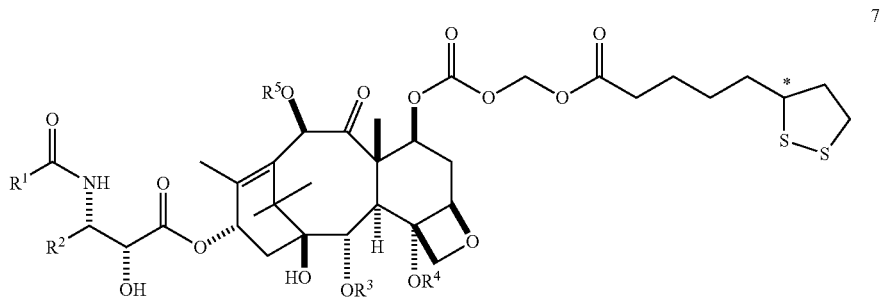

7 wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$, where $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; and the stereochemistry at the chiral center * is racemic (R/S) and may be (R/S), R or S.

In an embodiment, the compound is 8

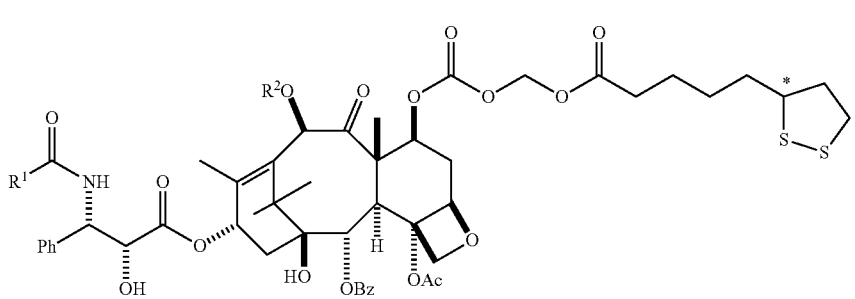

8 where R$^1$=Ph, R$^2$=acetyl; or R$^1$=(CH$_3$)$_3$CO, R$^2$=H; or R$^1$=(CH$_3$)$_3$CO, R$^2$=acetyl The stereochemistry at the chiral center * is racemic (R/S), and may be (R/S), R or S.

The invention further provides a compound having the formula 9,

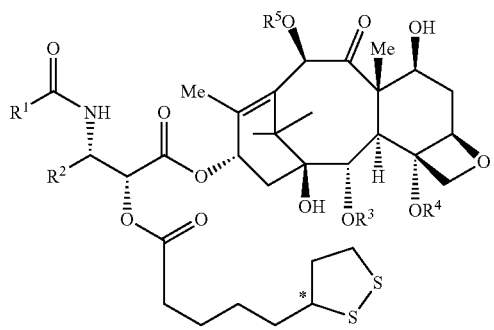

9 wherein R$^1$ is phenyl, t-butoxy, or C$_{1-6}$ alkyloxy; R$^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; R$^3$ is benzoyl, m-methoxybenzoyl, m-azidobenzoyl, or m-chlorobenzoyl; R$^4$ is C(O)R$^x$; R$^5$ is H or methyl or C(O)R$^x$, in which R$^x$ is C$_{1-6}$ alkyl optionally substituted with one to six same or different halogen atoms, C$_{3-6}$ cycloalkyl, C$_{2-6}$ alkenyl or C$_{1-6}$ alkyloxy; and the stereochemistry at the chiral center * is racemic (R/S) and may be either R or S.

In one embodiment, the compound is represented by formula 10 below, where the stereochemistry at the chiral center * is racemic (R/S) and may be (R/S), R or S.

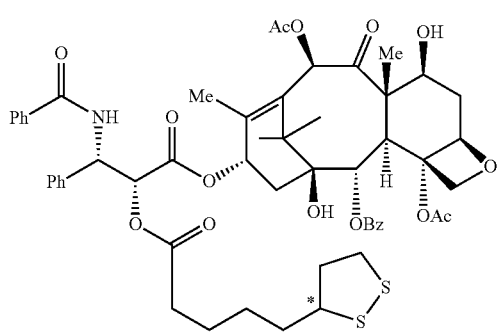

10

The invention also provides compounds having formula 11:

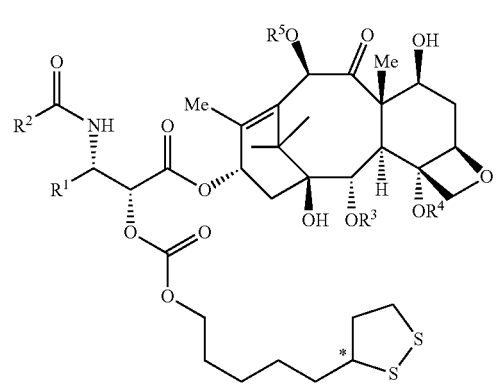

11 wherein R$^1$ is phenyl, t-butoxy, or C$_{1-6}$ alkyloxy; R$^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; R$^3$ is benzoyl, m-methoxybenzoyl, m-azidobenzoyl, or m-chlorobenzoyl; R$^4$ is C(O)R$^x$; R$^5$ is H or methyl or C(O)R$^x$ in which R$^x$ is C$_{1-6}$ alkyl optionally substituted with one to six same or different halogen atoms, C$_{3-6}$ cycloalkyl, C$_{2-6}$ alkenyl or C$_{1-6}$ alkyloxy; and wherein the stereochemistry at the chiral center * can be variously (R/S), (R), or (S).

In one embodiment, the compound is 12

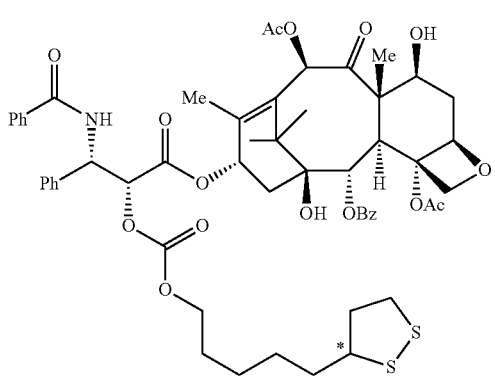

12 wherein the stereochemistry at the chiral center * can be variously (R/S), (R), or (S).

The invention further provides a compound having formula 13:

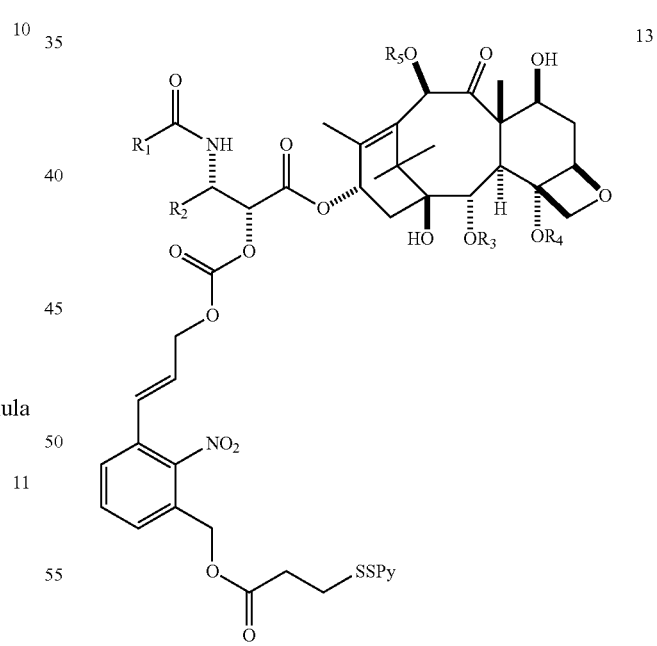

13 wherein R$^1$ is phenyl, t-butoxy, or C$_{1-6}$ alkyloxy; R$^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; R$^3$ is benzoyl, m-methoxybenzoyl, m-azidobenzoyl, or m-chlorobenzoyl; R$^4$ is C(O)R$^x$; R$^5$ is H or methyl or C(O)R$^x$; in which and R$^x$ is C$_{1-6}$ alkyl optionally substituted with one to six same or different halogen atoms, C$_{3-6}$ cycloalkyl, C$_{2-6}$ alkenyl or C$_{1-6}$ alkyloxy.

In one embodiment, the compound has formula 14 below,

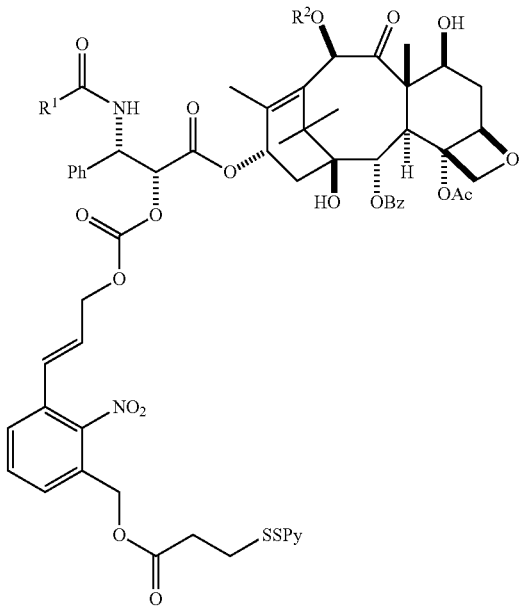

14 where $R^1$=Ph and $R^2$=acetyl; or $(CH_3)_3CO$, $R^2$=H; or $R^1$=$(CH_3)_3CO$, $R^2$=acetyl In particular, the compound may be 15

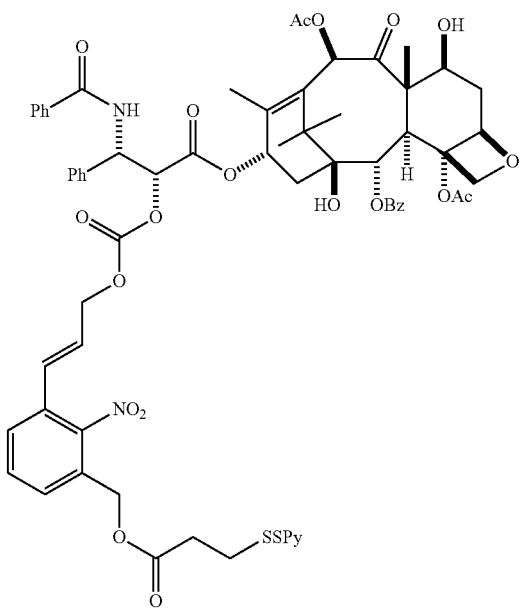

15

The invention further includes compound having formula 16:

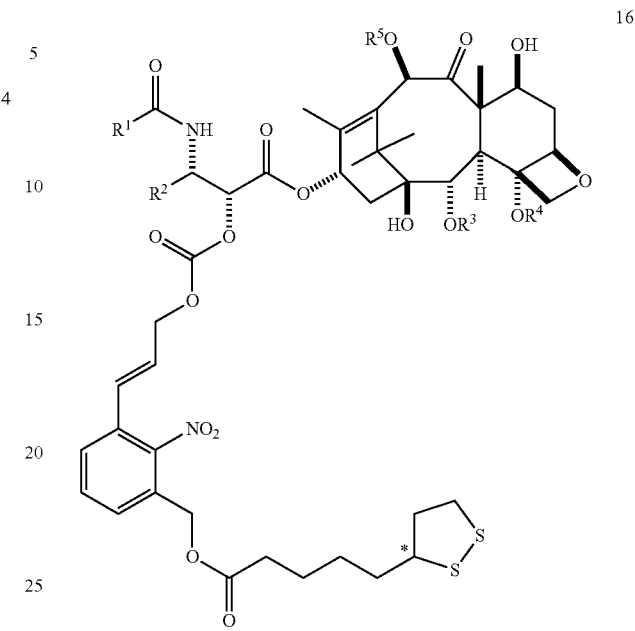

16 wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; and the stereochemistry at the chiral center (*) can be variously R, S, or R/S.

In one embodiment, the compound has the formula 17 below,

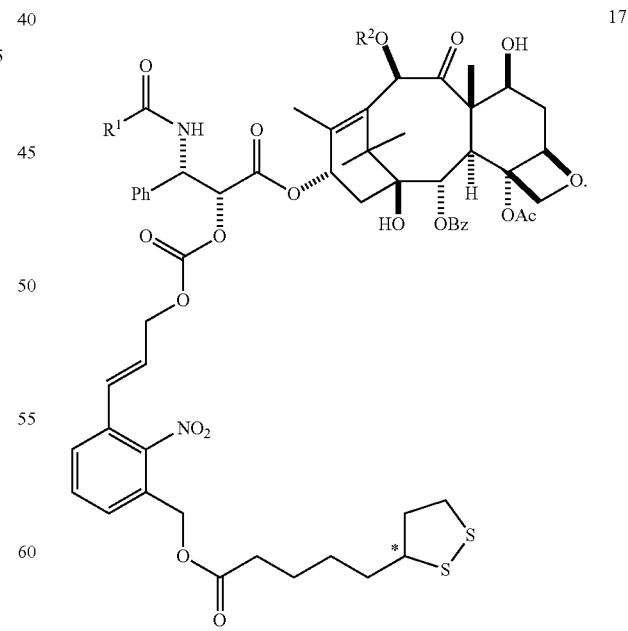

17 where $R^1$=Ph and $R^2$=acetyl; or $R^1$=$(CH_3)_3CO$, $R^2$=H; or $R^1$=$(CH_3)_3CO$, $R^2$=acetyl; and the stereochemistry at the chiral center (*) can be variously R, S, or R/S.

In particular, the compound may be 18

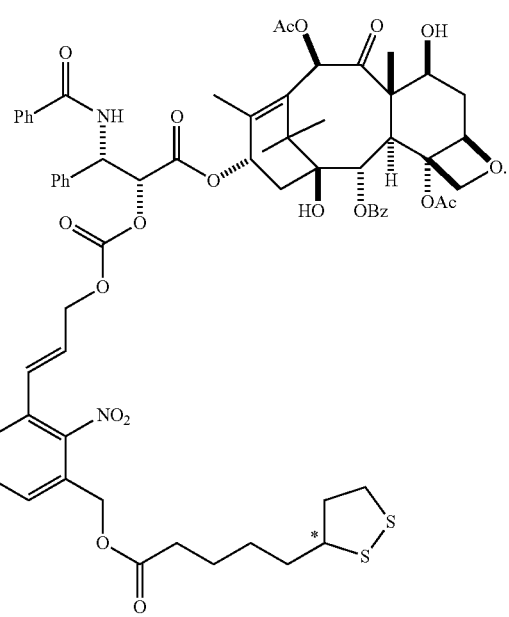

The invention further provides a compound having formula 19 below:

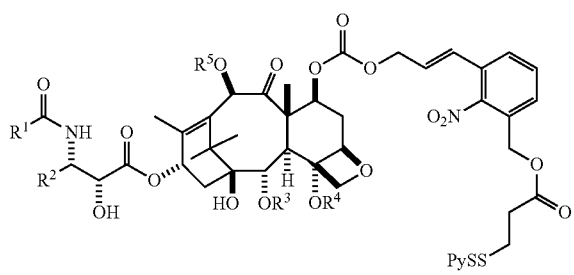

wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy;

The invention further provides a compound having formula 20 below,

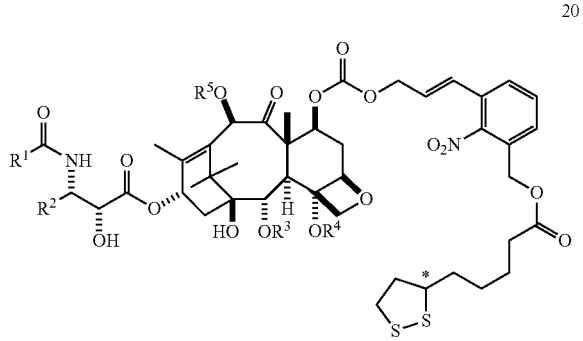

wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy, and where the stereochemistry at the chiral center * can be variously R, S, or R/S.

The invention further provides compounds having formula 21 below,

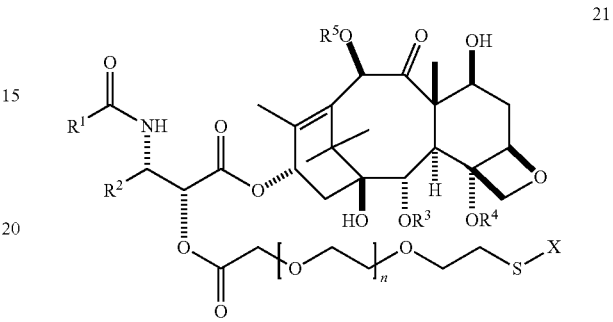

wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl; and where n is any integer from 1 to 50.

In one embodiment, $R^1=R^2$=phenyl, $R^3$=benzoyl, and $R^4=R^5$ acetyl. In an alternate embodiments, $R^1=(CH_3)_3CO$, $R^2$=phenyl, $R^3$=benzoyl, $R^4$=acetyl, and $R^5$=H.

The invention further provides compounds having formula 22,

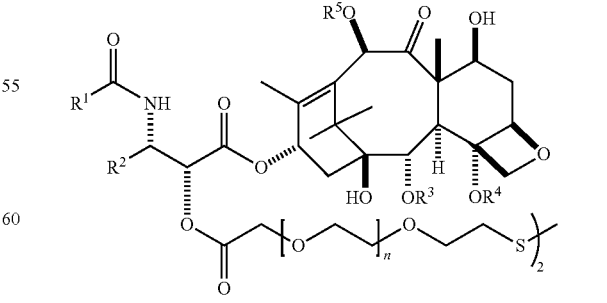

wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl; and where n is any integer from 1 to 50.

In one embodiment, $R^1$=$R^2$=phenyl, $R^3$=benzoyl, and $R^4$=$R^5$ acetyl. In an alternate embodiment, $R^1$=$(CH_3)_3CO$, $R^2$=phenyl, $R^3$=benzoyl, $R^4$=acetyl, and $R^5$=H.

The invention further provides compounds having formula 3 below, (this is now covered by the revised formula 21.)

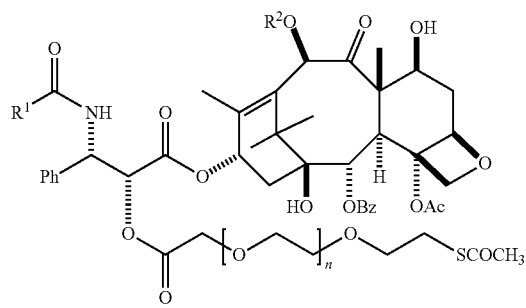

3 where n is any integer from 1 to 50; and: $R^1$=phenyl and $R^2$=acetyl; or $R^1$=$(CH_3)_3CO$ and $R^2$=H; or $R^1$=$(CH_3)_3CO$ and $R^2$=acetyl.

The invention further provides compounds having formula 4 below, (also covered by 21)

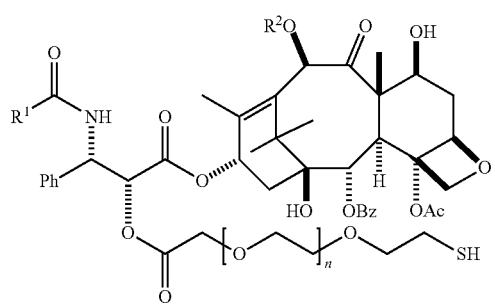

4 where n is any integer from 1 to 50; and: $R^1$=phenyl and $R^2$=acetyl; or $R^1$=$(CH_3)_3CO$ and $R^2$=H; or $R^1$=$(CH_3)_3CO$ and $R^2$=acetyl.

The invention further provides compounds having formula 23,

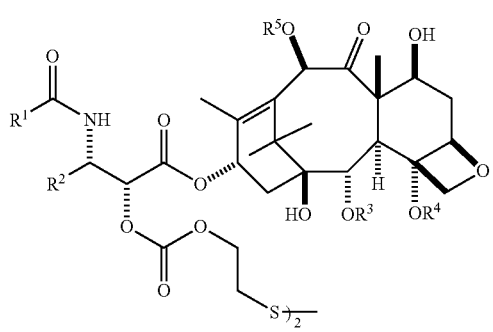

23 wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; where n is any integer from 1 to 50.

In one embodiment, $R^1$=$R^2$=phenyl, $R^3$=benzoyl, and $R^4$=$R^5$ acetyl. In an alternate embodiment, $R^1$=$(CH_3)_3CO$, $R^2$=phenyl, $R^3$=benzoyl, $R^4$=acetyl, and $R^5$=H.

The invention further provides compounds having formula 24 below,

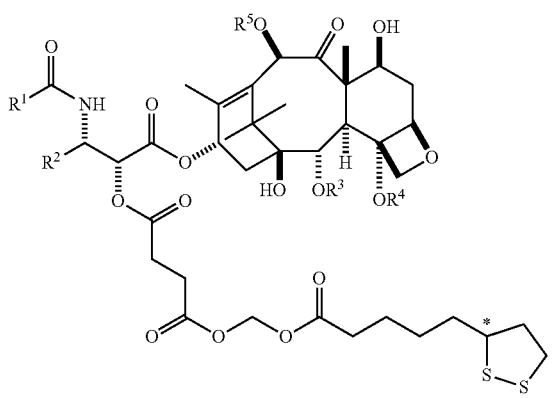

24 wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or C(O)R$^x$; and R$^x$ is C$_{1-6}$ alkyl optionally substituted with one to six same or different halogen atoms, C$_{3-6}$ cycloalkyl, C$_{2-6}$ alkenyl or C$_{1-6}$ alkyloxy, and the stereochemistry at the lipoic acid chiral center * can be variously R, S, or R/S.

In a one embodiment, R$^1$=R$^2$=phenyl, R$^3$=benzoyl, and R$^4$=R$^5$ acetyl. In an alternate embodiment, R$^1$=(CH$_3$)$_3$CO, R$^2$=phenyl, R$^3$=benzoyl, R$^4$=acetyl, and R$^5$=H. and the stereochemistry at the lipoic acid chiral center * can be variously R, S, or R/S.

The invention further provides compounds having formula 25 below,

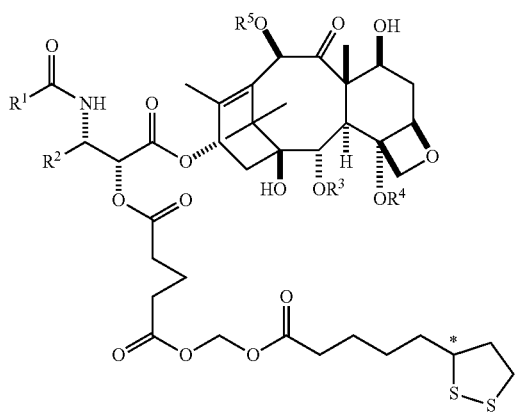

25 wherein R$^1$ is phenyl, t-butoxy, or C$_{1-6}$ alkyloxy; R$^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; R$^3$ is benzoyl, m-methoxybenzoyl, m-azidobenzoyl, or m-chlorobenzoyl; R$^4$ is C(O)R$^x$; R$^5$ is H or methyl or C(O)R$^x$; and R$^x$ is C$_{1-6}$ alkyl optionally substituted with one to six same or different halogen atoms, C$_{3-6}$ cycloalkyl, C$_{2-6}$ alkenyl or C$_{1-6}$ alkyloxy, and the stereochemistry at the lipoic acid chiral center * can be variously R, S, or R/S.

In one embodiment, R$^1$=R$^2$=phenyl, R$^3$=benzoyl, and R$^4$=R$^5$ acetyl. In an alternate embodiment, R$^1$=(CH$_3$)$_3$CO, R$^2$=phenyl, R$^3$=benzoyl, R$^4$=acetyl, and R$^5$=H, and the stereochemistry at the lipoic acid chiral center * can be variously R, S, or R/S.

The invention further provides compounds having formula 26 below,

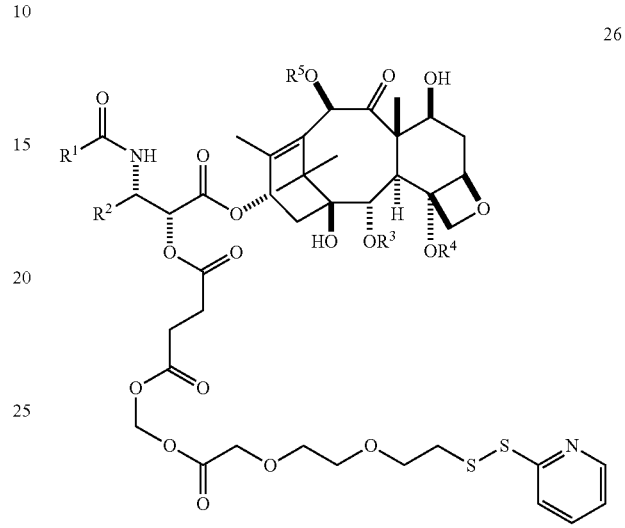

26 wherein R$^1$ is phenyl t-butoxy, or C$_{1-6}$ alkyloxy; R$^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; R$^3$ is benzoyl, m-methoxybenzoyl, m-azidobenzoyl, or m-chlorobenzoyl; R$^4$ is C(O)R$^x$; R$^5$ is H or methyl or C(O)R$^x$; and R$^x$ is C$_{1-6}$ alkyl optionally substituted with one to six same or different halogen atoms, C$_{3-6}$ cycloalkyl, C$_{2-6}$ alkenyl or C$_{1-6}$ alkyloxy.

In one embodiment, R$^1$=R$^2$=phenyl, R$^3$=benzoyl, and R$^4$=R$^5$ acetyl. In an alternate embodiment, R$^1$=(CH$_3$)$_3$CO, R$^2$=phenyl, R$^3$=benzoyl, R$^4$=acetyl, and R$^5$=H.

The invention further provides compounds having formula 27 below,

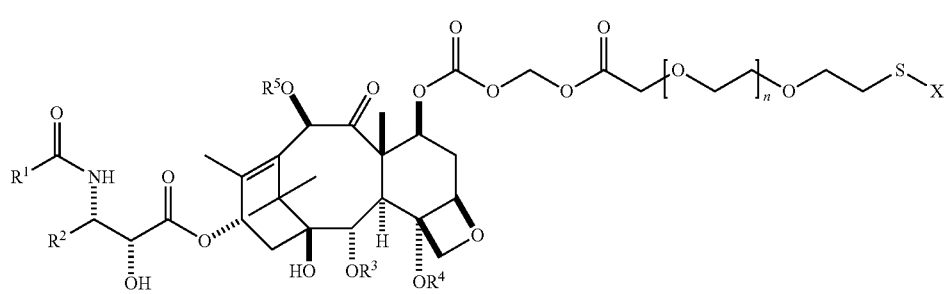

27 wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$alkyloxy; where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl; and where n is any integer from 1 to 50.

In one embodiment, $R^1$=$R^2$=phenyl, $R^3$=benzoyl, and $R^4$=$R^5$ acetyl. In an alternate embodiment, $R^1$=$(CH_3)_3CO$, $R^2$=phenyl, $R^3$=benzoyl, $R^4$=acetyl, and $R^5$=H.

The invention further provides compounds having formula 28 below,

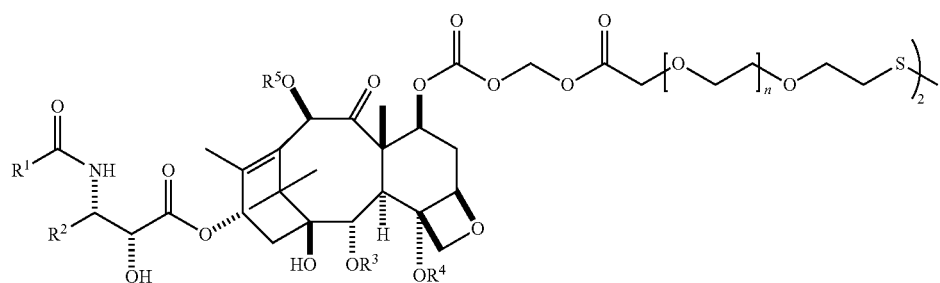

wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy, and where n is any integer from 1 to 50.

In one embodiment, $R^1$=$R^2$=phenyl, $R^3$=benzoyl, and $R^4$=$R^5$ acetyl. In an alternate embodiment, $R^1$=$(CH_3)_3CO$, $R^2$=phenyl, $R^3$=benzoyl, $R^4$=acetyl, and $R^5$=H.

The invention further provides compounds having formula 29 below, wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R'$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy, and where n is any integer from 1 to 50.

In one embodiment, $R^1$=$R^2$=phenyl, $R^3$=benzoyl, and $R^4$=$R^5$ acetyl. In an alternate embodiment, $R^1$=$(CH_3)_3CO$, $R^2$=phenyl, $R^3$=benzoyl, $R^4$=acetyl, and $R^5$=H.

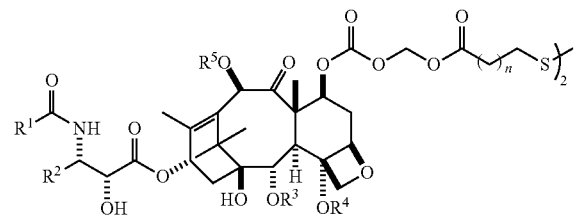

The invention further provides compounds having formula 30 below, wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl; and where n is any integer from 1 to 10.

In one embodiment, $R^1=R^2=$phenyl, $R^3=$benzoyl, and $R^4=R^5$ acetyl. In an alternate embodiment, $R^1=(CH_3)_3CO$, $R^2=$phenyl, $R^3=$benzoyl, $R^4=$acetyl, and $R^5=$H.

The present invention also provides taxane derivatives having the formula 31 below with a carbonate group at the C-2' position of paclitaxel linked to a diethylene glycol unit which is then linked to a thiolated unit, wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl; and where n is any integer from 1 to 10.

In one embodiment, $R^1=R^2=$phenyl, $R^3=$benzoyl, and $R^4=R^5$ acetyl. In an alternate embodiment, $R^1=(CH_3)_3CO$, $R^2=$phenyl, $R^3=$benzoyl, $R^4=$acetyl, and $R^5=$H.

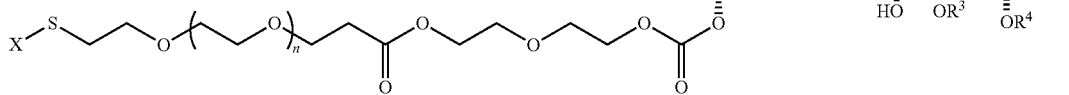

31

The present invention also provides taxane derivatives having the formula (32, n=7), with paclitaxel substituted at the 2'-position with a thiolated heptaethylene glycol, wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{1-6}$ alkenyl, or phenyl; and where n is any integer from 1 to 10.

In one embodiment, $R^1=R^2=$phenyl, $R^3=$benzoyl, j and $R^4=R^5$ acetyl. In an alternate embodiment, $R^1=(CH_3)_3CO$, $R^2=$phenyl, $R^3=$benzoyl, $R^4=$acetyl, and $R^5=$H.

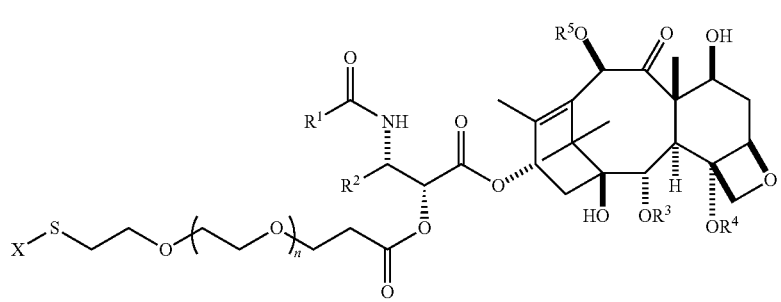

32

The present invention also provides taxane derivatives having the formula 33. wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl; and where n is any integer from 1 to 10.

In one embodiment, $R^1=R^2=$phenyl, $R^3=$benzoyl, and $R^4=R^5$ acetyl, and n=7. In an alternate embodiment, $R^1=(CH_3)_3CO$, $R^2=$phenyl, $R^3=$benzoyl, $R^4=$acetyl, $R^5=$H, and n=7.

where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl; and where n is any integer from 1 to 10.

In one embodiment, $R^1=R^2=$phenyl, $R^3=$benzoyl, and $R^4=$acetyl, and n=7. In an alternate embodiment, $R^1=(CH_3)_3CO$, $R^2=$phenyl, $R^3=$benzoyl, $R^4=$acetyl, and n=7.

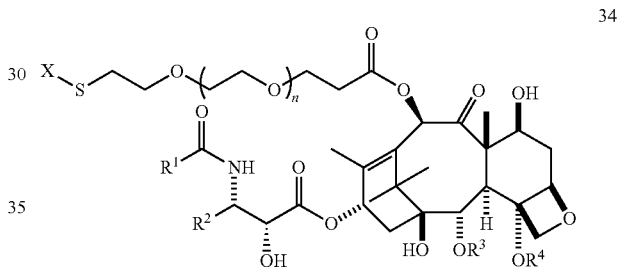

34

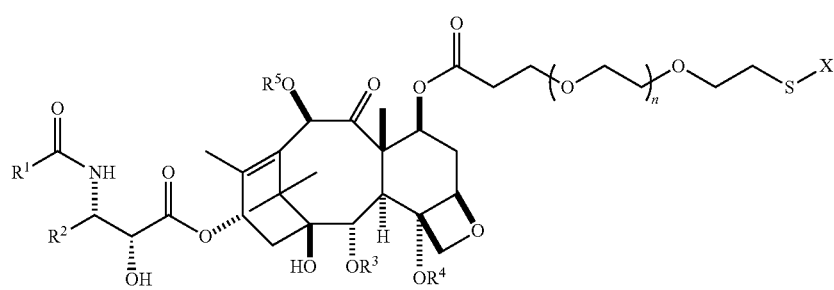

33

The present invention also provides taxane derivatives having the formula 34, wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr The present invention also provides taxane derivatives having the formula 35, wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl; and where n is any integer from 1 to 10.

In one embodiment, $R^1=R^2$=phenyl, $R^3$=benzoyl, and $R^4$=acetyl, and n=7. In an alternate embodiment, $R^1=(CH_3)_3CO$, $R^2$=phenyl, $R^3$=benzoyl, $R^4$=acetyl, and n=7.

The present invention also provides taxane derivatives having the formula 37, wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ and $R^5$ are $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy.

In one embodiment, $R^1=R^2$=phenyl, $R^3$=benzoyl, and $R^4=R^5$=acetyl. In an alternate embodiment, $R^1=(CH_3)_3CO$, $R^2$=phenyl, $R^3$=benzoyl, and $R^4=R^5$=acetyl.

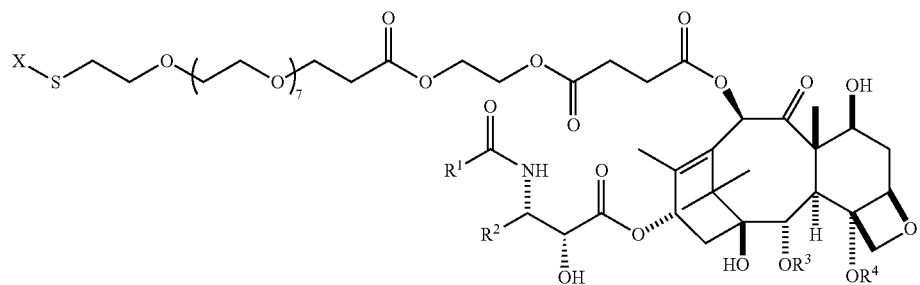

35

The present invention also provides taxane derivatives having the formula 36, wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ and $R^5$ are $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy.

In one embodiment, $R^1=R^2$=phenyl, $R^3$=benzoyl, and $R^4=R^5$=acetyl. In an alternate embodiment, $R^1=(CH_3)_3CO$, $R^2$=phenyl, $R^3$=benzoyl, and $R^4=R^5$=acetyl.

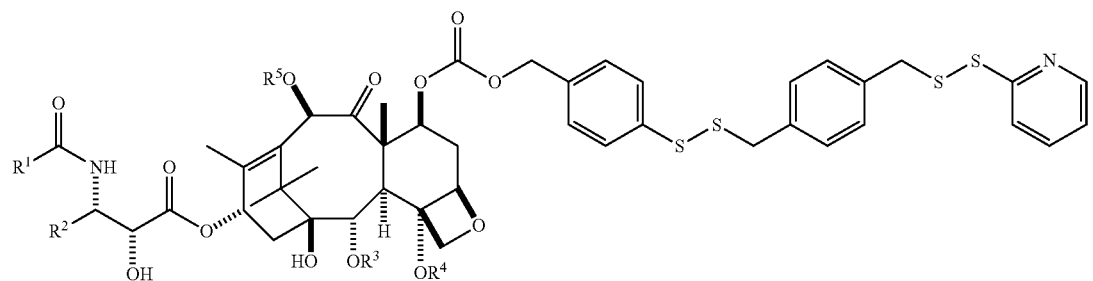

36

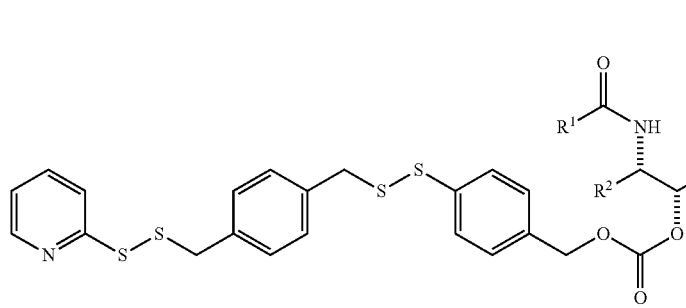
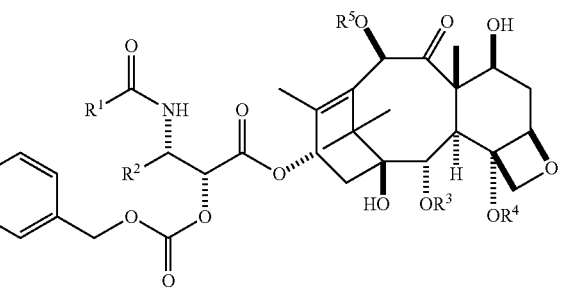

37

The present invention also provides taxane derivatives having the formula 38, wherein $R^1$ is phenyl, t-butoxy, or $C_{1-6}$ alkyloxy; $R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl; $R^3$ is benzoyl, m-methoxybenzoyl, m-azidobenzoyl, or m-chlorobenzoyl; $R^4$ is $C(O)R^x$; $R^5$ is H or methyl or $C(O)R^x$; and $R^x$ is $C_{1-6}$ alkyl optionally substituted with one to six same or different halogen atoms, $C_{3-6}$ cycloalkyl, $C_{2-6}$ alkenyl or $C_{1-6}$ alkyloxy; where X is hydrogen; a 2-thiopyridyl group; a halogen; a substituted sulfinate group —$SO_2R$ where R is $C_{1-6}$ alkyl optionally substituted with one to six halogen atoms that may be the same or different, $C_{3-6}$ cycloalkyl; $C_{2-6}$ alkenyl, phenyl or 4-methylphenyl; or SAr where Ar is: a benzene ring optionally substituted with nitro or carboxyl groups or both nitro and carboxyl groups, such as, for example, 3-carboxy-4-nitrophenyl; or an acyl group $R_1CO$, where $R_1$ is $C_{1-6}$ alkyl optionally substituted with one to six halogen atoms that may be the same or different, $C_{3-6}$ cycloalkyl; $C_{2-6}$ alkenyl, or phenyl; and where n is any integer from 1 to 50.

By "metal nanoparticles" we mean particles that are of a size that is in the nanometer range, e.g. less than about 1000 nm in the longest dimension of the particle. Such particles are less than about 500 nm, preferably less than about 250 nm, more preferably less than about 100 nm in size, and even more preferably less than 50 nm. In fact, current technology can provide nanometal particles of sizes less than 25, 20, 15, 10, 9, 8, 7, 6, 5, 4, 3, 2, and 1 nanometer. Generally, sizes in the range of from about 2 to about 10, or from about 2 to about 5 nm are preferred. When in solution, such particles e.g. gold, are typically referred to as "colloidal" e.g. "colloidal gold" and are present in the solution as a suspension or colloidial suspension. Metals that can be used in the practice of the invention include but are not limited to gold, silver, copper, nickel, aluminum, zinc, calcium, platinum, palladium, iron, etc., and mixtures or other combinations thereof (e.g. alloys, layers or shells of different metals, etc.), with the preferred metal being gold.

By nanoparticle "size" or "size range" we mean that the average longest dimension of the nanoparticles in a collection

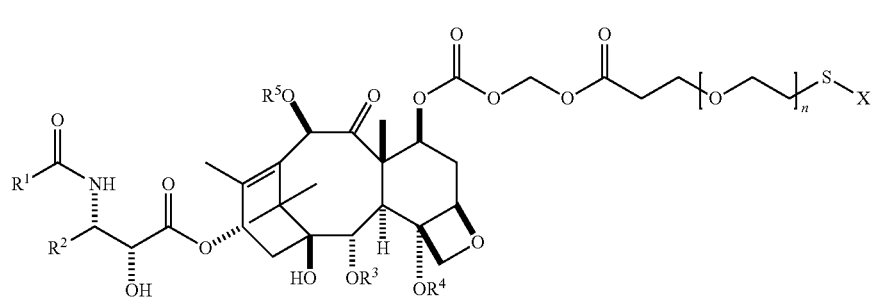

38

In one embodiment, $R^1=R^2$=phenyl, $R^3$=benzoyl, and $R^4=R^5$ acetyl. In an alternate embodiment, $R^1=(CH_3)_3CO$, $R^2$=phenyl, $R^3$=benzoyl, $R^4$=acetyl, and $R^5$=H. The synthesis of an exemplary compound 38 where X=a 2-thiopyridyl group, is illustrated in Scheme 2.1 in the Examples section below.

By "active" or "fully active" we mean that the activity of the paclitaxel moiety of the derivative that is delivered to a cell or tissue by the methods of the invention, is, upon delivery to the cell of tissue, at least about 50%, preferably about 60%, more preferably about 70%, and most preferably about 80% or more (e.g. 90, 95, or even 100% or greater) of the activity of intact paclitaxel (paclitaxel that is not derivatized and attached to a metal nanoparticle) when measured under standardized conditions (e.g. in the same or in an equivalent environment).

or preparation of nanoparticles falls within the nanometer range as described above. Those of skill in the art will recognize that the "longest dimension" of a particle will depend on the shape of the particle. For example, for particles that are roughly or substantially spheroid, the longest dimension will be a diameter of the particle. For other particles (e.g. for angular shapes) the longest dimension may be e.g. a diagonal, a side, etc. Those of skill in the art will also recognize that in a given preparation of metal nanoparticles, the sizes and shapes of the particles may vary, depending, for example, on the method of preparation. The shape of nanometal particles used in the practice of the invention is generally substantially spherical, but this need not always be the case. The invention also encompasses paclitaxel derivatives attached to nanometal particles that are substantially rods, cubes, caps, triangular or disc-like plates, elongated "wires", or even coated on other nanoparticulate substances, etc. The preparation of metallic nanoparticles, especially gold nanoparticles that may be administered therapeutically, is described, for example, in US patent application 2006/0222595 to Mukherjee et al., and in U.S. Pat. Nos. 7,232,474 to Bouvrette et al., 7,060,121 to Lin et al., and 6,929,675 to Bunge et al., the complete contents of each of which is hereby incorporated by reference.

According to the invention, the paclitaxel derivatives of the invention are attached to metal, preferably gold, nanoparticles, and the invention encompasses metallic nanoparticles with the paclitaxel derivatives of the invention attached (sometimes referred to herein as "complexes"), as well as compositions containing such nanoparticle-derivative complexes. This attachment is generally covalent in nature, through a thiol group of the derivative bonding to the gold nanoparticle. The binding of thiols to palladium has been described by Lina Xu, Jianhui Liao, Lan Huang, Ning Gu, Haiqian Zhang, and Juzheng Liu, *Applied Surface Science* 211 (2003) 184-188. The binding of thiols to copper has been described by H. Keller "Surface chemistry of thiols on copper: an efficient way of producing multilayers" Thin Solid Films, Vol. 244, No. 1-2. (15 May 1994), pp. 799-805.

In some embodiments of the invention, one or more molecules of a single type of compound of the invention is/are attached to individual metallic nanoparticles. In other embodiments of the invention, one or more molecules of two or more different compounds of the invention are attached to individual metallic nanoparticles. In yet other embodiments of the invention, molecules other than the compounds of the invention are also attached to the nanoparticles, together with the compounds of the invention. Examples of such other molecules include but are not limited to antibodies (e.g. that target cancerous tumors or other unwanted cells); various peptide sequences that target the nanoparticles to a particular cell type (e.g. cancerous tumors or other unwanted cells); ligands for receptors that are over-expressed by tumors, various apoptotic or necrotic factors (e.g. tumor necrosis factor α, TNFα), etc. In some embodiments, the complexes also comprise TNFα.

In additional embodiments, the compositions of the present invention further may comprise one or more ligands, antibodies, antibody fragments, enzymes, cofactors, and substrates, as well as one or more integrating molecules or agents, examples of which include but are not limited to TNF, interleukins, growth factors, hormones, cofactors, enzyme substrates, immunoregulatory molecules, adhesion molecules, vascular markers, neovascular markers, molecular chaperones, and heat shock proteins.

In alternative embodiments, the colloidal metal particle may be modified using polyethylene glycol, POLYPEG®, polyoxypropylene, polymers, polyvinylpyrrolidone polymers, rPEG, or hydroxyethyl starch.

In other embodiments, the compositions of the present invention may further comprise chemical agents, therapeutic agents, pharmaceutical agents, drugs, biological factors, fragments of biological molecules such as antibodies, proteins, lipids, nucleic acids or carbohydrates; nucleic acids, antibodies, proteins, lipids, nutrients, cofactors, nutriceuticals, anesthetic, or detection agents.

In other embodiments, the compositions of the present invention may further comprise cytokines, growth factors, neurochemicals, cellular communication molecules, hormones, pharmaceuticals, anti-inflammatory agents, chemotherapeutic agents, immunotherapy agents, nucleic acid-based materials, dyes, and radioactive materials.

The invention also provides compositions for linking paclitaxel to monoclonal antibodies for targeted drug delivery without the use of nanoparticles. The use of monoclonal antibodies for delivery of paclitaxel to tumors is well known (Guillemard V, Saragovi H U. Taxane-antibody conjugates afford potent cytotoxicity, enhanced solubility, and tumor target selectivity. Cancer Res. 2001, 61, 694-699) and the thiol group is a preferred group for linking taxol to antibodies (Wu X, Ojima I. Tumor specific novel taxoid-monoclonal antibody conjugates. Curr. Med. Chem. 2004, 11, 429-438). The subjects of this invention thus provide a selection of paclitaxel derivatives that can be readily linked to monoclonal antibodies through a cysteine residue in the antibody.

Other possible molecules or structures (substrates) to which the compounds of the invention may be linked will also occur to those of skill in the art, and are intended to be encompassed by the present invention. The analogs may be attached to a variety of substrates, examples include but are not limited to: various synthetic supports (e.g. beads); various macromolecules (e.g. proteins, peptides, lipids, nucleic acids, etc.), etc.

The invention also provides compositions for administration to a subject. The compositions generally include one or more types of the novel paclitaxel derivative-metal nanoparticle complexes of the invention as described herein. The subject to whom the compositions are administered is usually a mammal (frequently a human), but this need not always be the case. Veterinary applications of this technology are also contemplated. The compositions are used to treat diseases or conditions, the symptoms of which can be ameliorated or eliminated by the administration of paclitaxel. Such diseases/conditions include but are not limited to various types of cancers, including but not limited to lung cancer, ovarian cancer, breast cancer, head and neck cancer, prostate cancer, advanced forms of Kaposi's sarcoma, melanoma, bladder cancer, colon cancer, stomach cancer, pancreatic cancer, etc. However, other diseases or conditions may also be treated, or in some cases prevented, by administration of the compositions of the invention, examples of which include but are not limited to restenosis, benign tumors, Alzheimer's disease, etc. Those of skill in the art are familiar with the mechanism of action of paclitaxel, (interference with normal microtubule breakdown during cell division) and any disease or condition for which symptoms can be alleviated, lessened, or eradicated by this action may be treated using the compounds and compositions of the invention.

The compositions of the invention include a plurality of at least one type of metallic nanoparticle to which are attached a plurality of molecules of at least one type of compound of the invention, and a pharmacologically suitable carrier. The preparation of such compositions (i.e. compositions for administration) is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain other beneficial substances, e.g. vitamins, immune system stimulating agents, anti-nausea agents, etc. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of metallic nanoparticle-paclitaxel complex in the formulations may vary. However, in general, the amount in the formulations will be from about 1-99%.

The compositions (preparations) of the present invention may be administered by any of the many suitable means which are well known to those of skill in the art, including but not limited to by injection (either intravenous or intratumoral), orally, topically, or via an implant that delivers the composition gradually and/or directly to a site of action (e.g. a tumor, a blood vessel that may restenose, etc.). In preferred embodiments, the mode of administration for cancer treatment is by intravenous or intratumoral injection. For the treatment or prevention of restenosis, administration is typically by incorporating the drug or drug complex into the lining of a stent. In this case, the compounds could, for example, be bonded directly to a gold layer plated onto a metal or plastic stent. In addition, the compositions may be administered in conjunction with other treatment modalities such as substances that boost the immune system, various chemotherapeutic agents, antibiotic agents, anti-nausea agents, appetite stimulants, blood thinners, etc.

As will be recognized by those of skill in the art, the dosage of such compositions is generally predicated on known dosing regimens for paclitaxel. Standard protocols for the administration of paclitaxel are described, for example, in Arbuck S G, Blaylock B A Taxol: Clinical Results and Current Issues in Development. In: Taxol: Science and applications, ed. Suffness, M. CRC Press: Boca Raton, 1995, pp. 379-415. One of skill in the art (e.g. a physician or other health care professional) will recognize that such factors as the gender, weight, age, ethnogenecity, etc. of the subject being treated may also be taken into account, as well as factors specific to the disease or malady being treated, the stage of treatment, overall health of the patient, etc. In addition, the amount of composition to be administered will take into account factors such as the density of particle loading (i.e. the number of paclitaxel derivative molecules per nanoparticle). Because the compounds of the present invention promote stabilization of the active (paclitaxel) moiety of the complexes, it is possible that lower doses of the drug may be administered, or that administration can be less frequent, or that a shorter period of treatment will be necessary to achieve a beneficial therapeutic effect, compared to other paclitaxel delivery methods.

The invention also includes methods of stabililzing paclitaxel derivatives of the invention by attaching them to nanoparticles, preferably gold nanoparticles. In related embodiments, the invention provides slow-release forms of the paclitaxel derivatives of the invention in which the derivatives are attached to nanoparticles, preferably gold nanoparticles, and methods for using such complexes to effect the slow release of paclitaxel at a desired site such as in the vicinity of tumor cells (e.g. near or even within a tumor), or in the vicinity of cells that may restenose, etc.

A particularly advantageous feature of the paclitaxel analogs described herein is that their use with the gold nanoparticle enables the delivery of the drug in greater concentration, as conversion to the active form is delayed until the target site is reached. Though not wishing to be bound to the following theory, it is thought that the presence of the gold particle contributes to the delayed hydrolysis of the thiolated paclitaxel. In addition, it is also thought that particularly engineered forms of the analogs described and claimed herein enable delayed hydrolysis and conversion, thereby resulting in more effective drug delivery.

Preferred paclitaxel analogs of the present invention comprise analogs II, IV, and XIII. In the Examples section below, Synthesis schemes 1.3, 1.1 and 2.1 show the syntheses of analogs II, IV, and XIII respectively. Due to the numbering schemes employed in the Examples, analog II is compound 8 in Scheme 1.3; analog IV is compound 5 in Scheme 1.1; and analog XIII is compound 13 in Scheme 2.1.

Figure 5:
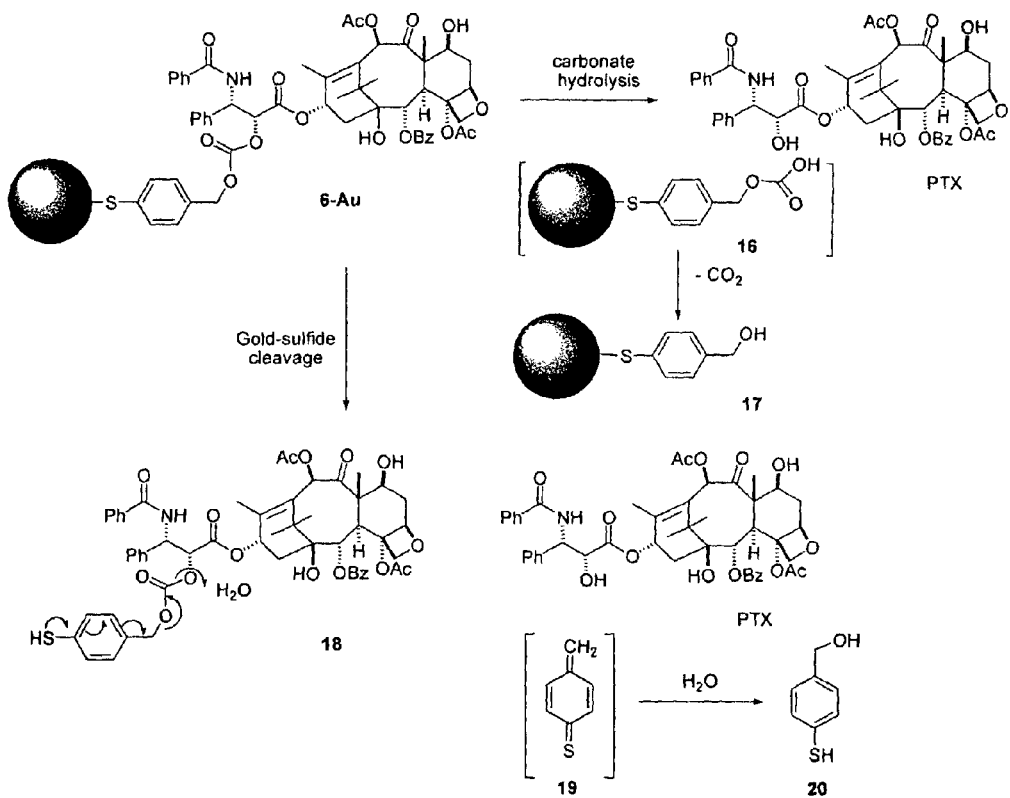
FIG. 5 is a schematic providing the proposed pathways for conversion of gold-bound analog II to paclitaxel.
Figure 6:
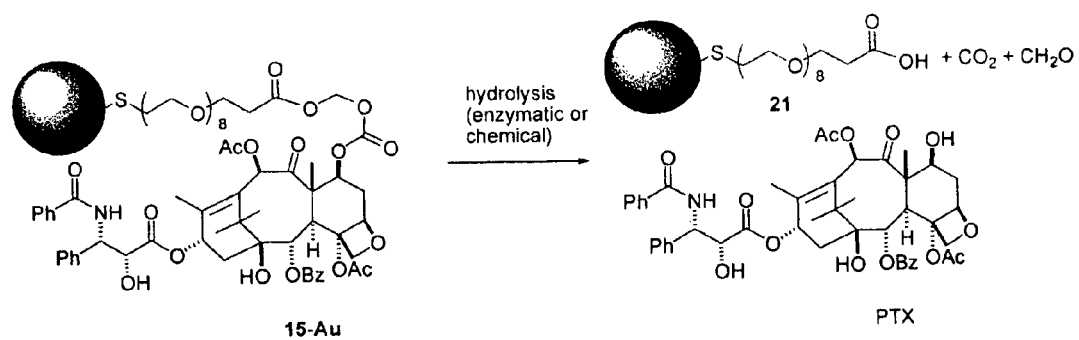
FIG. 6 provides a proposed pathway for the conversion of gold-bound analog XIII to paclitaxel.

The mechanisms of paclitaxel release from the paclitaxel analogs provided herein are likely to be similar, so the representative mechanism for analog II is provided in FIG. 5 and discussed in Example 18 below. In summary, though not wishing to be bound by the following theory, it is thought that paclitaxel release from analogs is likely to occur via hydrolysis or via reductive cleavage of the gold-sulphur bond. As explained in Example 18 and shown in FIG. 6, the mechanism of release for analog XIII is also thought to be via hydrolysis. An important aspect of these mechanisms and reactions is that when bound to gold, the hydrolytic conversion of these analogs to paclitaxel occurs at a significantly slower rate. In essence therefore, one novel and highly desirable aspect of this nanoparticle is that gold contributes to the stabilization of the paclitaxel analog and significantly decreases premature conversion or activation in plasma, namely, a majority of the paclitaxel is not present in its active form until it reaches its target.

Further analysis of analogs II, IV, and XIII in conjunction with paclitaxel is provided in Example 19 wherein the conversion of thiolated paclitaxel analogs to paclitaxel in physiologic and non-physiologic conditions is discussed. In addition, Example 20 provides discussion pertaining to the characterization of the binding of analogs II, IV, and XIII to colloidal gold nanoparticles. The analytical and characterization data were then combined to create a nanotherapeutic using the novel analogs in conjunction with paclitaxel (Example 21). Examples 22 and 23 provide detailed information concerning in vitro and in vivo studies carried out evaluate the appropriateness of the analogs for incorporation into therapeutics. Example 24 confirms the therapeutic value of TNF in addition to its function as a targeting ligand for the present nanotherapeutic. Finally, the efficacy studies discussed in Example 25 provide evidence supporting the conclusion that the nanodrugs of the present invention comprising a gold platform, together with TNF, paclitaxel analogs and PEG-THIOL, result in the targeted delivery of paclitaxel to tumor sites, and therefore induce a paclitaxel mediated anti-tumor response at a significantly lower dose of drug than with unformulated paclitaxel treatment. For example, the analog tested at a dose of 2.5 mg/kg was more effective than the same dose of unformulated paclitaxel. Based on these data the novel nanotherapeutics of the present invention appear to be at least 16-fold more effective than paclitaxel since 2.5 mg/kg was as effective as 40 mg/kg of paclitaxel.

The practice of the invention is further illustrated by the following non-limiting Examples.

EXAMPLES

General experimental methods. All of the reagents and solvents received from commercial sources were used without further purification. $^1$H and $^{13}$C NMR spectra were obtained on Varian Unity 400 MHz, Inova 400 MHz, and JEOL Eclipse 500 MHz spectrometers in CDCl$_3$. High resolution FAB mass spectra were obtained on a JEOL HX-110 instrument. Reaction mixtures were worked up by the standard procedure of quenching the reaction, extracting the resulting aqueous mixture with EtOAc, Et$_2$O or dichloromethane, washing the organic solution with water and brine, drying over Na$_2$SO$_4$, filtering, and concentration to give crude product.

Example 1.1

Synthesis of an M1 Type Compound of Substituent 1
(6 in this Example)

Paclitaxel (1) was reacted with tert-butyldimethylsilyl chloride (Liu, C.; Strobl, J. S.; Bane, B.; Schilling, J. K.; McCracken, M.; Chatterjee, S. K.; Rahim-Bata, R.; Kingston, D. G. I. *J. Nat. Prod.* 2004, 67, 152-159.) to yield C2'-TBS paclitaxel (2). Compound 2 was reacted with bis(4-nitrophenyl)carbonate to give the 7-carbonate derivative 3 (Fardis, M.; Pyun, H.-J.; Tario, J.; Jin, H.; Kim, C. U.; Ruckman, J.; Lin, Y.; Green, L.; Hicke, B. *Bioorg. Med. Chem.* 2003, 11, 5051-5058). para-Mercaptobenzyl alcohol was obtained from the commercially available compound 4-(methylthio)benzyl alcohol (Aldrich Chemical Company #230685), following literature methods (Young, R. N.; Gauthier, J. Y.; Coombs, W. *Tetrahedron Lett.* 1984, 25, 1753-1756). Coupling of para-mercaptobenzyl alcohol with 2,2'-pyridyl disulfide resulted in the formation of the disulfide 4 (Senter, P. D.; Pearce, W. E.; Greenfield, R. S. *J. Org. Chem.* 1990, 55, 2975-2978; Ebright, Y. W.; Chen, Y.; Kim, Y.; Ebright, R. H. Bioconjugate Chem. 1996, 7, 380-384). The 7-carbonate derivative 3 was reacted with disulfide 4 to give the 7-carbonate 5 (Fardis, M.; Pyun, H.-J.; Tario, J.; Jin, H.; Kim, C. U.; Ruckman, J.; Lin, Y.; Green, L.; Hicke, B. *Bioorg. Med. Chem.* 2003, 11, 5051-5058; Liu, C.; Schilling, J. K.; Ravindra, R.; Bane, S.; Kingston, D. G. I. *Bioorg. Med. Chem.* 2004, 12, 6147-6161). Deprotection of 5 with HF-pyridine gave the benzyl carbonate disulfide 6 (Liu, C.; Strobl, J. S.; Bane, B.; Schilling, J. K.; McCracken, M.; Chatterjee, S. K.; Rahim-Bata, R.; Kingston, D. G. I. *J. Nat. Prod.* 2004, 67, 152-159.)

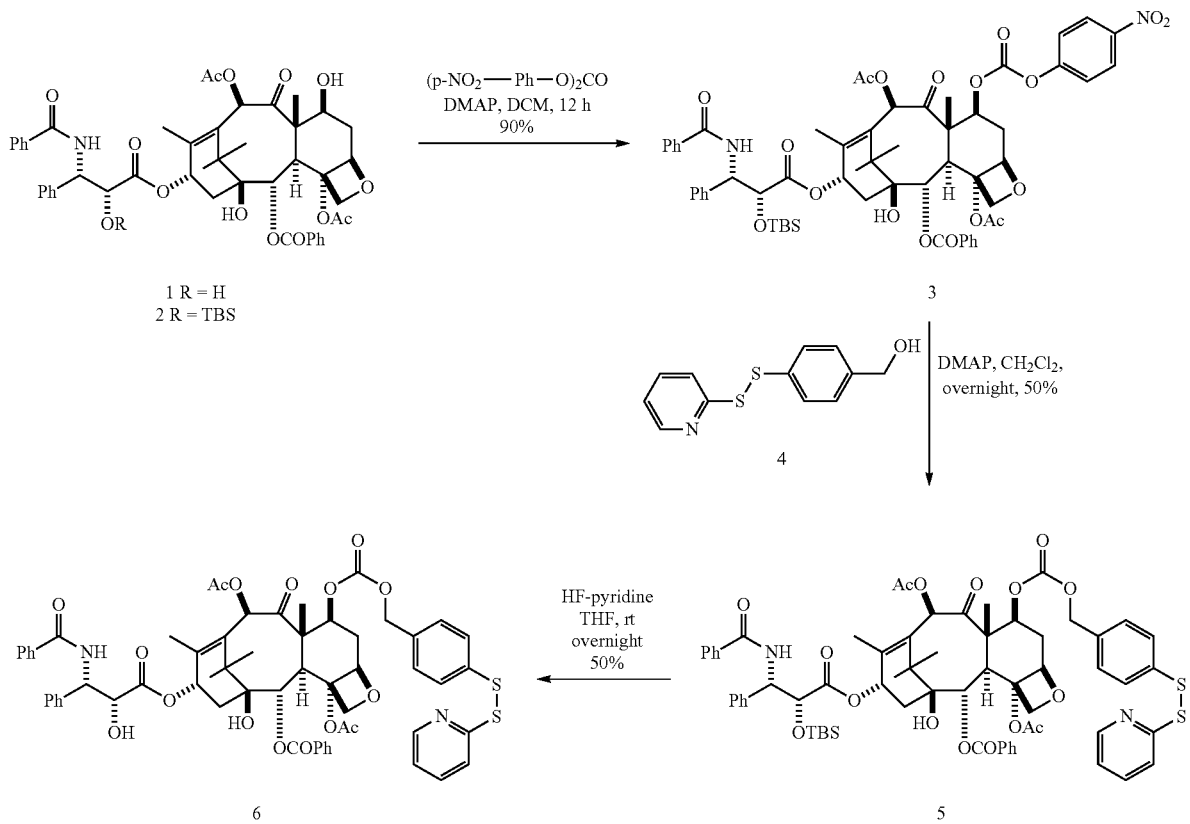

Scheme 1.1

Detailed Procedures for EXAMPLE 1.1

Synthesis of compound 3. To a solution of 2'-O-(t-butyldimethylsilyl)paclitaxel (2) (see Liu, C.; Strobl, J. S.; Bane, B.; Schilling, J. K.; McCracken, M.; Chatterjee, S. K.; Rahim-Bata, R.; Kingston, D. G. I. *J. Nat. Prod.* 2004, 67, 152-159) (66.5 mg, 68.8 μmol) and bis(4-nitrophenyl) carbonate (62.1 mg, 204.3 μmol) in dry dichloromethane (2 mL) was added 4-(dimethylamino) pyridine (25 mg, 204.8 μmol), and the mixture was stirred at room temperature for 12 h. (see Ebright, Y. W.; Chen, Y.; Kim, Y.; Ebright, R. H. *Bioconjugate Chem.* 1996, 7, 380-384.) The mixture was worked up by the standard procedure, and residue was purified by column chromatography (30% EtOAc/hexanes) to give compound 3 (70 mg, 90%): $^1$H NMR (CDCl$_3$) δ 8.27 (2H, d, J=9.2 Hz), 8.13 (2H, d, J=7.9 Hz), 7.75 (2H, d, J=7.3 Hz), 7.30-7.65 (11H, m), 7.10 (1H, d, J=9.0 Hz), 6.39 (1H, s), 6.28 (1H, dd, J=9.0, 8.7 Hz), 5.73 (1H, br d, J=7.1 Hz), 5.73 (1H, d, J=7.1 Hz), 5.57 (1H, dd, J=10.5, 7.1), 5.01 (1H, br d, J=8.7 Hz), 4.67 (1H, d, J=2.1 Hz), 4.37 (1H, d, J=8.5 Hz), 4.24 (1H, d, J=8.5 Hz), 4.00 (1H, d, J=6.7 Hz), 2.73 (1H, ddd, J=16.5, 9.4, 7.1 Hz), 2.58 (3H, s), 2.43 (1H, dd, J=13.4, 9.6 Hz), 2.20 (3H, s), 2.18 (1H, dd, J=15.4, 8.9 Hz), 2.08 (1H, ddd, J=13.4, 10.5, 1.6 Hz), 1.96 (3H, s), 1.88 (3H, s), 1.24 (3H, s), 1.19 (3H, s), 0.80 (9H, s), −0.04 (3H, s), −0.30 (3H, s); $^{13}$C NMR (CDCl$_3$) δ 201.3, 171.4, 170.1, 169.3, 167.2, 166.9, 162.0, 155.7, 151.8, 145.5, 141.4, 138.1, 134.0, 133.8, 132.7, 131.9, 130.2, 129.0, 128.8, 128.8, 128.0, 127.0, 126.4, 126.0, 125.0, 122.6, 115.5, 83.7, 80.8, 78.7, 77.1, 76.4, 75.2, 75.1, 74.4, 71.3, 60.4, 55.9, 55.7, 46.8, 43.4, 35.6, 33.2, 26.4, 25.5, 22.9, 21.5, 21.0, 20.8, 18.1, 14.6, 14.2, 10.7, −5.2, −5.8; HRFABMS m/z 1133.4362 [M+H$^+$] (calcd for C$_{60}$H$_{69}$N$_2$O$_{18}$Si, 1133.4315).

Synthesis of compound 5. To a solution of compounds 3 (36.5 mg, 32 μmol) and disulfide 4 (see Senter, P. D.; Pearce, W. E.; Greenfield, R. S. *J. Org. Chem.* 1990, 55, 2975-2978) (16 mg, 64 μmol) in dry dichloromethane (1 mL) was added 4-(dimethylamino)pyridine (11.7 mg, 96 μmol), and the mixture was stirred at room temperature for 12 h. (see Fardis, M.; Pyun, H.-J.; Tario, J.; Jin, H.; Kim, C. U.; Ruckman, J.; Lin, Y.; Green, L.; Hicke, B. Bioorg. Med. Chem. 2003, 11, 5051-5058; Liu, C.; Schilling, J. K.; Ravindra, R.; Bane, S.; Kingston, D. G. I. Bioorg. Med. Chem. 2004, 12, 6147-6161). Workup as described above and purification by column chromatography (30% EtOAc/hexanes) afforded compound 5 (20 mg, 50%): $^1$H NMR (CDCl$_3$) δ 8.46 (1H, d, J=4.9 Hz), 8.11 (2H, d, J=7.3 Hz), 7.76 (2H, d, J=7.6 Hz), 7.25-7.55 (17H, m), 7.10 (1H, d, J=8.7 Hz), 6.39 (1H, s), 6.26 (1H, dd, J=9.2, 8.1 Hz), 5.73 (1H, d, J=8.7 Hz), 5.70 (1H, br d, J=6.7 Hz), 5.54 (1H, dd, J=10.1, 6.9), 5.16 (2H, br s), 4.97 (1H, d, J=9.2 Hz), 4.67 (1H, br s), 4.34 (1H, d, J=8.5 Hz), 4.20 (1H, d, J=8.5 Hz), 3.97 (1H, d, J=6.7 Hz), 2.60 (1H, m), 2.58 (3H, s), 2.42 (1H, dd, J=15.1, 9.4 Hz), 2.15 (3H, s), 2.15 (1H, dd, J=15.4, 8.9 Hz), 2.00 (1H, m), 2.00 (3H, s), 1.80 (3H, s), 1.22 (3H, s), 1.16 (3H, s), 0.80 (9H, s), −0.03 (3H, s), −0.30 (3H, s); $^{13}$C NMR (CDCl$_3$) δ 201.6, 171.4, 170.0, 169.1, 167.1, 166.9, 159.0, 154.0, 149.0, 141.1, 138.2, 136.6, 135.7, 134.0, 133.7, 132.7, 131.8, 130.2, 129.7, 129.0, 128.8, 128.3, 128.0, 127.0, 126.3, 126.0, 121.5, 120.5, 115.7, 83.8, 80.9, 78.7, 76.3, 75.5, 75.3, 75.0, 74.4, 71.3, 69.2, 56.0, 55.7, 46.8, 43.3, 35.5, 33.3, 26.4, 25.5, 23.0, 21.4, 20.8, 18.1, 14.6, 10.7, −5.2, −5.8; HRFABMS m/z 1243.4370 [M+H$^+$] (calcd for C$_{66}$H$_{75}$N$_2$O$_{16}$S$_2$Si, 1243.4327).

Synthesis of compound 6. To a solution of compound 5 (18 mg, 14.5 μmol) in 1 mL of dried THF was added 0.1 mL of anhydrous pyridine, then the solution was cooled to 0° C. and 0.2 mL of HF-pyridine was added. The reaction mixture was allowed to warm to room temperature and for 6 h. (see Liu, C.; Strobl, J. S.; Bane, B.; Schilling, J. K.; McCracken, M.; Chatterjee, S. K.; Rahim-Bata, R.; Kingston, D. G. I. *J. Nat. Prod.* 2004, 67, 152-159.) The mixture was worked up by the standard procedure. The residue was purified by preparative TLC (50% EtOAc/hexane) to give 16 (8.2 mg, 50%): $^1$H NMR (CDCl$_3$) δ 8.46 (1H, d, J=4.9 Hz), 8.11 (2H, d, J=7.2 Hz), 7.76 (2H, d, J=8.0 Hz), 7.25-7.65 (17H, m), 7.10 (1H, br dd, J=7.0, 4.1 Hz), 7.04 (1H, d, J=8.8 Hz), 6.36 (1H, s), 6.19 (1H, dd, J=6.9, 6.9 Hz), 5.80 (1H, dd, J=8.8, 2.5 Hz), 5.67 (1H, d, J=6.8 Hz), 5.47 (1H, dd, J=10.7, 7.5), 5.17 (1H, d, J=12.3 Hz), 5.13 (1H, d, J=12.3 Hz), 4.93 (1H, d, J=8.8 Hz), 4.80 (1H, dd, J=5.0, 2.5 Hz), 4.31 (1H, d, J=8.7 Hz), 4.18 (1H, d, J=8.7 Hz), 3.93 (1H, d, J=6.8 Hz), 3.65 (1H, d, J=5.0 Hz), 2.58 (1H, m), 2.38 (3H, s), 2.33 (2H, d, J=6.9 Hz), 2.15 (3H, s), 1.95 (1H, m), 1.85 (3H, s), 1.80 (3H, s), 1.22 (3H, s), 1.17 (3H, s); $^{13}$C NMR (CDCl$_3$) δ 201.5, 172.5, 170.4, 169.0, 167.0, 166.8, 159.0, 153.8, 149.0, 140.5, 138.0, 137.8, 133.8, 133.8, 133.6, 133.0, 131.9, 130.1, 129.6, 129.0, 128.7, 128.7, 128.4, 127.7, 127.0, 127.0, 121.5, 120.5, 83.8, 80.9, 78.5, 76.4, 75.6, 75.3, 74.2, 73.1, 72.2, 69.3, 56.1, 54.9, 46.9, 43.2, 35.5, 33.4, 26.5, 22.5, 20.9, 20.8, 14.6, 10.6; HRFABMS m/z 1129.3464 [M+H$^+$] (calcd for C$_{60}$H$_{61}$N$_2$O$_{16}$S$_2$, 1129.3463).

Example 1.3

Synthesis of an M3 Type Compound of Substituent 1 (8 in this Example)

Scheme 1.3

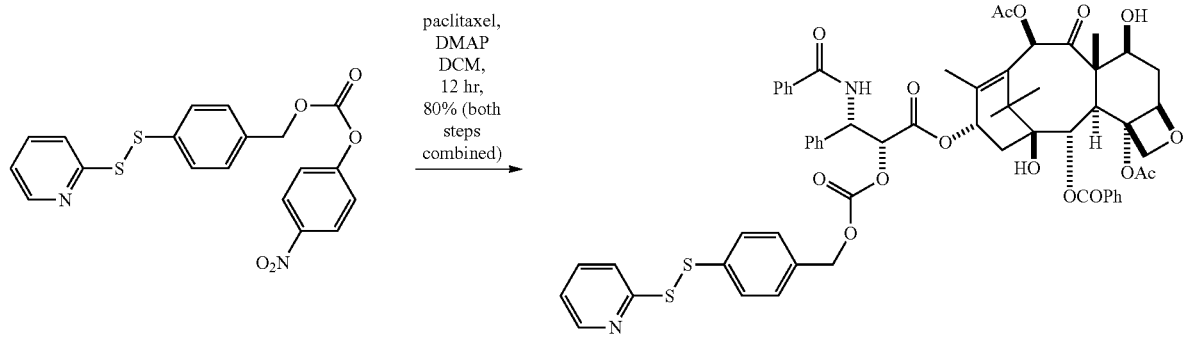

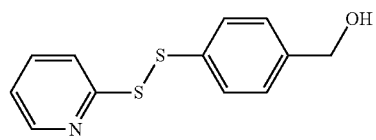

4

The carbonate 7 was prepared by reacting the disulfide 4 with bis(4-nitrophenyl) carbonate (Fardis, M.; Pyun, H.-J.; Tario, J.; Jin, H.; Kim, C. U.; Ruckman, J.; Lin, Y.; Green, L.; Hicke, B. Bioorg. Med. Chem. 2003, 11, 5051-5058.). Treatment of paclitaxel with 7 gave the M3 type paclitaxel disulfide 8 (Liu, C.; Schilling, J. K.; Ravindra, R.; Bane, S.; Kingston, D. G. I. Bioorg. Med. Chem. 2004, 12, 6147-6161.)

Synthesis of compound 8. A solution of the disulfide 4 (see Senter, P. D.; Pearce, W. E.; Greenfield, R. S. J. Org. Chem. 1990, 55, 2975-2978) (7 mg, 28 μmol in dry dichloromethane (2 mL) was added to a stirred solution of bis(4-nitrophenyl) carbonate (12.8 mg, 42 μmol) and 4-(dimethylamino) pyridine (10.3 mg, 84 μmol) in dry dichloromethane (2 mL). After being stirred at room temperature for 12 h, paclitaxel (47.8 mg, 56 μmol) was added. The reaction mixture was allowed to stir at room temperature for another 12 h (see Fardis, M.; Pyun, H.-J.; Tario, J.; Jin, H.; Kim, C. U.; Ruckman, J.; Lin, Y.; Green, L.; Hicke, B. Bioorg. Med. Chem. 2003, 11, 5051-5058; Liu, C.; Schilling, J. K.; Ravindra, R.; Bane, S.; Kingston, D. G. I. Bioorg. Med. Chem. 2004, 12, 6147-6161.) Workup as described above and purification by preparative TLC (30% EtOAc/hexanes) afforded compound 8 (25.3 mg, 80%): $^1$H NMR (CDCl$_3$). δ 8.48 (1H, d, J=4.6 Hz), 8.13 (2H, d, J=8.0 Hz), 7.71 (2H, d, J=8.3 Hz), 7.25-7.65 (17H, m), 7.13 (1H, br dd, J=5.1, 3.3 Hz), 6.88 (1H, d, J=9.2 Hz), 6.29 (2H, br s), 5.97 (1H, br d, J=9.2 Hz), 5.68 (1H, d, J=7.0 Hz), 5.42 (1H, br s), 5.13 (1H, d, J=12.3 Hz), 5.09 (1H, d, J=12.3 Hz), 4.97 (1H, d, J=9.4 Hz), 4.43 (1H, dd, J=10.6, 6.9 Hz), 4.31 (1H, d, J=8.5 Hz), 4.20 (1H, d, J=8.5 Hz), 3.80 (1H, d, J=7.0 Hz), 2.56 (1H, m), 2.44 (3H, s), 2.39 (1H, dd, J=15.4, 9.4 Hz), 2.23 (3H, s), 2.19 (1H, dd, J=15.4, 8.7 Hz), 1.91 (3H, s), 1.88 (1H, m), 1.68 (3H, s), 1.25 (3H, s), 1.13 (3H, s); $^{13}$C NMR (CDCl$_3$) δ 203.8, 171.3, 169.8, 167.8, 167.1, 167.1, 159.2, 154.0, 149.6, 142.6, 137.4, 136.6, 133.6, 133.4, 133.4, 132.8, 132.1, 130.2, 129.1, 129.1, 129.1, 128.7, 128.7, 128.5, 127.4, 127.1, 126.5, 121.1, 119.8, 84.4, 81.1, 79.2, 77.2, 76.9, 76.4, 75.6, 75.1, 72.1, 72.1, 70.0, 58.5, 52.7, 45.6, 43.2, 35.6, 35.6, 26.8, 22.7, 22.2, 20.8, 14.8, 9.6; HRFABMS m/z 1129.3433 [M+H$^+$] (calcd for C$_{60}$H$_{61}$N$_2$O$_{16}$S$_2$, 1129.3463).

Example 2.1

Synthesis of an M1 Type Compound of Substituent 2 (compound 13 in this Example)

Treatment of the commercially available PEG carboxylic acid 11 with 2,2'-pyridyl disulfide yielded compound 12 (Senter, P. D.; Pearce, W. E.; Greenfield, R. S. J Org. Chem. 1990, 55, 2975-2978; Ebright, Y. W.; Chen, Y.; Kim, Y.; Ebright, R. H. Bioconjugate Chem. 1996, 7, 380-384.) Reaction of 2'-OTBS paclitaxel (2) with chloromethyl chloroformate (Anh, D. V.; Olofson, R. A.; Wolf, P. R.; Piteau, M. D.; Senet, J. P. G. J. Org. Chem. 1990, 55, 1847-1851) yielded the 7-chloromethyl carbonate 9. Deprotection of 9 at the C2' position (Liu, C.; Strobl, J. S.; Bane, B.; Schilling, J. K.; McCracken, M.; Chatterjee, S. K.; Rahim-Bata, R.; Kingston, D. G. I. J. Nat. Prod. 2004, 67, 152-159) gave the C2' alcohol 19. Reaction of compound 10 with acid 12 in an S$_N$2 step (Lee, K. H.; Chung, Y. J.; Kim, Y. J.; Song, S. J. Bull. Korean Chem. Soc. 2005, 26, 1079-1082) gave the final product 13.

Scheme 2.1

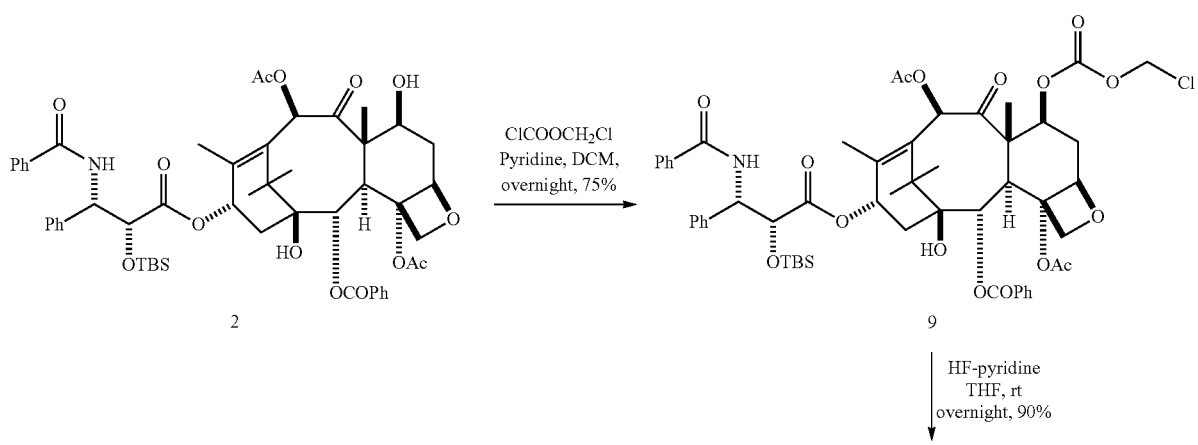

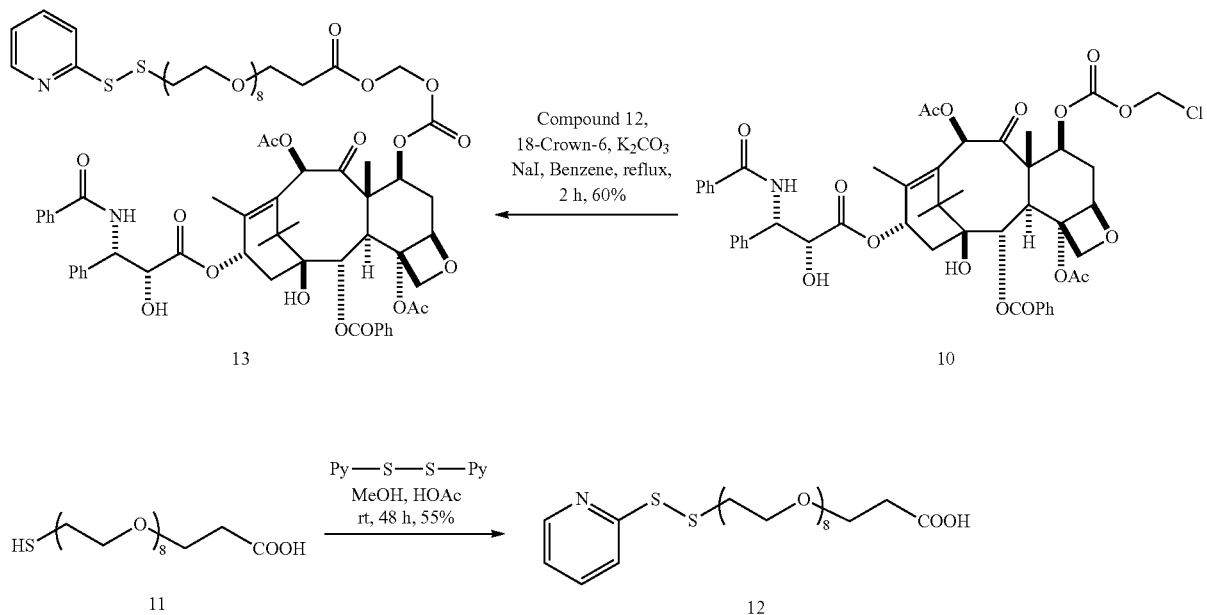

Synthesis of compound 9. To a stirred solution of chloromethyl chloroformate (2.9 mg, 22.1 μmol) and 2'-O-(t-butyldimethylsilyl)paclitaxel (2) (20 mg, 20.7 μmol) in anhydrous DCM (0.4 mL) at 0° C. was added pyridine (2.0 μL, 24.2 μmol) dropwise (see Lee, K. H.; Chung, Y. J.; Kim, Y. J.; Song, S. *J. Bull. Korean Chem. Soc.* 2005, 26, 1079-1082.) The resulting mixture was allowed to warm to room temperature and stirred for 6 h. The reaction was worked up by the standard procedure. The residue was purified by preparative TLC (50% EtOAc/hexane) to give 9 (16 mg, 74%): $^{1}$H NMR (CDCl$_3$) δ 8.12 (2H, d, J=8.5 Hz), 7.74 (2H, d, J=8.5 Hz), 7.25~7.65 (11H, m), 7.08 (1H, d, J=9.0 Hz), 6.32 (1H, s), 6.26 (1H, t, J=8.5 Hz), 5.98 (1H, d, J=6.5 Hz), 5.73 (1H, d, J=8.5 Hz), 5.69 (1H, d, J=6.5 Hz), 5.57 (1H, dd, J=10.5, 3.5 Hz), 5.51 (1H, d, J=6.5 Hz), 4.98 (1H, d, J=9.5 Hz), 4.67 (1H, d, J=2.5 Hz), 4.35 (1H, d, J=8.0 Hz), 4.20 (1H, d, J=8.5 Hz), 3.96 (1H, d, J=7.0 Hz), 2.66 (1H, m), 2.58 (3H, s), 2.41 (1H, dd, J=15, 8.5 Hz), 2.14 (3H, s), 2.04 (3H, s), 1.99 (3H, s), 1.82 (3H, s), 1.21 (3H, s), 1.15 (3H, s), 0.80 (9H, s), −0.03 (3H, s), −0.30 (3H, s); HRFABMS m/z 1060.3853 [M+H$^+$] (calcd for C$_{55}$H$_{67}$ClNO$_{16}$Si, 1060.3918).

Synthesis of compound 10. To a solution of 9 (16 mg, 13.2 μmol) in tetrahydrofuran (1.0 mL) at 0° C. was added HF-pyridine (0.2 mL) dropwise. The resulting mixture was stirred overnight. The reaction was worked up by the standard procedure. The residue was used in the next step without purification.

Synthesis of compound 12. Treatment of the commercially available PEG carboxylic acid 11 with 2,2'-pyridyl disulfide yielded compound 12 (Senter, P. D.; Pearce, W. E.; Greenfield, R. S. *J. Org. Chem.* 1990, 55, 2975-2978; Ebright, Y. W.; Chen, Y.; Kim, Y.; Ebright, R. H. *Bioconjugate Chem.* 1996, 7, 380-384.)

Synthesis of compound 13. To a solution of 10 (16.0 mg, 27.7 μmol) in benzene (0.4 mL) was added 18-crown-6 (23.6 mg, 89.2 μmol) and K$_2$CO$_3$ (7.6 mg, 55.4 μmol). The resulting mixture was stirred for 30 min. Compound 12 (16.0 mg, 16.9 μmol) and NaI (5.0 mg, 33.8 μmol) were then added and the resulting mixture was stirred under reflux for additional 2 hours. (see Lee, K. H.; Chung, Y. J.; Kim, Y. J.; Song, S. *J. Bull. Korean Chem. Soc.* 2005, 26, 1079-1082.) The solution was allowed to cool down to room temperature and the solvent was evaporated under N$_2$. The residue was purified by preparative TLC (10% methanol/dichloromethane) to give 13 (15 mg, 60%): $^{1}$H NMR (CDCl$_3$) δ 8.44 (1H, d, J=4.8 Hz), 8.11 (2H, d, J=7.6 Hz), 7.25~7.80 (15H, m), 7.10 (2H, m), 6.30 (1H, s), 6.18 (1H, dd, J=8.0, 8.0 Hz), 5.90 (1H, d, J=6.0 Hz), 5.79 (1H, dd, J=9.2, 2.4 Hz), 5.71 (1H, d, J=6.0 Hz), 5.67 (1H, d, J=6.8 Hz), 5.48 (1H, dd, J=10.8, 6.8 Hz), 5.30 (1H, s), 4.94 (1H, d, J=8.4 Hz), 4.80 (1H, dd, J=6.4, 4.0 Hz), 4.31 (1H, d, J=8.4 Hz), 4.19 (1H, d, J=7.6 Hz), 3.91 (1H, d, J=6.8 Hz), 3.55~3.80 (33H, m), 2.99 (2H, dd, J=6.4, 6.4 Hz), 2.67 (2H, dd, J=6.4, 6.4 Hz), 2.64 (1H, m), 2.38 (3H, s), 2.32 (2H, d, J=9.2 Hz), 2.16 (3H, s), 2.01 (1H, m), 1.85 (3H, s), 1.80 (3H, s), 1.21 (3H, s), 1.16 (3H, s); $^{13}$C NMR (CDCl$_3$) δ 201.4, 172.6, 170.5, 170.1, 169.1, 167.0, 166.8, 153.3, 149.6, 140.7, 138.1, 137.2, 133.9, 133.0, 132.0, 130.3, 129.1, 129.1, 128.8, 128.8, 128.4, 127.1, 127.1, 120.7, 119.7, 84.5, 83.8, 82.6, 81.2, 81.0, 79.2, 78.7, 76.5, 76.2, 75.7, 75.4, 74.3, 73.2, 72.5, 72.2, 70.6, 70.5, 69.0, 66.1, 65.5, 56.2, 54.9, 47.0, 43.3, 38.5, 35.6, 34.8, 33.4, 29.8, 27.0, 26.6, 22.6, 21.0, 20.8, 14.8, 10.7; HRFABMS m/z 1477.5421 [M+H$^+$] (calcd for C$_{73}$H$_{93}$N$_2$O$_{26}$S$_2$, 1477.5458).

Example 2A
Synthesis of an M2 Type Compound of Substituent 2 (Compound 2C in this Hypothetical Example)
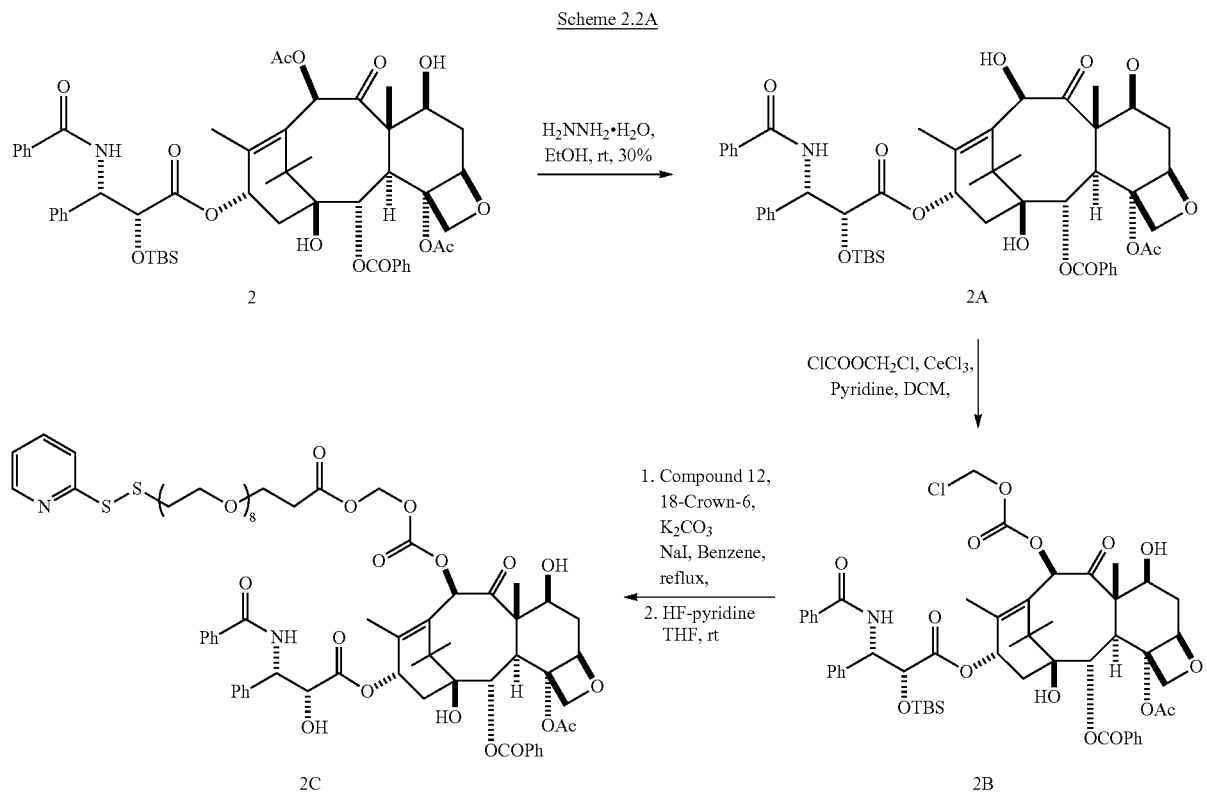
Example 3.3
Synthesis of an M3 Type Compound of Substituent 3 (22 in Scheme 3)
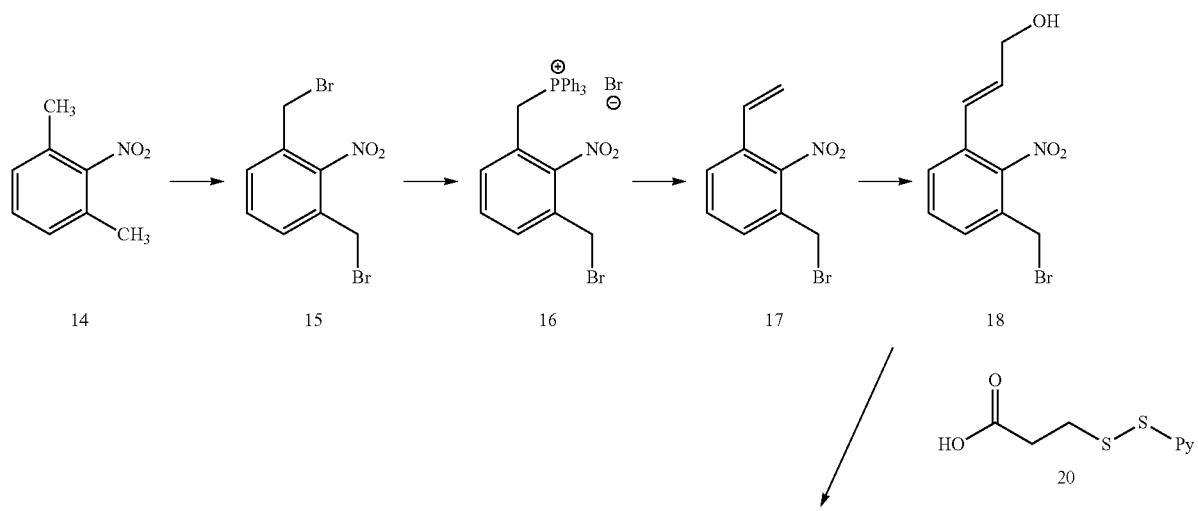

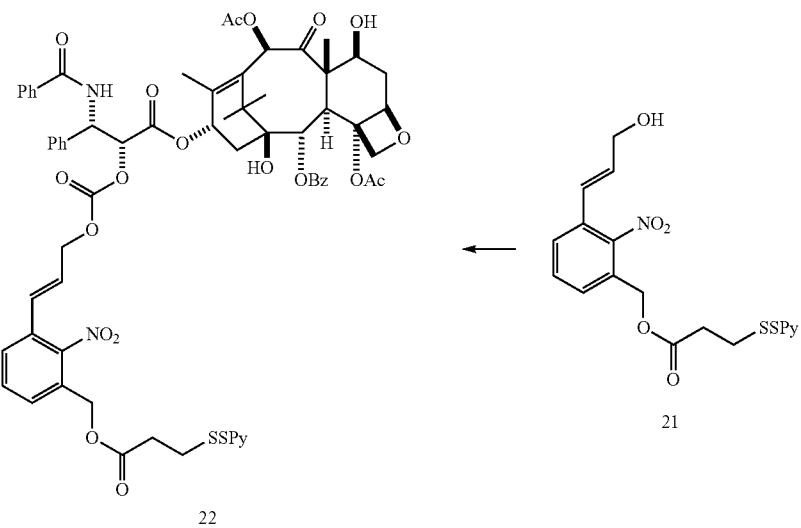
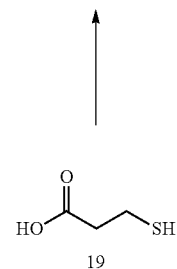

1,3-Bis-bromomethyl-2-nitro-benzene (15) The commercially available 2-nitro-m-xylene (14) (600 mg, 542 μL, 4.0 mmol) was treated with CCl₄ (10 mL), N-bromosuccinimide (1.4 g, 7.9 mmol), and benzoyl peroxide (192.3 mg, 0.8 mmol) and the resulting reaction mixture was refluxed at 80° C. for 18 h with stirring. The reaction progress was followed by TLC. Upon cooling of the reaction mixture, the solvent was evaporated under reduced pressure. The residue was purified by FCC (20% EtOAc/hexane) to yield 15 as a solid (374.6 mg, 30.1%). NMR (500 MHz, CDCl₃): δ7.51 (3H, m), 4.50 (4H, s); $^{13}$C NMR δ 132.0, 131.7, 131.0, 26.7.

(3-Bromomethyl-2-nitrobenzyl)-triphenylphosphonium bromide (16) To a solution of 15 (1.9 g, 6.2 mmol), accumulated from multiple reactions, in anhydrous benzene (25 mL) was added a triphenylphosphine (1.9 g, 7.4 mmol)/benzene (25 mL) solution. The reaction mixture was refluxed at 80° C. for 18 h. Upon cooling, Et₂O (30 mL) was added and the solvents decanted. The residue was subjected to reduced pressure for removal of remaining solvent, and was purified by FCC (10% MeOH/CH₂Cl₂) to yield 16 as a solid (1.5 g, 42.4%). NMR (400 MHz, CDCl₃): δ 7.62 (18H, m), 5.54 (2H, s), 4.35 (2H, s); $^{13}$C NMR: δ 135.5 (×2), 134.6, 134.4, 130.7, 130.6, 27.5.

1-Bromomethyl-2-nitro-3-vinyl-benzene (17) Ylide 16 (1.5 g, 2.4 mmol) in 95% EtOH (14 mL) was treated with a solution of CH₂O (2.0 mL, 73.5 mmol), KOH (294.7 mg, 5.3 mmol), and EtOH (14 mL). The reaction mixture was stirred at rt for 36 min. The reaction mixture was quenched with deionized (DI) H₂O (15.0 mL) and the crude extracted with CH₂Cl₂ (3×20.0 mL). The organic layer was washed with DI H₂O (20.0 mL), dried over anhydrous Na₂SO₄, and concentrated under reduced pressure. FCC (20% EtOAc in hexane) yielded compound 17 (281.2 mg, 44.2%) as a pale yellow solid. NMR (500 MHz, CDCl₃): δ 7.59 (1H, d, J=7.4), 7.46 (2H, m), 6.65 (1H, m), 5.83 (1H, d, J=17.3), 5.50 (1H, d, J=11.0), 5.30 (2H, s); $^{13}$C NMR: δ 131.2, 131.1, 130.7, 129.9, 129.8, 127.4, 120.4, 26.7.

(E)-3-(3-Bromomethyl-2-nitrophenyl)prop-2-en-1-ol (18) To 2$^{nd}$ generation Grubbs catalyst (18.5 mg, 0.02 mmol) in CH₂Cl₂ (0.75 mL) under N₂, was added 17 (188.9 mg, 0.8 mmol) in CH₂Cl₂ (0.75 mL), and 2-butene-1,4-diol (128.3 μL, 1.6 mmol). The reaction mixture was heated to 35° C. under N₂ for 17 h. The cooled reaction mixture was concentrated under reduce pressure. FCC of the crude product on silica gel with 20% to 40% EtOAc in hexane yielded compound 18 (62.5 mg, 29.6%) as a tan solid. $^{1}$H NMR (400 MHz, CDCl₃): δ 7.57 (1H, d, J=7.3), 7.44 (2H, m), 6.57 (1H, d, J=15.9), 6.44 (1H, m), 4.46 (2H, s), 4.35 (2H, d, J=4.8); $^{13}$C NMR: δ 135.4, 131.0, 130.5, 130.0, 127.7, 122.9, 63.3, 26.7.

3-(Pyridin-2-yldisulfanyl)propionic acid (20). Dithiodipyridine (1.9 g, 8.5 mmol) in an EtOH:AcOH mixture (10 mL: 15 mL), stirring vigorously, was treated with 3-mercaptopropionic acid 19 (368.9 μL, 4.2 mmol) in EtOH (10 mL) over a 15 min period. The reaction mixture was stirred for 2.5 h, and then concentrated under reduced pressure. FCC of the crude product on silica gel (2.5% to 50% EtOH in CH₂Cl₂) yielded compound 15 (545.3 mg, 56.1%) as a pale yellow solid; $^{1}$H NMR (500 MHz, CDCl₃): δ 10.47 (1H, bs), 8.49 (1H, d, J=5.1), 7.68 (2H, m), 7.15 (1H, m), 3.06 (2H, t, J=7.0), 2.81 (2H, t, J=7.0); $^{13}$C NMR: δ 176.0, 159.6, 149.5, 137.7, 121.3, 120.6, 34.1, 33.8; HRFABMS m/z 216.0150 (−1.6 ppm/−0.3 mmu) [M+H⁺] (calcd for C₈H₁₀NO₂S₂, 216.0153).

3-((E)-3-hydroxyprop-1-enyl)-2-nitrobenzyl 3-(pyridin-2-yldisulfanyl)-propionate (21). To acid 20 (40.0 mg, 0.18 mmol) in benzene (0.3 mL) was added 18-crown-6 (48.0 mg, 0.18 mmol) and K₂CO₃ (23.1 mg, 0.18 mmol). The mixture was stirred for 1 h and alcohol 18 (41.0 mg, 0.15 mmol) was added followed by NaI (27.2 mg, 0.18 mmol). The reaction mixture was heated to 50° C. for 3 h, and then cooled. The mixture was diluted with CH₂Cl₂ (1.0 mL), washed with saturated NaHCO₃ solution (3.0 mL), extracted with CH₂Cl₂ (3×3.0 mL), drying over anhydrous Na₂SO₄, and concentration under reduced pressure. FCC on silica gel with 40% EtOAc in hexane yielded ester 21 (41.8 mg, 68.0%) as a cream oil. $^{1}$H NMR (400 MHz, CDCl₃): δ 8.44 (1H, s), 7.62 (3H, m), 7.46 (1H, m), 7.37 (1H, m), 7.09 (1H, t, J=5.2), 6.59 (1H, d, J=15.7), 6.42 (1H, m), 5.16 (2H, d, J=3.8), 4.34 (2H, m), 3.03 (2H, t, J=7.1), 2.80 (2H, t, J=7.0), 2.03 (1H, bs); $^{13}$C NMR: δ 171.6, 159.7, 150.0, 149.6, 148.8, 135.3, 131.1, 130.6, 130.3, 129.3, 128.8, 128.2, 121.3, 120.7, 62.5, 34.1, 33.7, 33.2; HRFABMS m/z 407.0741 (+1.4 ppm/+0.6 mmu) [M+H⁺] (calcd for C₁₈H₁₉N₂O₅S₂, 407.0735).

Compound 22. Ester 21 (42.3 mg, 0.10 mmol), DMAP (catalytic amount), and 4-nitrophenyl chloroformate (18.9 mg, 0.09 mmol) in $CH_2Cl_2$ (3.4 mL) under $N_2$ were treated with pyridine (10.1 µL, 0.12 mmol). The reaction mixture was stirred at rt for 20 h. Paclitaxel (71.2 mg, 0.08 mmol) and DMAP (14.0 mg, 0.11 mmol) were added and the reaction mixture was stirred at it for an additional 75 h. The reaction mixture was diluted with EtOAc (5 mL), washed with saturated $NaHCO_3$ solution (10 mL), DI $H_2O$ (10 mL), 0.5 N $Na_2SO_4$ (10 mL), and brine (10 mL). The organic layer was dried over anhydrous $Na_2SO_4$ and concentrated under reduced pressure. FCC on silica gel with 40% to 60% EtOAc in hexane yielded compound 3 (49.9 mg, 37.3%) as a white solid; $^1$H NMR (400 MHz, $CDCl_3$): δ 4.6 (1H, s), 8.15 (2H, d, J=7.1), 7.75 (2H, d, J=6.9), 7.64 (4H, m), 7.45 (13H, m), 7.09 (1H, t, J=6.0), 6.95 (1H, d, J=9.5), 6.65 (1H, d, J=16.1), 6.29 (2H, m), 5.99 (1H, m), 5.69 (1H, d, J=7.3), 5.44 (1H, d, J=2.8), 5.18 (2H, d, J=10.3), 4.98 (1H, d, J=8.9), 4.80 (1H, t, J=4.6), 4.69 (1H, t, J=5.6), 4.44 (1H, m), 4.33 (1H, d, J=8.5), 4.21 (1H, d, J=8.3), 3.82 (1H, d, J=7.1), 3.03 (2H, t, J=7.1), 2.81 (2H, t, J=6.9), 2.47 (6H, m), 2.23 (3H, m), 1.94 (1H, m), 1.77 (1H, m), 1.69 (3H, s), 1.63 (3H, s), 1.24 (3H, s), 1.14 (3H, s); $^{13}$C NMR: δ 204.0, 171.5, 171.1, 170.1, 168.0, 167.2, 159.7, 154.0, 150.0, 142.9, 136.8, 133.6, 133.0 (×2), 130.5, 130.3, 129.3, 128.9, 128.7, 128.4, 128.3, 128.2, 127.5, 127.2, 126.3, 121.5, 120.6, 85.4, 85.0, 81.3, 79.4, 75.9, 75.6, 75.0, 72.4, 62.4, 58.7, 52.9, 45.6, 43.4, 35.8, 33.7, 33.2, 27.0, 23.1, 22.3, 21.0, 15.1, 15.0; HRFABMS m/z 1286.3853 (+1.2 ppm/+1.5 mmu) [M+H$^+$] (calcd for $C_{66}H_{68}N_3O_{20}S_2$, 1286.3838).

Example 3.1

Synthesis of an M1 Type Compound of Substituent 3, Compound 23 in this Scheme

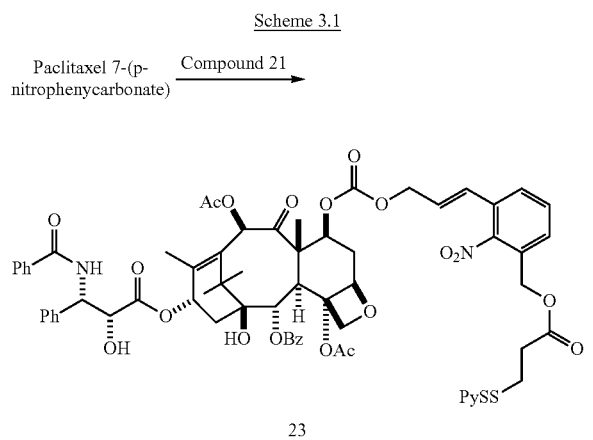

Compound 23. Compound 23 could be prepared by reaction of compound 21 with paclitaxel 7-(p-nitrophenylcarbonate).

Example 4.3

Synthesis of an M3 Type Compound of Substituent 4 (24 in Scheme 4)

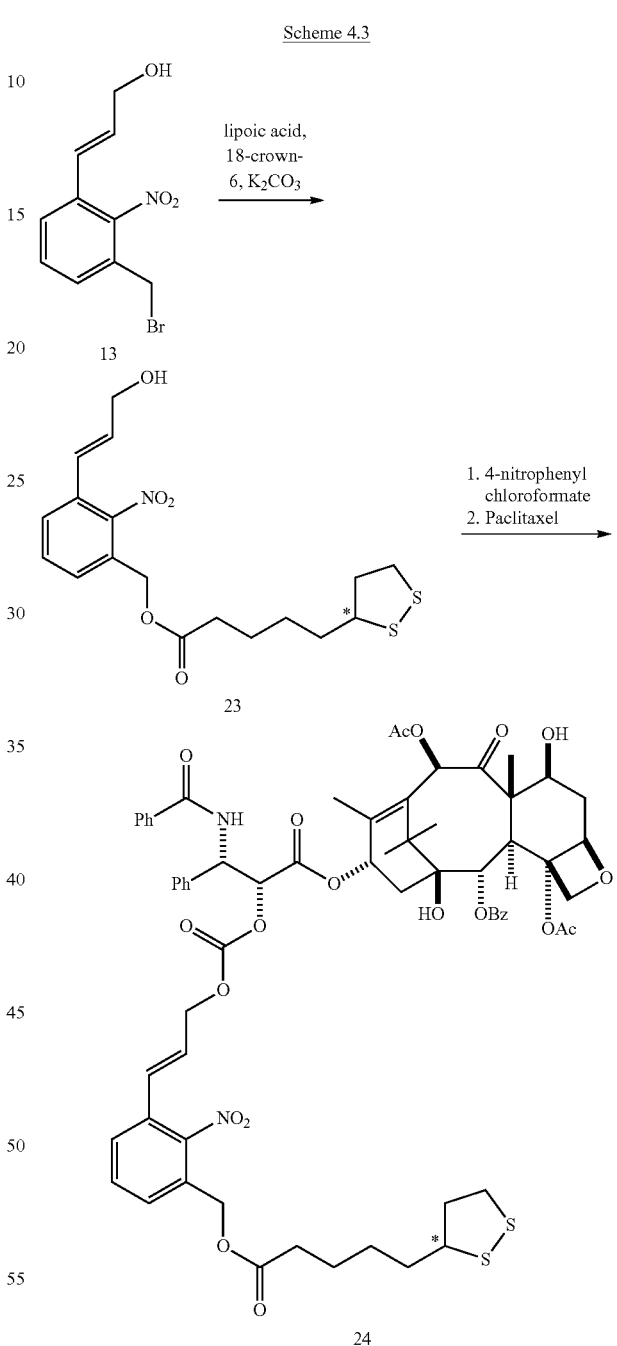

Compound 23. Compound 23 could be prepared by reaction of lipoic acid (either R/S, R, or S) with (E)-3-(3-bromomethyl-2-nitrophenyl)prop-2-en-1-ol (18) as described above for the reaction of 3-(pyridin-2-yldisulfanyl)propionic acid with 18.

Compound 24. Compound 24 could be prepared by reaction of compound 23 with paclitaxel as described above for the reaction of ester 21 with paclitaxel.

Example 4.1

Synthesis of an M1 Type Compound of Substituent 4, 23 in this Scheme

Scheme 4.1

Paclitaxel 7-(p-nitrophenycarbonate) —Compound 23→

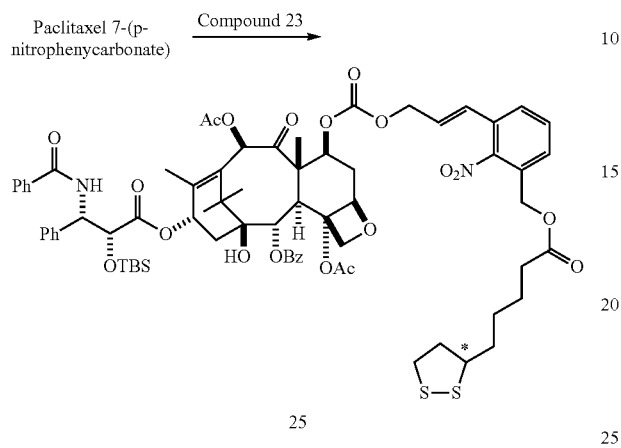

25

Compound 25. Compound 25 could be prepared by reaction of compound 23 with paclitaxel 7-(p-nitrophenylcarbonate).

Example 5.1

Synthesis of an M1 Type Compound of Substituent 5, 5.1B in this Scheme

Scheme 5.1

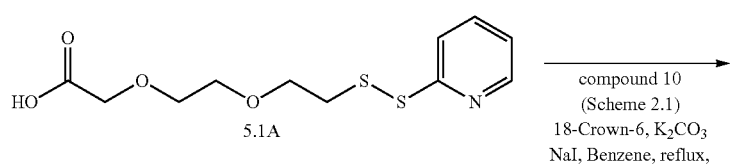

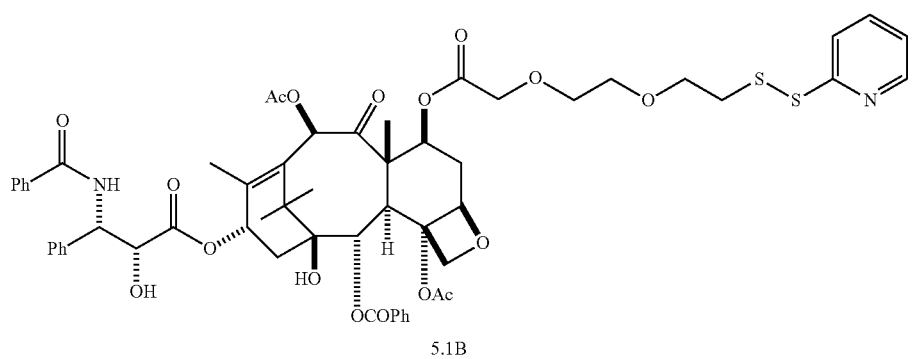

5.1B

[2-[2-(Pyridin-2-yldisulfanyl)ethoxy]ethoxy]acetic acid (5.1A) can be made by the procedure described in Frisch, B.; Boeckler, C.; Schuber, F. Synthesis of Short Polyoxyethylene-Based Heterobifunctional Cross-Linking Reagents. Application to the Coupling of Peptides to Liposomes. *Bioconjugate Chemistry*, 1996, 7, 180-186. Coupling to compound 10 (Scheme 2.1) as described for the synthesis of 13 will yield 5.1B.

Example 5.2
Synthesis of an M2 Type Compound of Substituent 5, 5.2B in this Scheme
Scheme 5.2
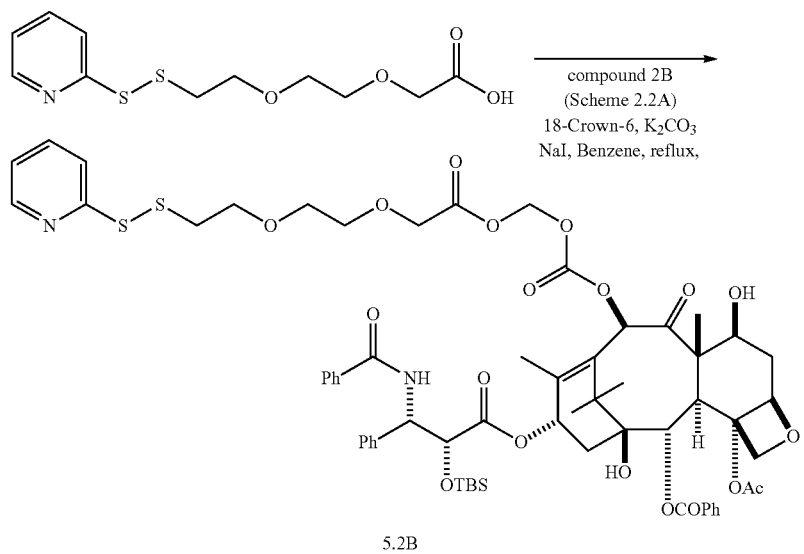
Coupling of [2-[2-(Pyridin-2-yldisulfanyl)ethoxy]ethoxy] acetic acid (5.1A) to compound 2B (Scheme 2.2A) as described for the synthesis of 2C will yield 5.2B
Example 6.1
Synthesis of an M1 Type Compound of Substituent 6, 28 in Scheme 6.1
Scheme 6.1
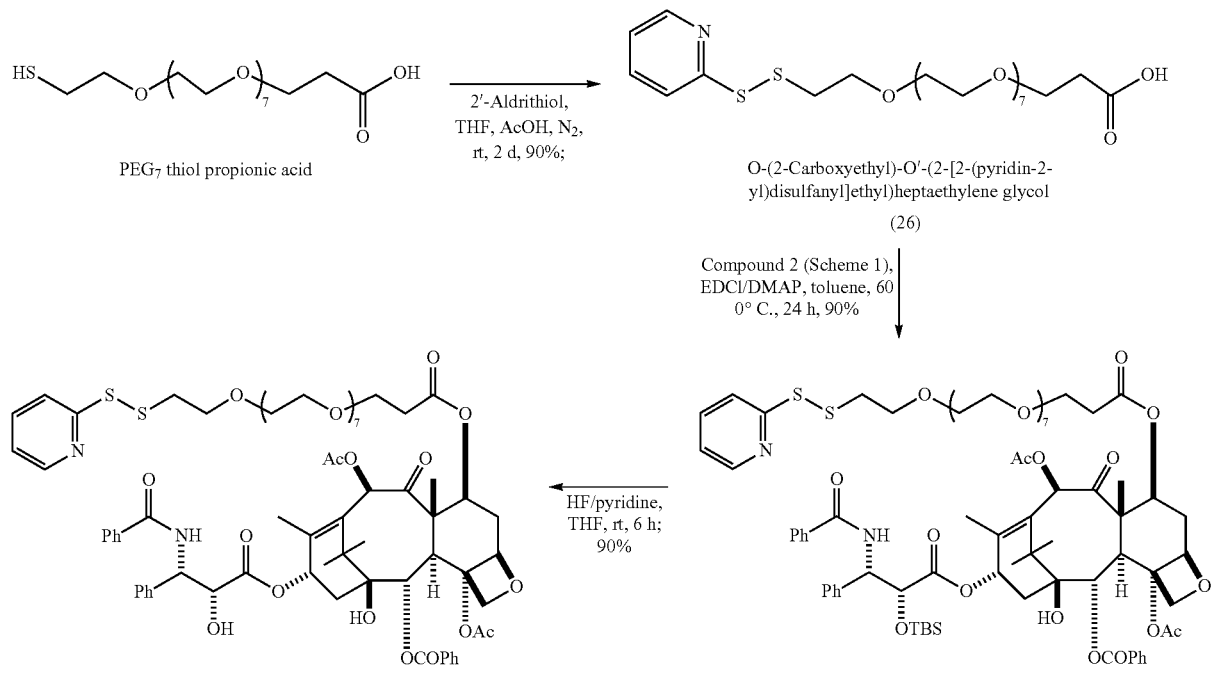

O-(2-Carboxyethyl)-O'-(2-[2-(pyridin-2-yl)disulfanyl]ethyl)heptaethylene glycol (26): To an oven dried three-necked flask under nitrogen at RT equipped with a stir bar was added 2'-Aldrithiol (0.471 g, 2.14 mmol) in 5 mL THF and 0.5 mL AcOH purged with nitrogen. To this mixture was added dropwise O-(2-carboxyethyl)-O'-(2-mercaptoethyl)heptaethylene glycol (PEG$_7$ thiol propionic acid, MW: 458; MF: $C_{19}H_{38}O_{10}S$) (0.49 g, 1.07 mmol). The solution turned yellow and was allowed to stir for two days. The solvent was then removed in vacuo and thin layer chromatography was performed using 73% ethyl acetate and hexanes. The product was a yellow solid (0.546 g, 0.96 mmol, 90% yield) and homogeneous (one spot) by TLC ($R_f$=0.2, 73% EtOAc/hexanes). (Modified method from Jones, L. R.; Goun, Elena A.; Shinde, R.; Rothbard, J. B.; Contag, C. H.; Wender, P. A. *J. Am. Chem. Soc.* 2006, 128, 6526-6527.) $^1$H NMR $\delta_H$ 8.44 (1H, d, J=4.8 Hz), 7.77 (1H, d, J=8.0 Hz), 7.65 (1H, t, J=8.0 Hz), 7.07 (1H, dd, J=8.0, 4.8 Hz), 3.50~3.80 (32H, m), 2.96 (1H, t, J=7.0 Hz), 2.60 (1H, t, J=5.2 Hz); $\delta_C$ 174.7, 160.2, 149.2, 137.3, 120.6, 119.6, 70.2~70.5, 68.7, 66.4, 38.3, 34.8.

2'-O-tertButyldimethylsilyl-7-{O-(2-carbonylethyl)-0'-(2-[2-(pyridin-2-yl)disulfanyl]ethyl)heptaethylene glycol}-paclitaxel (27): To a solution of 2 (MW: 967, MF: $C_{53}H_{65}NO_{14}S$; 30 mg, 31.0 μmol) in 5 mL of toluene was added EDCI (6.0 mg, 31 μmol). After 15 min stirring, DMAP (2 mg, cat.) was added and stirring continued for 5 min before SC201-173-2a (MW: 567, MF: $C_{24}H_{41}NO_{10}S_2$; 35.2 mg, 62 μmol) was added. The reaction mixture was allowed to stir at 60° C. for 24 h. Then, 5 mL of EtOAc was added to the reaction mixture, and the organic phase was washed with sodium bicarbonate, water, and brine, dried over sodium sulfate, and concentrated in a vacuum. The residue was applied to preparative TLC ($R_f$=0.28, 8/3 EtOAc/hexane) to give 27 (42.3 mg, 90%) (Reference: Liu, C.; Strobl, J. S.; Bane, S.; Schilling, J. K.; McCracken, M.; Chatterjee, S. K.; Rahim-Bata, R.; Kingston, D. G. I. *J. Nat. Prod.* 2004, 67, 152-159.) $^1$H NMR $\delta_H$ 8.44 (1H, br d, J=4.0 Hz), 8.12 (2H, d, J=7.8 Hz), 7.77 (1H, d, J=7.7 Hz), 7.77 (2H, d, J=7.7 Hz), 7.65 (1H, t, J=8.0 Hz), 7.61 (1H, t, J=8.0 Hz), 7.51 (3H, m), 7.39 (7H, m), 7.07 (2H, m), 6.24 (2H, m), 5.70 (2H, m), 5.62 (1H, d, J=6.8 Hz), 4.96 (1H, d, J=8.5 Hz), 4.66 (1H, br s), 4.33 (1H, d, J=8.6 Hz), 4.19 (1H, d, J=8.6 Hz), 3.95 (1H, d, J=6.7 Hz), 3.50~3.75 (34H, m), 2.98 (2H, t, J=6.4 Hz), 2.56 (3H, s), 2.13 (3H, s), 1.96 (3H, s), 1.80 (3H, s), 1.10~2.70 (6H, m), 1.20 (3H, s), 1.15 (3H, s), 0.79 (9H, s), −0.04 (3H, s), −0.32 (3H, s); $\delta_C$ 201.9, 171.4, 170.7, 168.9, 168.9, 166.9, 160.4, 149.5, 140.9, 138.2, 137.1, 134.1, 133.7, 132.6. 131.7, 130.2, 128.7~129.0, 127.9, 127.0, 126.3, 120.6, 119.6, 83.9, 80.9, 78.6, 75.3, 75.0, 74.4, 71.2, 70.4~70.6, 70.2, 68.9, 66.4, 56.0, 55.6, 46.8, 43.3, 38.4, 35.5, 34.8, 33.3, 26.3, 25.5, 23.5, 23.0, 21.3, 20.7, 14.6, 10.8, −5.2, −5.9; HRFABMS m/z 1517.6327 [M+H$^+$] (calcd for $C_{77}H_{105}N_2O_{23}S_2Si$, 1517.6319).

7-{O-(2-carbonylethyl)-O'-(2-[2-(pyridin-2-yl)disulfanyl]ethyl)heptaethylene glycol}-paclitaxel (28): To a solution of 27 (10 mg, 6.6 μmmol), in 2 mL of dried THF, was added 0.1 mL of anhydrous pyridine, then the solution was cooled to 0° C., and 0.2 mL of HF-pyridine was added. The reaction mixture was allowed to warm to RT and stirred for 6 h (not overnight). The reaction mixture was then diluted with EtOAc, and the organic phase was washed with sodium bicarbonate, water, and brine, dried over sodium sulfate, and concentrated in a vacuum. The residue was purified by preparative TLC ($R_f$=0.48, 90%, EtOAc:MeOH) to give SC201-147-2b (8.3 mg, 90%). (Reference: Liu, C.; Strobl, J. S.; Bane, S.; Schilling, J. K.; McCracken, M.; Chatterjee, S. K.; Rahim-Bata, R.; Kingston, D. G. I. *J. Nat. Prod.* 2004, 67, 152-159.) $^1$H NMR $\delta_H$ 8.43 (1H, br d, J=4.8 Hz), 8.10 (2H, d, J=7.8 Hz), 7.77 (2H, d, J=7.7 Hz), 7.77 (1H, d, J=7.7 Hz), 7.66 (1H, t, J=8.0 Hz), 7.61 (1H, t, J=8.0 Hz), 7.49 (3H, m), 7.40 (7H, m), 7.07 (1H, dd, J=7.6, 7.2 Hz), 6.20 (1H, s), 6.16 (1H, t, J=8.4 Hz), 5.79 (1H, br d, J=8.8 Hz), 5.65 (1H, d, J=6.8 Hz), 5.56 (1H, dd, J=8.0, 7.0 Hz), 4.92 (1H, d, J=9.2 Hz), 4.79 (1H, br s), 4.30 (1H, d, J=8.4 Hz), 4.17 (1H, d, J=8.4 Hz), 3.90 (1H, d, J=6.8 Hz), 3.50~3.75 (34H, m), 2.98 (2H, t, J=6.4 Hz), 2.37 (3H, s), 2.14 (3H, s), 1.81 (3H, s), 1.80 (3H, s), 1.20~2.80 (6H, m), 1.19 (3H, s), 1.15 (3H, s); $^{13}$C NMR $\delta_C$ 201.8, 172.4, 170.8, 170.3, 168.9, 166.9, 160.4, 149.5, 140.4, 138.1, 137.2, 133.8, 133.7, 132.9. 131.9, 130.2, 128.4~129.1, 128.3, 127.1, 127.1, 120.6, 119.6, 83.9, 81.0, 78.5, 76.4, 75.3, 74.3, 73.2, 72.1, 71.3, 70.2~70.6, 68.9, 66.4, 56.2, 54.9, 47.0, 43.2, 38.4, 35.5, 34.8, 34.4, 26.5, 22.6, 20.8, 14.7, 10.8; HRFABMS m/z 1403.5458 [M+H$^+$] (calcd for $C_{71}H_{91}N_2O_{23}S_2$, 1403.5454).

Example 6.2

Synthesis of an M2 Type Compound of Substituent 6, 31 in Scheme 6.2

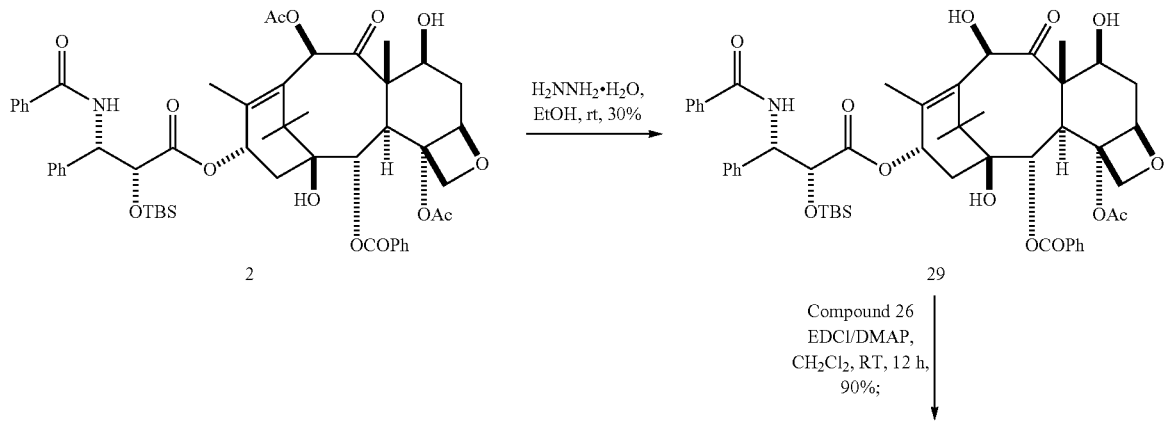

Scheme 6.2

-continued

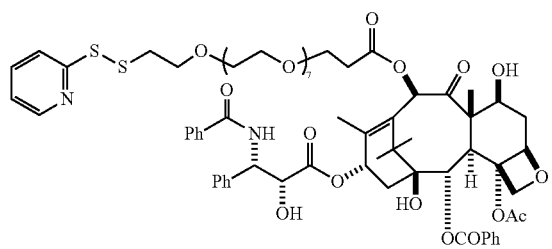

31

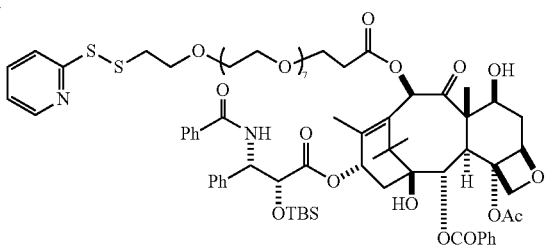

30

HF/
pyridine,
THF,
RT, 6 h;
90%

2'-TBS-10-deacetylpaclitaxel (29): Prepared as previously described: Liu, C.;. Strobl, J. S.; Bane, S.; Schilling, J. K.; McCracken, M.; Chatterjee, S. K.; Rahim-Bata, R.; Kingston, D. G. I. *J. Nat. Prod.* 2004, 67, 152-159.

Ester 30: To a solution of 29 (MW: 925, MF: $C_{51}H_{63}NO_{13}Si$; 14 mg, 15.1 μmol) in 2 mL of $CH_2Cl_2$ was added EDCI (2.9 mg, 15.1 μmol). After 15 min stirring, DMAP (2 mg, cat.) was added and stirring continued for 5 min before 26 (MW: 567, MF: $C_{24}H_{41}NO_{10}S_2$; 13 mg, 23.0 μmol) was added. The reaction mixture was allowed to stir at rt overnight. Then, 5 mL of $CH_2Cl_2$ was added to the reaction mixture, and the organic phase was washed with sodium bicarbonate, water, and brine, dried over sodium sulfate, and concentrated in a vacuum. The residue was applied to preparative TLC ($R_f$=0.3, 2/10 EtOAc/$CH_2Cl_2$) to give 30 (20.6 mg, 90%) NMR $\delta_H$ 8.43 (1H, br d, J=4.0 Hz), 8.15 (2H, d, J=7.8 Hz), 7.76 (1H, d, J=7.7 Hz), 7.71 (2H, d, J=7.7 Hz), 7.65 (1H, t, J=8.0 Hz), 7.60 (1H, t, J=8.0 Hz), 7.51 (3H, m), 7.39 (7H, m), 7.07 (1H, br t, J=7.0 Hz), 6.81 (1H, s), 6.26 (1H, t, J=8.4 Hz), 5.73 (1H, d, J=7.6 Hz), 4.93 (1H, dd, J=8.0, 7.0 Hz), 4.70, 4.63 (1H, d, J=2.0 Hz), 4.40, 4.20, 3.50~3.90, 2.97 (2H, t, J=6.4 Hz), 2.64 (3H, s), 1.86 (3H, s), 1.65 (3H, s), 0.80~2.80 (6H, m), -1.10 (3H, s), -1.20 (3H, s), 0.76 (9H, s), -0.06 (3H, s), -0.32 (3H, s); $\delta_C$ 202.0, 172.2, 171.0, 169.8, 167.1, 166.8, 160.4, 149.5, 140.2, 138.2, 137.1, 134.0, 133.5, 132.9, 131.8, 130.2, 129.2 128.7~129.0, 128.0, 127.5, 127.0, 126.3, 120.6, 119.6, 82.7, 82.1, 79.1, 75.8, 75.3, 71.0, 70.4~70.6, 68.9, 66.5, 57.7, 55.5, 42.5, 42.0, 40.3, 38.3, 36.2, 35.3, 34.9, 30.0, 25.9, 25.5, 23.5, 22.9, 21.6, 18.1, 16.2, 14.9, -5.3, -5.9; HRFABMS m/z 1475.6213 [M+H$^+$] (calcd for $C_{75}H_{103}N_2O_{22}S_2Si$, 1475.6213).

Compound 31: To a solution of 30 (10 mg, 6.6 μmol), in 1.0 mL of dried THF, was added 0.1 mL of anhydrous pyridine, then the solution was cooled to 0° C., and 0.2 mL of HF-pyridine was added. The reaction mixture was allowed to warm to RT and stirred for 6 h (not overnight). The reaction mixture was then diluted with EtOAc, and the organic phase was washed with sodium bicarbonate, water, and brine, dried over sodium sulfate, and concentrated in a vacuum. The residue was purified by preparative TLC ($R_f$=0.52, 50%, EtOAc: THF) to give SC201-147-2b (8.3 mg, 90%). 31: $\delta_H$ 8.47 (1H, br s), 8.16 (2H, d, J=7.2 Hz), 7.79 (1H, d, J=7.7 Hz), 7.77 (2H, d, J=7.7 Hz), 7.67 (1H, t, J=8.0 Hz), 7.61 (1H, t, J=8.0 Hz), 7.49 (3H, m), 7.40 (7H, m), 7.09 (1H, dd, J=7.6, 7.2 Hz), 6.80 (1H, s), 6.21 (1H, t, J=8.4 Hz), 5.79 (1H, br d, J=9.0 Hz), 5.73 (1H, d, J=7.6 Hz), 4.90 (1H, dd, J=8.0, 7.0 Hz), 4.81 (1H, br s), 4.68, 4.47, 4.37, 3.45~3.95, 2.97 (2H, t, J=6.4 Hz), 2.51 (3H, s), 1.79 (3H, s), 1.65 (3H, s), 0.80~2.80 (6H, m), -1.35 (3H, s), -1.55 (3H, s); 207.1, 172.8, 172.3, 171.1, 169.9, 167.1, 157.4, 149.5, 140.0, 138.7, 133.1, 131.8, 130.3, 129.3, 128.9, 128.8, 128.6, 128.3, 127.2, 127.0, 120.7, 82.7, 82.0, 79.2, 78.1, 77.6, 77.5, 75.7, 75.3, 73.3, 70.2~70.5, 68.8, 66.5, 57.6, 55.1, 42.5, 40.3, 38.3, 36.1, 35.3, 34.9, 29.7, 26.0, 23.3, 22.6, 21.4, 16.2, 14.8; HRFABMS m/z 1361.5339 [M+H$^+$] (calcd for $C_{69}H_{89}N_2O_{22}S_2$, 1361.5348).

Example 6.3

Synthesis of an M3 type compound of substituent 6, 32 in Scheme 6.3

Scheme 6.3

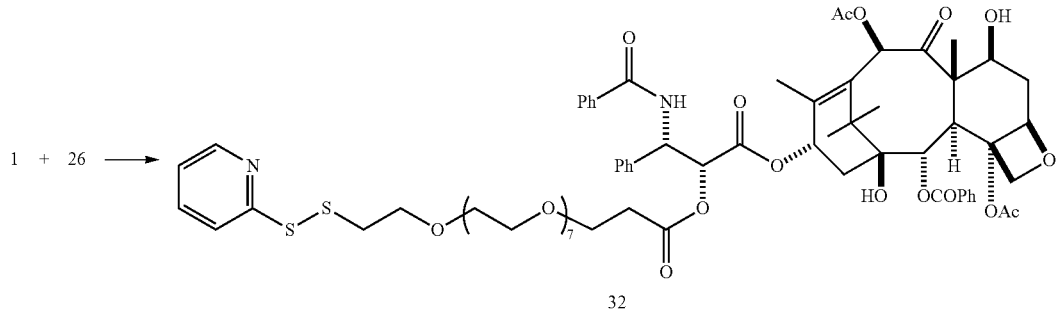

32

Paclitaxel 2'-{O-(2-Carbonylethyl)-O'-(2-[2-(pyridin-2-yl)disulfanyl]ethyl)heptaethylene glycol} 32: To a solution of paclitaxel (1, 11.3 mg, 13.2 nmol) in 2 mL of $CH_2Cl_2$ was added EDCI (2.5 mg, 13.2 μmol). After 15 min stirring, DMAP (2 mg, cat.) was added and stirring continued for 5 min before 26 (11.3 mg, 19.9 mmol) was added. The reaction mixture was allowed to stir at RT for 24 h. Then, 5 mL of $CH_2Cl_2$ was added to the reaction mixture, and the organic phase was washed with sodium bicarbonate, water, and brine, dried over sodium sulfate, and concentrated in a vacuum. The residue was applied to preparative TLC ($R_f$=0.28, 50%

EtOAc/THF) to give SC201-157-2b (16.7 mg, 90%) NMR 32: $\delta_H$ 8.43 (1H, br d, J=4.8 Hz), 8.12 (2H, d, J=7.6 Hz), 7.77 (2H, d, J=7.7 Hz), 7.75 (1H, d, J=7.7 Hz), 7.64 (1H, t, J=8.0 Hz), 7.60 (1H, t, J=8.0 Hz), 7.51 (3H, m), 7.39 (7H, m), 7.07 (1H, dd, J=7.6, 7.2 Hz), 6.27 (1H, s), 6.21 (1H, t, J=8.4 Hz), 5.92 (1H, dd, J=9.2, 3.6 Hz), 5.66 (1H, d, J=7.2 Hz), 5.49 (1H, d, J=3.2 Hz), 4.95 (1H, d, J=8.0 Hz), 4.43 (1H, m), 4.30 (1H, d, J=8.6 Hz), 4.18 (1H, d, J=8.6 Hz), 3.80 (1H, d, J=6.8 Hz), 3.50~3.75 (34H, m), 2.97 (2H, t, J=6.4 Hz), 2.42 (3H, s), 2.21 (3H, s), 1.91 (3H, s), 1.80~2.80 (6H, m), 1.66 (3H, s), 1.21 (3H, s), 1.11 (3H, s); $\delta_C$ 203.8, 171.3, 170.6, 169.8, 168.0, 167.0, 162.6, 149.5, 142.9, 137.1, 137.0, 133.7, 132.7, 131.9, 130.2, 129.1, 128.4~129.1, 127.2, 126.7, 120.6, 119.6, 84.4, 81.0, 79.1, 76.4, 75.6, 75.0, 72.1, 71.7, 70.4~70.6, 68.8, 66.1, 58.5, 52.9, 45.5, 43.1, 38.4, 35.5, 34.6, 26.8, 22.6, 22.1, 20.8, 14.8, 9.5; HRFABMS m/z 1403.5458 [M+H$^+$] (calcd for $C_{71}H_{91}N_2O_{23}S_2$, 1403.5454).

Examples 7.1-7.3

Synthesis of Compounds of Substituent 7, Compounds 35, 37, and 38 in Schemes 7.1-7.3

Simple substitution of acid 33 for acid 26 in Schemes 6.1-6.3 will give compounds 35, 37, and 38 (Schemes 7.1-7.3)

Example 8.2

Synthesis of an M2 Type Compound of Substituent 8, Compound 44 Below

Scheme 7.1

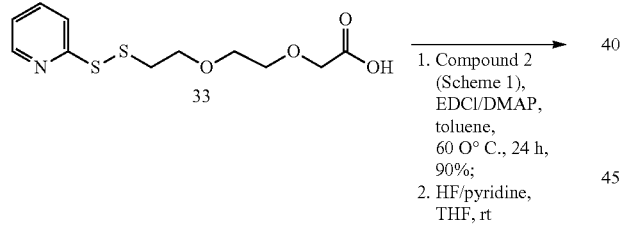

1. Compound 2 (Scheme 1), EDCl/DMAP, toluene, 60° C., 24 h, 90%;
2. HF/pyridine, THF, rt

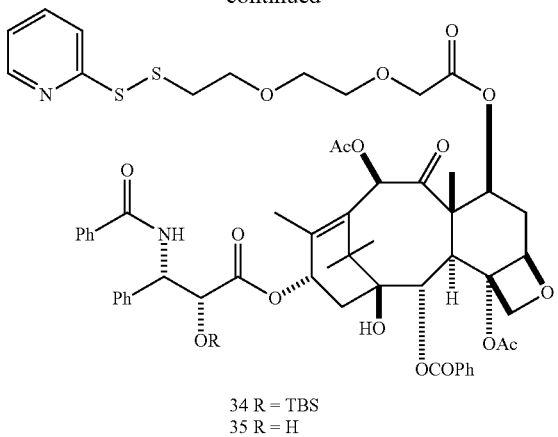

34 R = TBS
35 R = H

Scheme 7.2

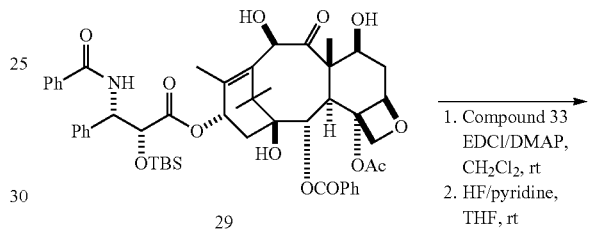

1. Compound 33 EDCl/DMAP, CH$_2$Cl$_2$, rt
2. HF/pyridine, THF, rt

29

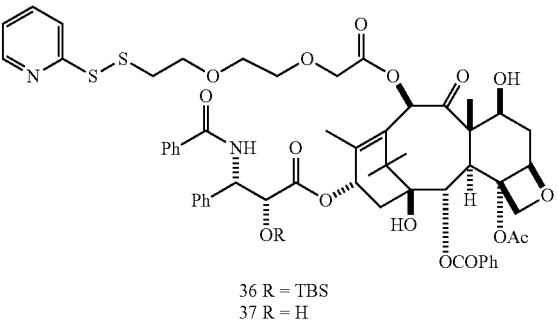

36 R = TBS
37 R = H

Scheme 7.3

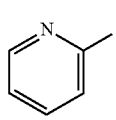 + 33 →

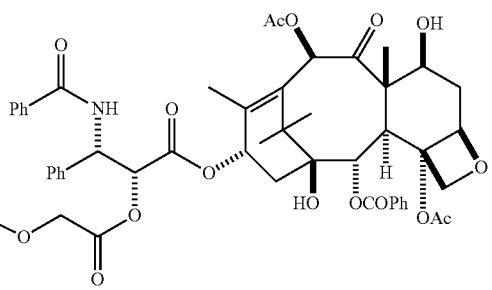

38

Scheme 8.2
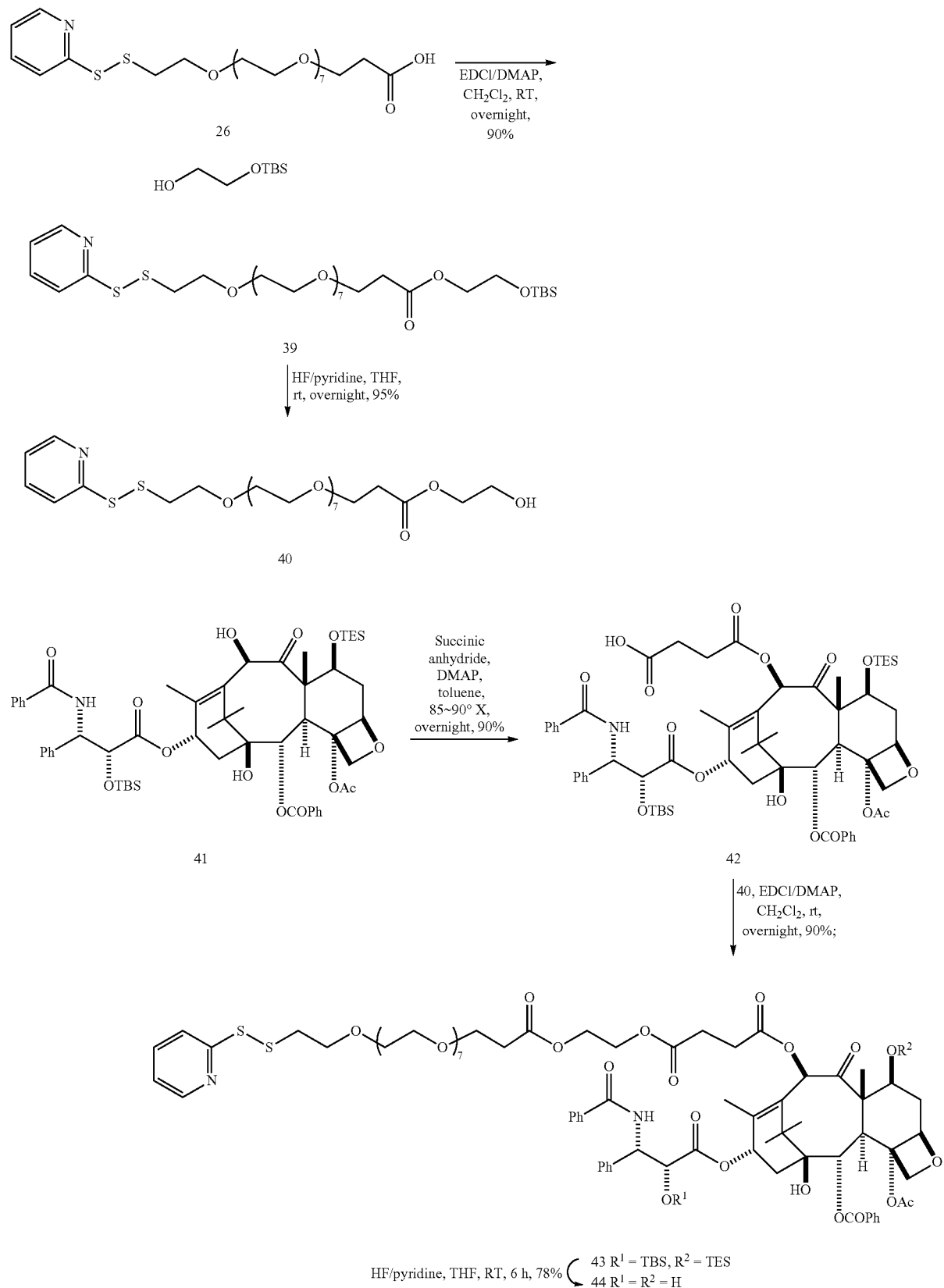

Carboxylic acid 39: To a solution of 2-(tert-butyldimethylsilyloxy)ethanol (MW: 176, MF: $C_8H_{20}O_2Si$; 12.3 mg, 70 µmol) in 1 mL of $CH_2Cl_2$ was added EDCI (6.7 mg, 35 µmol). After 15 min stirring, DMAP (2 mg, cat.) was added and stirring continued for 5 min before 26 (MW: 567, MF: $C_{24}H_{41}NO_{10}S_2$; 20 mg, 35 µmol) was added. The reaction mixture was allowed to stir at RT overnight. Then, 5 mL of $CH_2Cl_2$ was added to the reaction mixture, and the organic phase was washed with sodium bicarbonate, water, and brine, dried over sodium sulfate, and concentrated in a vacuum. The residue was applied to preparative TLC ($R_f$=0.48, 90% EtOAc/MeOH) to give 39 (MW: 725, MF: $C_{32}H_{59}NO_{11}S_2Si$; 22.8 mg, 90%) (Reference: Liu, C.;. Strobl, J. S.; Bane, S.; Schilling, J. K.; McCracken, M.; Chatterjee, S. K.; Rahim-Bata, R.; Kingston, D. G. I. *J. Nat. Prod.* 2004, 67, 152-159.) NMR: $\delta_H$ 8.45 (1H, d, J=4.4 Hz), 7.77 (1H, d, J=8.4 Hz), 7.65 (1H, dd, J=8.4, 7.2 Hz), 7.07 (1H, dd, J=7.2, 4.4 Hz), 4.14 (2H, t, J=4.8 Hz), 3.55~3.82 (34H, m), 2.98 (2H, t, J=6.4 Hz), 2.61 (2H, t, J=6.4 Hz), 0.88 (9H, s), 0.06 (6H, s); $\delta_C$ 171.5, 160.4, 149.5, 137.1, 120.6, 119.6, 70.4~77.0, 68.0, 66.0, 65.7, 61.2, 38.4, 35.0, 29.7, 25.8, −5.1; HRFABMS m/z 726.3370 [M+H$^+$] (calcd for $C_{32}H_{60}NO_{11}S_2Si$, 726.3377).

Deprotected acid 40: To a solution of 39 (6.3 mg, 10.3 µmol), in 1.0 mL of dried THF, was added 0.1 mL of anhydrous pyridine, then the solution was cooled to 0° C., and 0.2 mL of HF-pyridine was added. The reaction mixture was allowed to warm to RT and stirred for overnight. The reaction mixture was then diluted with EtOAc, and the organic phase was washed with sodium bicarbonate, water, and brine, dried over sodium sulfate, and concentrated in a vacuum. The residue was purified by preparative TLC ($R_f$=0.48, 50%, EtOAc:THF) to give 40 (6.0 mg, 95%). (Reference: Liu, C.;. Strobl, J. S.; Bane, S.; Schilling, J. K.; McCracken, M.; Chatterjee, S. K.; Rahim-Bata, R.; Kingston, D. G. I. *J. Nat. Prod.* 2004, 67, 152-159.) NMR: $\delta_H$ 8.46 (1H, d, J=4.4 Hz), 7.77 (1H, d, J=8.4 Hz), 7.65 (1H, dd, J=8.4, 7.2 Hz), 7.07 (1H, dd, J=7.2, 4.4 Hz), 4.22 (2H, t, J=4.8 Hz), 3.54~3.78 (34H, m), 2.95 (2H, t, J=6.4 Hz), 2.60 (2H, t, J=6.4 Hz); $\delta_C$ 171.5, 160.5, 149.5, 137.2, 120.6, 119.8, 70.3~77.0, 69.9, 66.7, 66.2, 60.9, 38.4, 35.2; HRFABMS m/z 612.2509 [M+H$^+$] (calcd for $C_{26}H_{46}NO_{11}S_2$, 612.2512).

2'-TBS-7-TES-10-Deacetylpaclitaxel (41): Prepared by the method of Rice, A.; Liu, Y.; Michaelis, M. L; Himes, R. H.; Georg, G. I.; Audus, K. L. *J. Med. Chem.* 2005, 48, 832-838.

Succinate 42: Using dry toluene (4×0.5 mL), commercially available succinic anhydride (MW: 100, MF: $C_4H_4O_3$; 8 mg, 80 µmol) was transferred into a 10 mL round-bottom reaction flask containing a stirring bar. To this solution were added 41 (MW: 1039, MF: $C_{57}H_{77}NO_{13}Si_2$; 10 mg, 9.6 µmol) and DMAP (2 mg, cat.). The reaction flask was heated at 85-90° C. overnight until the completion of the reaction (monitored by TLC). After cooling to room temperature, the reaction mixture was placed into a separatory funnel containing EtOAc (5 mL) and aqueous HCl (0.2%, 5 mL). The reaction vessel was washed with additional EtOAc (2 mL), which was also collected in the test tube. The aqueous layer was removed and extracted twice with EtOAc (2 mL each). The aqueous layer was discarded. The organic layer was dried over sodium sulfate. The solvent was then removed and the residue was purified by TLC ($R_f$=0.58; 50% EtOAc in THF) to yield 42 (9.8 mg, 90%). (Reference: Rice, A.; Liu, Y.; Michaelis, M. L; Himes, R. H.; Georg, G. I.; Audus, K. L. *J. Med. Chem.* 2005, 48, 832-838.) NMR: $\delta_H$ 8.11 (2H, d, J=8.0 Hz), 7.72 (2H, d, J=8.0 Hz), 7.58 (2H, t, J=8.0 Hz), 7.50 (3H, m), 7.39 (3H, m), 7.32 (2H, m), 7.14 (1H, d, J=8.8 Hz), 6.44 (1H, s), 6.24 (1H, t, J=9.2 Hz), 5.74 (1H, d, J=8.8 Hz), 5.70 (1H, d, J=7.2 Hz), 4.96 (1H, d, J=9.6 Hz), 4.67 (1H, s), 4.46 (1H, dd, J=10.4, 6.4 Hz), 4.31 (1H, d, J=6.4 Hz), 4.21 (1H, d, J=6.4 Hz), 3.82 (1H, d, J=6.8 Hz), 2.10~2.80 (8H, m), 2.57 (3H, s), 2.00 (3H, s), 1.80~2.80 (8H, m), 1.69 (3H, s), 1.20 (3H, s), 1.15 (3H, s), 0.89 (9H, t, J=7.6 Hz), 0.78 (9H, s), 0.57 (6H, q, J=7.6 Hz), −0.04 (3H, s), −0.30 (3H, s); $\delta_C$ 201.4, 177.7, 172.6, 171.4, 170.3, 167.5, 166.8, 140.3, 138.1, 133.9, 133.5, 131.9, 130.2, 129.3, 128.7, 128.7, 127.9, 127.0, 126.4, 84.2, 81.2, 78.5, 75.2, 75.0, 74.9, 72.2, 71.5, 58.4, 55.6, 51.9, 46.6, 43.2, 37.2, 35.5, 28.8, 26.4, 25.5, 23.1, 21.5, 18.0, 14.3, 10.1, 6.7, 5.6, 5.3, −5.2, −5.9; HRFABMS m/z 1140.5174 [M+H$^+$] (calcd for $C_{61}H_{82}NO_{16}Si_2$, 1140.5172).

Sulfanyl derivative 43: To a solution of alcohol 40 (MW: 611, MF: $C_{26}H_{45}NO_{11}S_2$; 5 mg, 8.2 µmol) in 1 mL of $CH_2Cl_2$ was added EDCI (1.6 mg, 8.2 µmol). After 15 min stirring, DMAP (2 mg, cat.) was added and stirring continued for 5 min before acid 42 (MW: 1039, MF: $C_{61}H_{81}NO_{16}Si_2$; 8.5 mg, 8.2 µmol) was added. The reaction mixture was allowed to stir at RT overnight. Then, 5 mL of $CH_2Cl_2$ was added to the reaction mixture, and the organic phase was washed with sodium bicarbonate, water, and brine, dried over sodium sulfate, and concentrated in a vacuum. The residue was applied to preparative TLC ($R_f$=0.48, 90% EtOAc/MeOH) to give 43 (3.5 mg, 25%; 90% based on unreacted 42). NMR: $\delta_H$ 8.46 (1H, br s), 8.13 (2H, d, J=7.2 Hz), 7.80 (1H, d, J=7.7 Hz), 7.75 (2H, d, J=7.2 Hz), 7.68 (1H, t, J=8.0 Hz), 7.59 (1H, t, J=8.0 Hz), 7.25~7.55 (10H, m), 7.10 (1H, dd, J=7.2, 4.4 Hz), 6.46 (1H, s), 6.27 (1H, t, J=9.2 Hz), 5.74 (1H, d, J=8.8 Hz), 5.70 (1H, d, J=7.2 Hz), 4.96 (1H, d, J=9.6 Hz), 4.68 (1H, br s), 4.48 (1H, dd, J=10.4, 6.4 Hz), 4.25~4.35 (5H, m), 4.22 (1H, d, J=8.3 Hz), 3.84 (1H, d, J=6.8 Hz), 3.50~3.80, 3.00 (2H, t, J=6.4 Hz), 2.65 (2H, t, J=6.4 Hz), 2.57 (3H, s), 2.02 (3H, s), 1.80~2.80 (8H, m), 1.71 (3H, s), 1.21 (3H, s), 1.16 (3H, s), 0.93 (9H, t, J=7.6 Hz), 0.81 (9H, s), 0.57 (6H, q, J=7.6 Hz), −0.02 (3H, s), −0.28 (3H, s); $\delta_C$ 201.2, 171.8, 171.4, 170.2, 166.4, 166.5, 160.2, 140.2, 138.3, 137.2, 133.5, 133.3, 133.3, 131.4, 126.0~130.0, 121.0, 84.2, 81.2, 78.9, 75.2, 75.1, 72.2, 71.5, 71.0, 69.0, 67.0, 62.2, 58.4, 56.1, 47.0, 43.2, 38.2, 37.0, 36.0, 35.2, 29.3, 29.0, 26.8, 25.7, 23.3, 21.2, 18.2, 14.3, 10.2, 7.0, 5.5, −5.2, −5.8; HRFABMS m/z 1733.7478 [M+H$^+$] (calcd for $C_{87}H_{125}N_2O_{26}S_2Si_2$, 1733.7501).

Deprotected product 44: To a solution of 43 (3 mg, 1.7 µmol), in 1.0 mL of dried THF, was added 0.1 mL of anhydrous pyridine, then the solution was cooled to 0° C., and 0.2 mL of HF-pyridine was added. The reaction mixture was allowed to warm to rt and stirred for 6 h. The reaction mixture was then diluted with EtOAc, and the organic phase was washed with sodium bicarbonate, water, and brine, dried over sodium sulfate, and concentrated in a vacuum. The residue was purified by preparative TLC ($R_f$=0.33, 75%, EtOAc:THF) to give 44 (2.0 mg, 78%). NMR: $\delta_H$ ($CDCl_3$+$CD_3OD$) 8.34 (1H, d, J=4.4 Hz), 8.03 (2H, d, J=7.2 Hz), 7.72 (1H, d, J=8.0 Hz), 7.70 8.03 (2H, d, J=7.2 Hz), 7.65 (1H, t, J=8.0 Hz), 7.30~7.50 (11H, m), 7.07 (1H, dd, J=7.6, 7.2 Hz), 6.24 (1H, s), 6.09 (1H, t, J=9.0, 8.7 Hz), 5.66, (1H, br s), 5.61 (1H, d, J=6.9 Hz), 4.89 (1H, d, J=9.6 Hz), 4.70 (1H, s), 4.20~4.30, 4.16 (1H, d, J=8.6 Hz), 3.45~3.70, 2.10~2.80 (8H, m), 2.30 (3H, s), 1.78 (3H, s), 1.59 (3H, s), 1.12 (3H, s), 1.06 (3H, s); $\delta_C$ ($CD_3OD$) 203.2, 173.0, 172.0, 170.8, 170.2, 169.0, 166.5, 160.0, 149.0, 140.8, 138.3, 138.0, 135.1, 134.2, 131.8, 130.0, 128.0, 124~126, 121.0, 120.0, 84.8, 82.3, 78.0, 76.2, 75.8, 75.3, 73.8, 71.2, 69.8~70.1, 68.3, 66.0, 62.2, 60.2, 58.1, 56.5, 46.3, 43.2, 38.2, 36.3, 35.0, 34.0, 29.3, 28.4, 25.6, 22.2, 21.2, 19.8, 12.8, 12.1, 9.3; HRFABMS m/z 1505.5733 [M+H$^+$] (calcd for $C_{75}H_{97}N_2O_{26}S_2$, 1505.5771).

Example 8.1

Synthesis of M1 Compound of Substituent 8 (47 in this Example)

Scheme 8.1

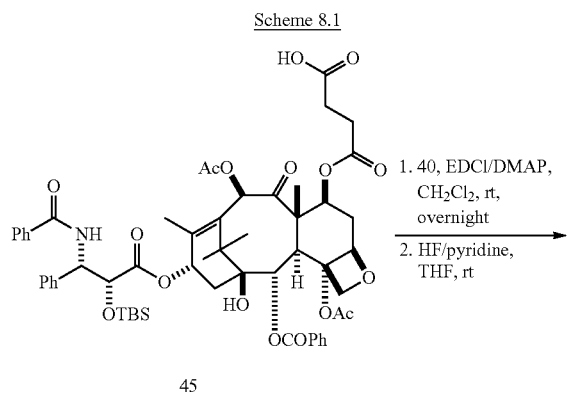

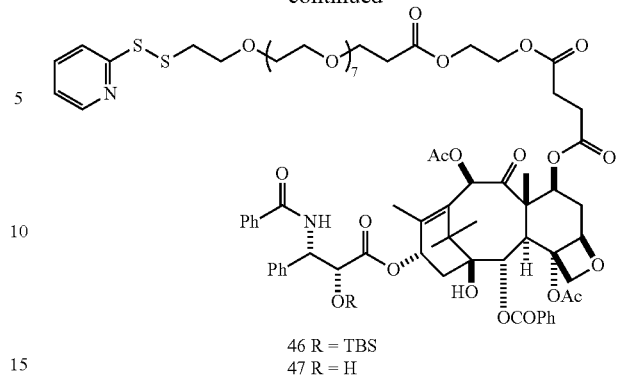

46 R = TBS
47 R = H

2'-TBS-7-succinylpaclitaxel (45): This compound can be prepared by a modification of the method described in: Grothaus, P. G.; Raybould, T. J. G.; Bignami, G. S.; Lazo, C. B.; Byrnes, J. B. An enzyme immunoassay for the determination of taxol and taxanes in *Taxus* sp. tissues and human plasma. Journal of Immunological Methods (1993), 158(1), 5-15.

2'-TBS-7-disulfanyl paclitaxel derivative 46: This compound can be prepared by a modification of the method described above for the synthesis of compound 43.

7-Disulfanyl paclitaxel derivative 47: Deprotection of 46 as previously described will yield 47.

Example 8.3

Synthesis of M3 Compound of Substituent 8 (49 in this Example)

Scheme 8.3

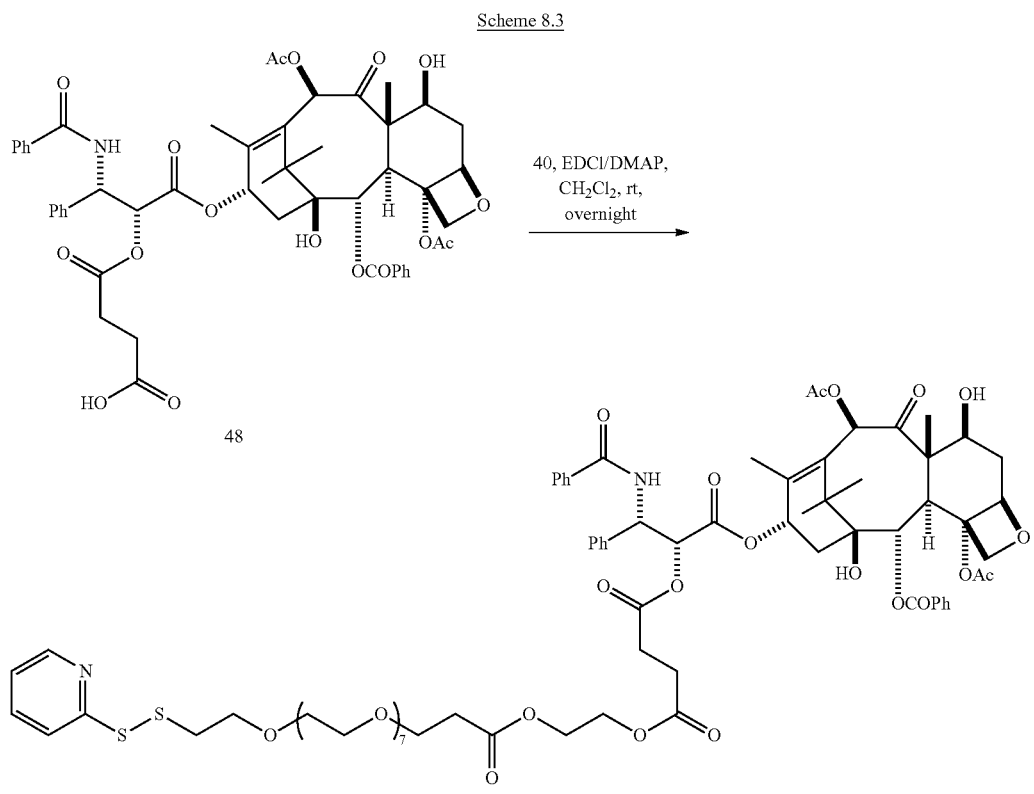

2'-Succinylpaclitaxel (48): This compound can be prepared by the method of Kingston and Zhao: Zhao, Z.; Kingston, D. G. I.; Crosswell, A. R. Modified taxols, 6. Preparation of water-soluble prodrugs of taxol. Journal of Natural Products (1991), 54(6), 1607-11.

Compound 49: Reaction of 2'-succinylpaclitaxel (48) with compound 40 as described above will give compound 49.

Example 9.3

Synthesis of M3 Compound of Substituent 9 (52 in this Example)

2-(2-tert-butyldimethylsiloxyethoxy)ethanol. To a 0° C. solution of di(ethyleneglycol) (0.35 mL, 3.69 mmol) in $CH_2Cl_2$ (4 mL) was added imidazole (0.126 g, 1.85 mmol) and the resulting mixture was stirred 5 min and TBSCl (0.279 g, 1.85 mmol) was added in one portion. The reaction mixture was stirred 1 hr at 0° C. and warmed to rt and stirred overnight. Water was added, the organic layer was washed with 10% HCl, satd $NaHCO_3$, brine, dried over $MgSO_4$, and the solvent was evaporated to give the crude product that was purified by flash chromatography using 30% EtOAc/hexane as eluant to give the desired 2-(2-tert-butyldimethylsiloxy-

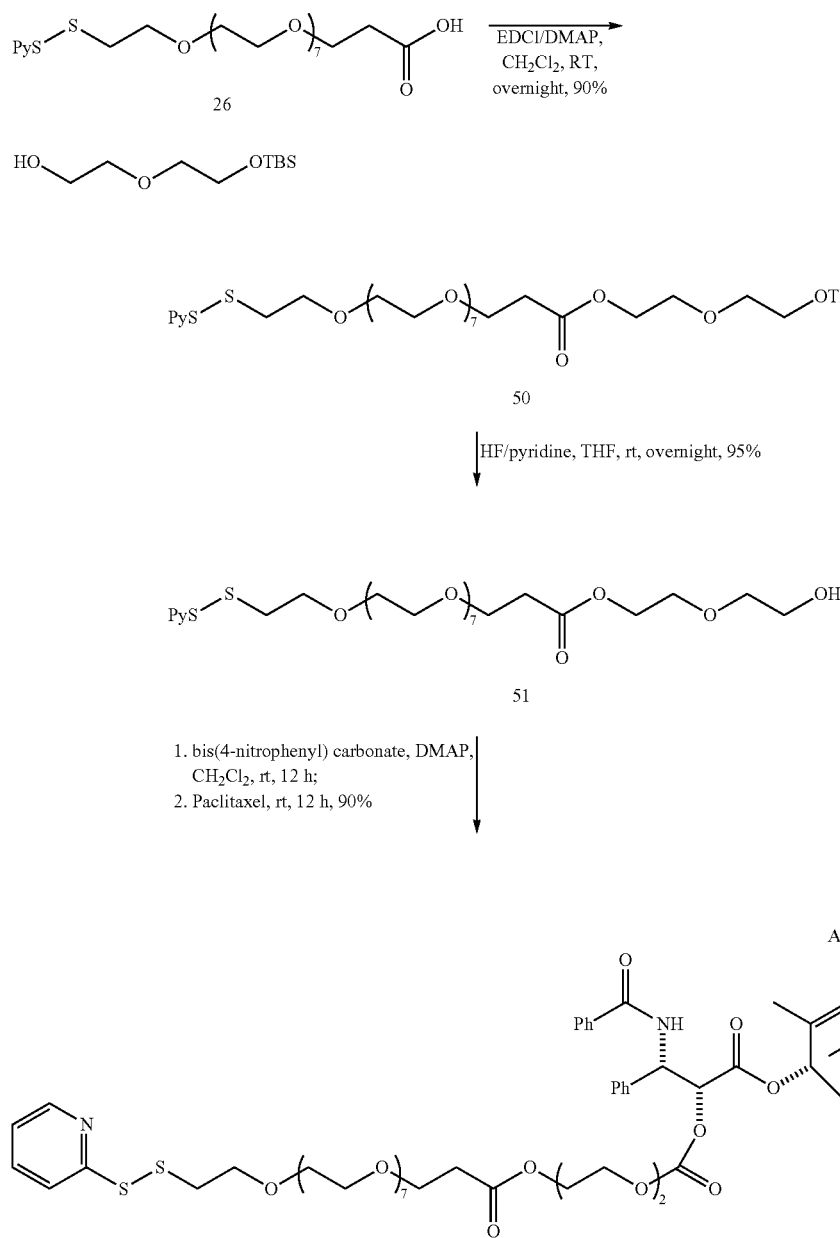

ethoxy)ethanol (240 mg, 60% based on TBSCl) as a colorless liquid. (Lautens, M.; Paquin, J-F.; Piguel, S. *J. Org. Chem.* 2002, 67, 3972-3974.)

TBS Ether 50: To a solution of 2-(2-tert-butyldimethylsiloxyethoxy)ethanol (32 mg, 0.145 mmol) in 3 mL of $CH_2Cl_2$ was added EDCI (27.8 mg, 0.145 mmol). After 15 min stirring, DMAP (2 mg, cat.) was added and stirring continued for 5 min before 26 (54 mg, 0.095 mmol) was added. The reaction mixture was allowed to stir at rt for 24 h. Then, 5 mL of $CH_2Cl_2$ was added to the reaction mixture, and the organic phase was washed with sodium bicarbonate, water, and brine, dried over sodium sulfate, and concentrated in a vacuum. The residue was applied to preparative TLC ($R_f$=0.48, 90% EtOAc/MeOH) to give 50 (65.7 mg, 90%) NMR: $\delta_H$ 8.43 (1H, d, J=4.8 Hz), 7.77 (1H, d, J=8.0 Hz), 7.65 (1H, t, J=8.0 Hz), 7.06 (1H, dd, J=8.0, 4.8 Hz), 4.21 (1H, t, J=4.8 Hz), 3.50~3.80 (38H, m), 2.98 (1H, t, J=7.0 Hz), 2.60 (1H, t, J=5.2 Hz), 0.87 (6H, s), 0.04 (9H, s); $\delta_C$ 171.5, 160.4, 149.5, 137.1, 120.6, 119.6, 72.6, 70.2~70.5, 69.1, 68.9, 66.5, 63.7, 62.7, 38.4, 34.9, 25.9, 18.3, -5.3; HRFABMS m/z 792.34586 [M+Na$^+$] (calcd for $C_{34}H_{63}NO_{12}S_2SiNa$, 792.34586).

Alcohol 51: To a solution of 50 (9 mg, 0.012 mmol), in 1.0 mL of dried THF, was added 0.1 mL of anhydrous pyridine, then the solution was cooled to 0° C., and 0.2 mL of HF-pyridine was added. The reaction mixture was allowed to warm to rt and stirred overnight. The reaction mixture was then diluted with EtOAc, and the organic phase was washed with sodium bicarbonate, water, and brine, dried over sodium sulfate, and concentrated in a vacuum. The residue was purified by preparative TLC ($R_f$=0.3, 100:15, EtOAc:MeOH) to give 51 (6.9 mg, 90%). NMR: $\delta_H$ 8.50 (1H, d, J=4.8 Hz), 7.79 (1H, d, J=8.0 Hz), 7.68 (1H, t, J=8.0 Hz), 7.10 (1H, dd, J=8.0, 4.8 Hz), 4.26 (1H, t, J=4.8 Hz), 3.50~3.80 (38H, m), 2.98 (1H, t, J=7.0 Hz), 2.63 (1H, t, J=5.2 Hz); $\delta_C$ 171.5, 160.1, 149.1, 137.8, 120.9, 120.1, 72.3, 70.2~70.5, 68.9, 68.7, 66.5, 63.5, 61.7, 38.5, 35.0; HRFABMS m/z 656.2768 [M+H$^+$] (calcd for $C_{28}H_{50}NO_{12}S_2$, 656.2774).

Disulfanyl paclitaxel derivative 52: To a solution of compound 51 (5 mg, 7.6 μmol) in dry $CH_2Cl_2$ (1 mL) was added to the stirred solution of bis(4-nitrophenyl) carbonate (2.5 mg, 8.4 μmol) and 4-(dimethylamino) pyridine (2 mg, cat.) in dry $CH_2Cl_2$ (1 mL). The mixture was stirred at rt overnight. Then paclitaxel (7.9 mg, 9.2 μmol) was added, and the mixture was stirred at rt overnight. Usual workup and purification by TLC ($R_f$=0.3, 90% EtOAc/MeOH) afforded compound 52 (10.5 mg, 90%): (modified method from Fardis, M.; Pyun, H.-J.; Tario, J.; Jin, H.; Kim, C. U.; Ruckman, J.; Lin, Y.; Green, L.; Hicke, B. *Bioorg. Med. Chem.* 2003, 11, 5051-5058; Liu, C.; Schilling, J. K.; Ravindra, R.; Bane, S.; Kingston, D. G. I. *Bioorg. Med. Chem.* 2004, 12, 6147-6161.) NMR: $\delta_H$ 8.44 (1H, d, J=2.8 Hz), 8.12 (2H, d, J=7.7 Hz), 7.76 (2H, d, J=7.7 Hz), 7.75 (1H, d, J=7.7 Hz), 7.67 (1H, t, J=8.0 Hz), 7.59 (1H, t, J=8.0 Hz), 7.49 (3H, m), 7.41 (7H, m), 7.09 (1H, t, J=8.0 Hz), 6.86 (1H, d, J=9.1 Hz), 6.28 (1H, s), 6.26 (1H, t, J=8.4 Hz), 5.96 (1H, br d, J=9.2 Hz), 5.68 (1H, d, J=6.8 Hz), 5.41 (1H, d, J=2.0 Hz), 4.96 (1H, d, J=9.2 Hz), 4.43 (1H, dd, J=9.2, 7.2 Hz), 4.18~4.32 (4H, m), 3.80 (1H, d, J=6.8 Hz), 3.55~3.75 (38H, m), 2.96 (2H, t, J=6.8 Hz), 2.58 (2H, t, J=6.8 Hz), 2.44 (3H, s), 2.22 (3H, s), 1.92 (3H, s), 1.80~2.60 (4H, m), 1.67 (3H, s), 1.23 (3H, s), 1.13 (3H, s); $\delta_C$ 203.8, 171.3, 169.8, 167.9, 167.5, 167.0, 162.6, 154.1, 149.5, 142.7, 137.3, 133.7, 132.8, 132.1, 130.2, 129.1, 128.7, 128.6, 127.2, 126.6, 126.1, 120.7, 119.7, 84.4, 81.0, 79.1, 75.5, 75.0, 72.1, 70.3~70.4, 69.1, 68.8, 68.6, 68.0, 66.4, 63.5, 58.5, 52.8, 45.5, 43.2, 38.3, 35.4~35.5, 34.8, 29.7, 26.8, 22.7, 22.1, 20.8, 14.8, 9.6; HRFABMS m/z 1535.5876 [M+H$^+$] (calcd for $C_{76}H_{99}N_2O_{27}S_2$, 1535.5877).

Example 9.3

Synthesis of M1 Compound of Substituent 9 (54 in this Example)

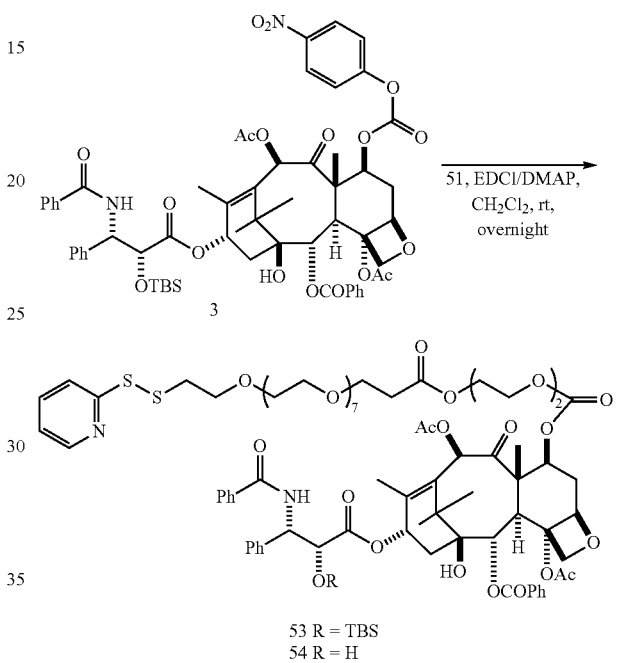

Reaction of the previously prepared carbonate 3 with alcohol 51 will give derivative 53, which can be deprotected in the usual way to give compound 54.

Example 10.1

Synthesis of M1 Compound of Substituent 10 (54 in this Example)

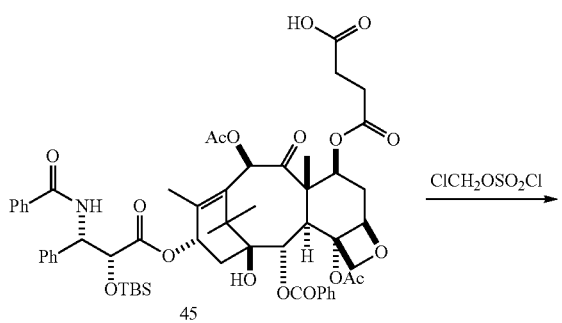

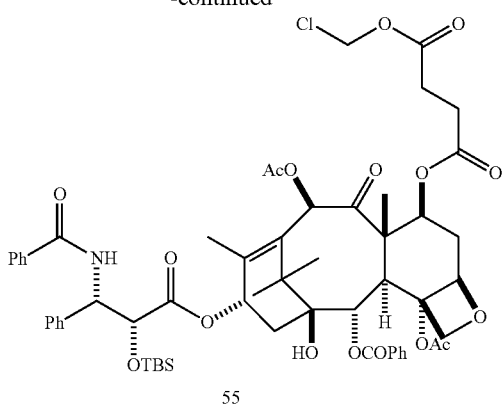
55
1. Compound 33, 18-Crown-6, K₂CO₃
   NaI, Benzene, reflux, 2 h,
2. HF/pyridiine, THF, rt
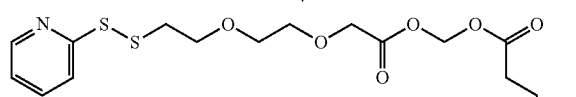
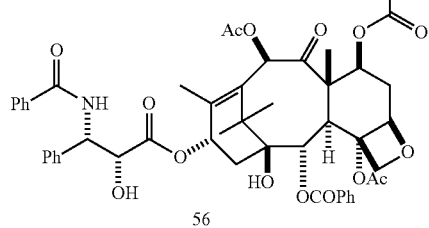
56
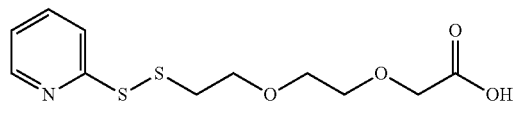
33
Example 10.3
Synthesis of M3 Compound of Substituent 10 (58 in this Example)
Scheme 10.3
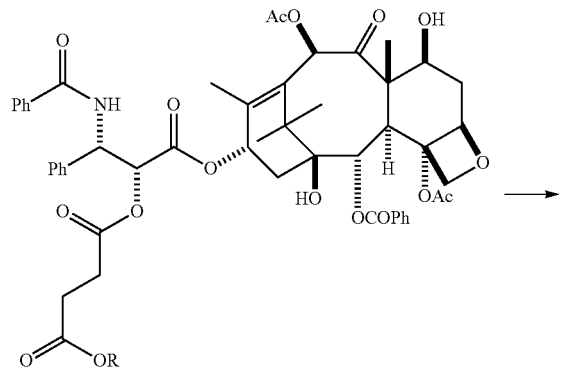
48 R = H
57 R = CH₂Cl
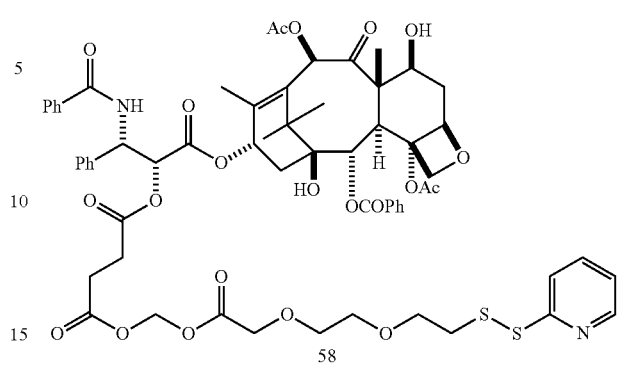
58
Example 11.1
Synthesis of M1 Compound of Substituent 11 (60 in this Example)
Scheme 11.1
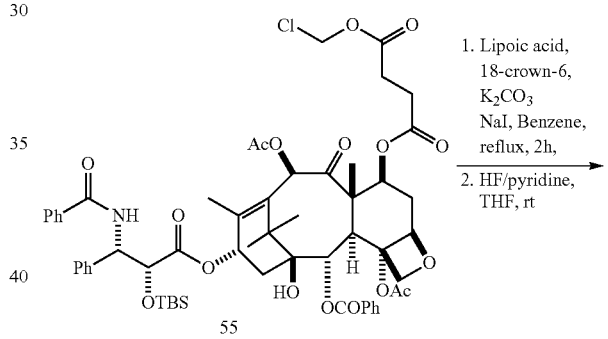
55
1. Lipoic acid, 18-crown-6, K₂CO₃ NaI, Benzene, reflux, 2h,
2. HF/pyridine, THF, rt
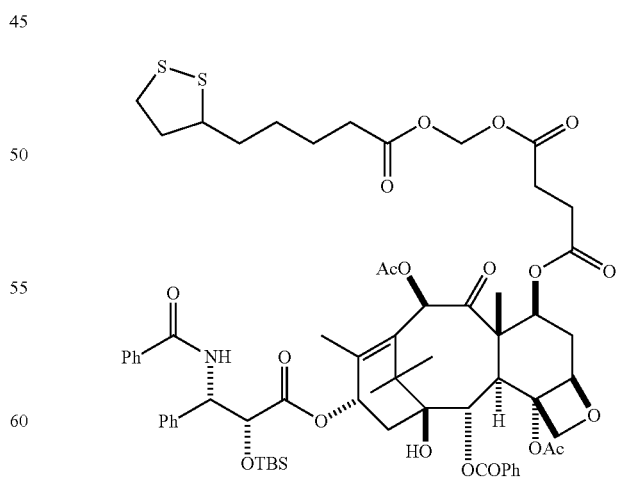
59 R = TBS
60 R = H

Example 11.3

Synthesis of M3 Compound of Substituent 11 (61 in this Example)

Scheme 11.3

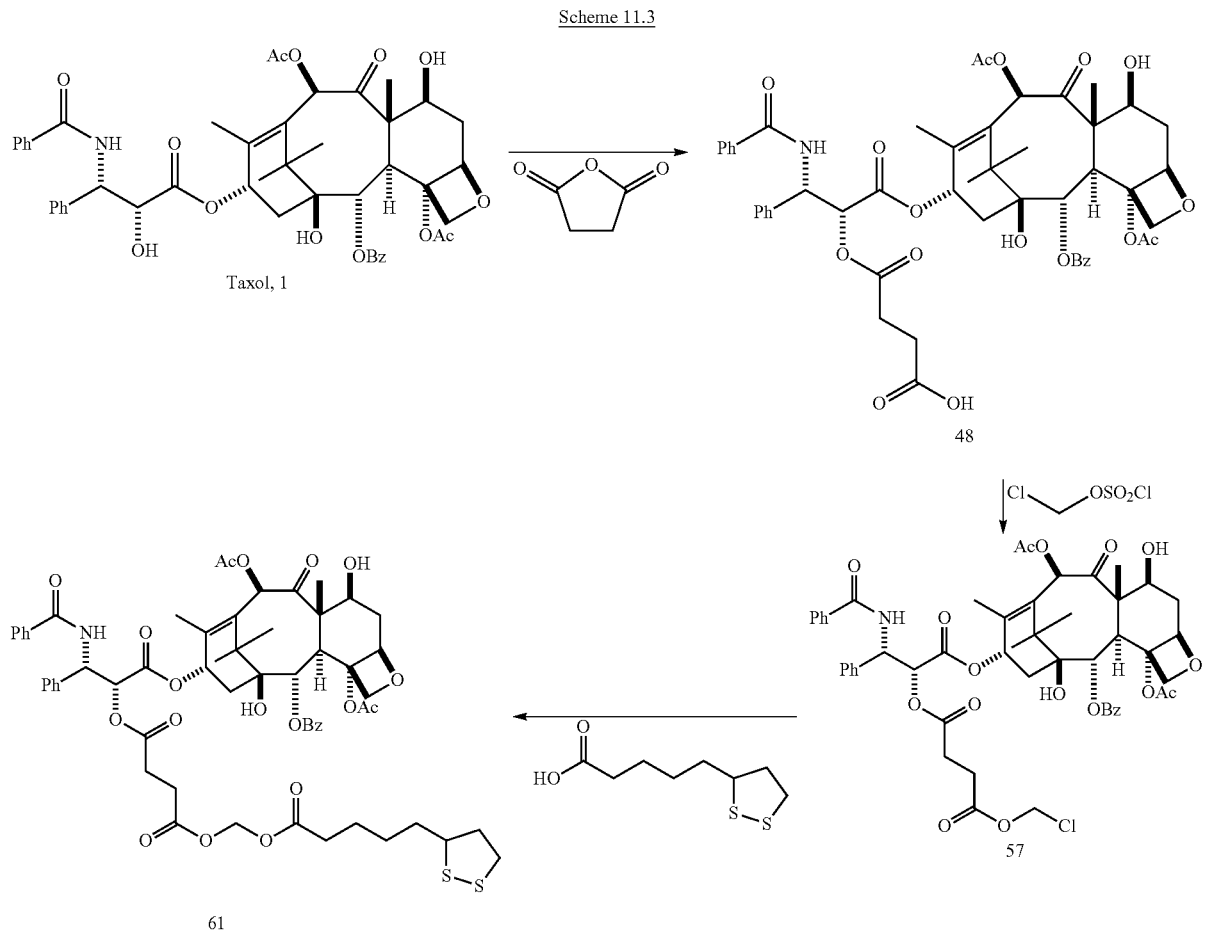

Synthesis of compound 48. A dry round bottom flask was equipped with a magnet stirring bar and a rubber septum. After being evacuated for 5 min and flushed with nitrogen, the flask was charged with paclitaxel (50 mg, 59 μmol). Dry pyridine (4 mL) was added via syringe to dissolve the paclitaxel solid. To the resulting solution was added succinic anhydride (90 mg, 0.9 mmol) while stirring. The resulting mixture was stirred for 3 h under a nitrogen atmosphere. The extra solvent was evaporated under vacuum and the residue was applied to a silica gel column eluted with was purified with a silica gel column using dichloromethane and 6% methanol to afford the compound 48 as a white solid (55 mg, 92%). $^1$H NMR (CDCl$_3$, 500 MHz): 1.13 (s, 3H), 1.12 (s, 3H), 1.65 (s, 3H), 1.86 (m, 1H), 1.91 (s, 3H), 2.16 (s, 3H), 2.17 (m, 1H), 2.38 (s, 3H), 2.46 (m, 1H), 2.55 (m, 1H), 2.62 (m, 2H), 2.74 (m, 2H), 3.80 (d, J=7.5 Hz, 1H), 4.18 (AB, J=7.0 Hz, 1H), 4.33 (dd, J=9.0 Hz, 4.5 Hz, 1H), 4.99 (dd, J=9.5 Hz, 9.5 Hz, 1H), 5.47 (d, J=5.0 Hz), 5.63 (d, J=7.5 Hz, 1H), 5.84 (d, J=7.0 Hz, 1H), 6.07 (t, J=9.0 Hz, 1H), 6.44 (s, 1H), 7.26 (m, 1H), 7.41~7.60 (m, 9H), 7.66 (m, 1H), 7.81 (m, 2H), 8.11 (m, 2H).

Synthesis of compound 57. A mixture of CH$_2$Cl$_2$ (2 mL) and 2 mL of aqueous solution containing compound 48 (20.8 mg, 0.022 mmol), NaHCO$_3$ (9 mg, 0.11 mmol), and tetrabutylammonium bisulfate (1 mg, 0.003 mmol) was stirred for 10 min at room temperature. Chloromethyl chlorosulfate (4.6 mg, 0.028 mmol) was added. The reaction mixture was vigorously stirred at room temperature for 2 h. The reaction mixture was diluted with 10 mL dichloromethane, washed with brine (2×1 mL), dried over anhydrous Na$_2$SO$_4$, filtered, and evaporated under reduced pressure. The residue was applied on PTLC with hexane and ethyl acetate (1:2) as developing solvent to yield compound 57 (10 mg, 46% yield). $^1$H NMR (CDCl$_3$, 500 MHz): 1.12 (s, 3H), 1.23 (s, 3H), 1.67 (s, 3H), 1.87 (m, 1H), 1.92 (s, 3H), 2.15 (m, 1H), 2.22 (s, 3H), 2.37 (m, 1H), 2.44 (s, 3H), 2.55 (m, 1H), 2.68 (m, 2H), 2.78 (m, 2H), 3.80 (d, J=7.0 Hz, 1H), 4.19 (d, J=8.5 Hz, 1H), 4.31 (d, J=8.5 Hz, 1H), 4.43 (m, 1H), 4.96 (d, J=7.5 Hz, 1H) 5.50 (d, J=3.0 Hz), 5.57 (s, 2H), 5.68 (d, J=7.0 Hz, 1H), 5.98 (dd, J=6.5, 3.0 Hz, 1H), 6.23 (t, 9.0 Hz, 1H) 6.28 (s, 1H), 6.94 (d, J=9.0 Hz, 1H), 7.34~7.45 (m, 7H), 7.52 (m, 3H), 7.60 (m, 1H), 7.77 (m, 2H), 8.14 (m, 2H).

Synthesis of compound 61. A mixture of 57 (10 mg, 0.01 mmol), lipoic acid (4.4 mg, 0.02 mmol), K$_2$CO$_3$ (4.4 mg, 0.03 mmol), 18-crown-6 (16.8 mg, 0.06 mmol) and NaI (cat.) was refluxed in benzene for 5 hr. The reaction mixture was diluted with ether (10 mL) and washed with water (2×1 mL) and brine (2×1 mL). The resulting crude product was purified by PTLC (1:2 hexane/EtOAc) to give compound 61 as a white solid (7 mg, 60% yield). ¹H NMR (CDCl₃, 500 MHz): 1.12 (s, 3H), 1.23 (s, 3H), 1.40~1.50 (m, 2H), 1.64 (m, 2H), 1.67 (s, 3H), 1.87 (m, 1H), 1.92 (s, 3H), 2.15 (m, 1H), 2.22 (s, 3H), 2.30~2.40 (m, 3H), 2.44 (s, 3H), 2.45 (m, 2H), 2.55 (m, 1H), 2.68 (m, 2H), 2.78 (m, 2H), 3.06~3.18 (m, 2H), 3.54 (m, 1H), 3.80 (d, J=7.0 Hz, 1H), 4.19 (d, J=8.5 Hz, 1H), 4.31 (d, J=8.5 Hz, 1H), 4.43 (m, 1H), 4.96 (d, J=7.5 Hz, 1H) 5.50 (d, J=3.0 Hz), 5.64 (m, 2H), 5.68 (d, J=7.0 Hz, 1H), 5.98 (dd, J=6.5, 3.0 Hz, 1H), 6.23 (t, 9.0 Hz, 1H) 6.28 (s, 1H), 6.98 (d, J=9.0 Hz, 1H), 7.34~7.45 (m, 7H), 7.52 (m, 3H), 7.60 (m, 1H), 7.77 (m, 2H), 8.14 (m, 2H).

Example 12.1

Synthesis of M1 Compound of Substituent 12 (64 in this Example)

Scheme 12.1

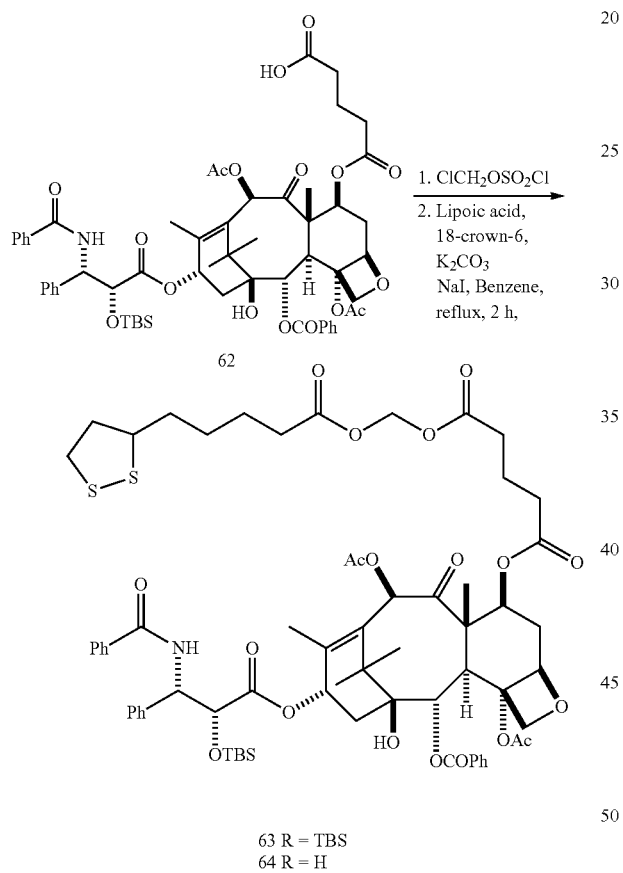

63 R = TBS
64 R = H

Example 12.3

Synthesis of M3 Compound of Substituent 12 (66 in this Example)

Scheme 12.3

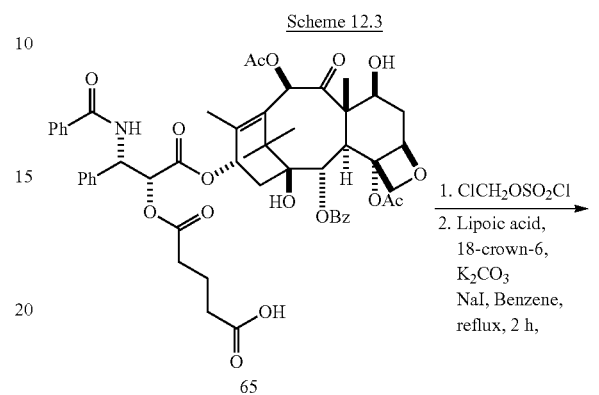

Example 13.3

Synthesis of M3 Compound of Substituent 13 (68 in this Example)

Scheme 13.3

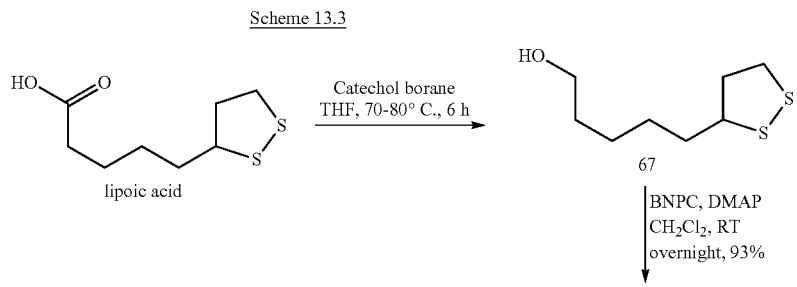

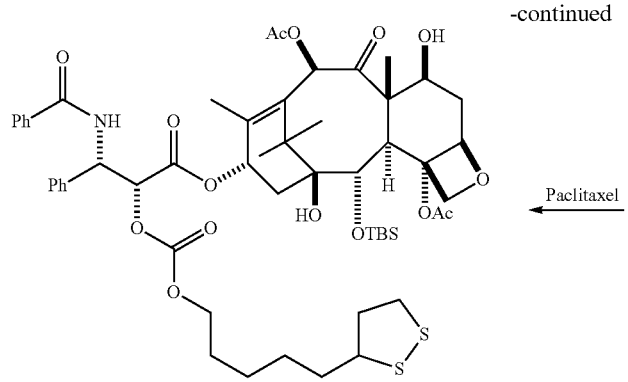

68

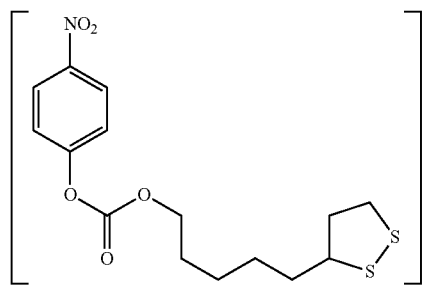

Paclitaxel ←

-continued

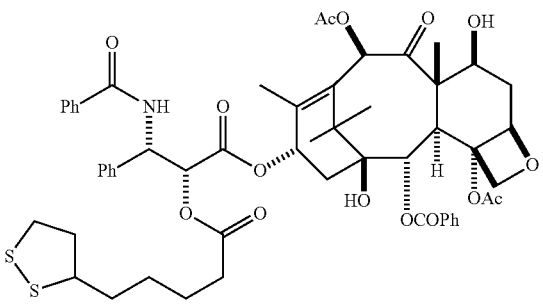

69

Synthesis of compound 67. A solution of catechol borane in dry tetrahydrofuran (50 μmol) was added to a stirred solution of lipoic acid (20.6 mg, 10 μmol) tetrahydrofuran (1 mL). The reaction mixture was allowed to stir at 70~80° C. for 6 h under Argon. Workup as described in the literature (Kabalka, G. W.; Baker, J. D., Jr.; Neal, G. W. Catecholborane (1,3,2-benzodioxaborole). A versatile reducing agent. *J. Org. Chem.* 1977, 42, 512-17) and purification by preparative TLC (30% EtOAc/hexanes) afforded compound 65 (5.8 mg, 30%).

Synthesis of compound 68. A solution of 67 (1.9 mg, 10 μmol) in dry dichloromethane (1 mL) was added to a stirred solution of bis(4-nitrophenyl) carbonate (3.3 mg, 11 μmol) and 4-(dimethylamino) pyridine (3.7 mg, 30 μmol) in dry dichloromethane (1 mL). After being stirred at room temperature for 12 h, paclitaxel (1) (10.2 mg, 12 μmol) was added. The reaction mixture was allowed to stir at room temperature for another 12 h. Workup as described above and purification by preparative TLC (60% EtOAc/hexanes) afforded compound 66 (10 mg, 93%): $\delta_H$ 8.12 (2H, d, J=7.7 Hz), 7.73 (2H, d, J=7.7 Hz), 7.59 (1H, t, J=7.5 Hz), 7.50 (3H, m), 7.40 (7H, m), 6.96 (1H, d, J=9.1 Hz), 6.28 (2H, m), 5.96 (1H, dd, J=9.4, 2.5 Hz), 5.67 (1H, d, J=7.2 Hz), 5.41 (1H, d, J=2.5 Hz), 4.96 (1H, d, J=9.7 Hz), 4.43 (1H, m), 4.30 (1H, d, J=8.7 Hz), 4.18 (1H, d, J=8.7 Hz), 4.10 (2H, m), 3.80 (1H, d, J=6.9 Hz), 3.53 (1H, m), 3.15 (1H, m), 3.08 (1H, m), 2.60~1.30 (14H, m), 2.44 (3H, s), 2.21 (3H, s), 1.92 (3H, s), 1.66 (3H, s), 1.22 (3H, s), 1.12 (3H, s); $\delta_C$ 203.8, 171.2, 169.8, 167.9, 167.1, 167.0, 154.2, 142.6, 136.7, 133.4, 132.7, 132.0, 130.2, 129.1, 128.7, 128.7, 128.5, 127.1, 126.5, 84.4, 81.0, 79.1, 76.5, 76.4, 75.5, 75.0, 72.1, 72.0, 69.1, 58.4, 56.4, 52.7, 45.5, 43.1, 40.2, 38.4, 35.5, 35.5, 34.7, 28.8, 28.3, 26.8, 25.3, 22.7, 22.1, 20.8, 14.8, 9.5. HRFABMS m/z 1072.3804 [M+Na$^+$] (calcd for $C_{56}H_{66}NO_{16}S_2$, 1072.3823.

Example 14.3

Synthesis of M3 Compound of Substituent 14 (69 in this Example)

Scheme 14.3

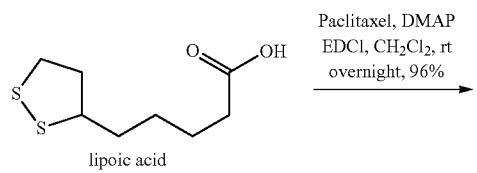

lipoic acid

Paclitaxel, DMAP
EDCl, CH$_2$Cl$_2$, rt
overnight, 96%
→

Synthesis of compound 69. A solution of lipoic acid (2.06 mg, 10 μmol) in dry dichloromethane (1 mL) was added to a stirred solution of paclitaxel (10.2 mg, 12 μmol) and 4-(dimethylamino) pyridine (3.7 mg, 30 μmol) in dry dichloromethane (1 mL). The reaction mixture was allowed to stir at room temperature for 12 h. Workup as described above and purification by preparative TLC (60% EtOAc/hexanes) afforded compound 69 (10 mg, 96%): NMR (CDCl$_3$) $\delta_H$ 8.12 (2H, d, J=8.0 Hz), 7.72 (2H, d, J=8.3 Hz), 7.59 (1H, t, J=8.0 Hz), 7.50 (3H, m), 7.32~7.42 (7H, m), 6.88 (1H, d, J=9.1 Hz), 6.28 (1H, br s), 6.24 (1H, t, J=9.1 Hz), 5.95 (1H, dd, J=9.3, 3.0 Hz), 5.67 (1H, d, J=7.2 Hz), 5.50 (1H, d, J=1.7 Hz), 4.96 (1H, d, J=1.7 Hz), 4.43 (1H, m), 4.30 (1H, d, J=8.9 Hz), 4.19 (1H, d, J=8.9 Hz), 3.80 (1H, d, J=7.2 Hz), 3.48 (1H, m), 3.13 (1H, m), 3.08 (1H, m), 2.60~1.30 (14H, m), 2.44 (3H, s), 2.21 (3H, s), 1.93 (3H, s), 1.66 (3H, s), 1.22 (3H, s), 1.12 (3H, s); $\delta_C$ 203.7, 172.4, 171.2, 169.7, 168.0, 167.0, 166.9, 142.7, 136.9, 133.6, 132.7, 132.0, 130.1, 129.1, 129.0, 128.7, 128.4, 127.0, 126.4, 84.4, 80.9, 79.1, 76.3, 75.5, 75.0, 73.8, 72.0, 71.7, 58.4, 56.1, 52.7, 45.5, 43.1, 40.1, 38.4, 35.5, 34.4, 34.4, 33.4, 28.4, 28.4, 26.7, 24.4, 22.6, 22.0, 20.8, 14.8, 9.5. HRFABMS m/z 1064.3521 [M+Na$^+$] (calcd for $C_{55}H_{63}NO_{15}S_2Na$, 1064.3537.

Example 15.1

Synthesis of M1 Compound of Substituent 15 (70 in this Example)

Scheme 15.1

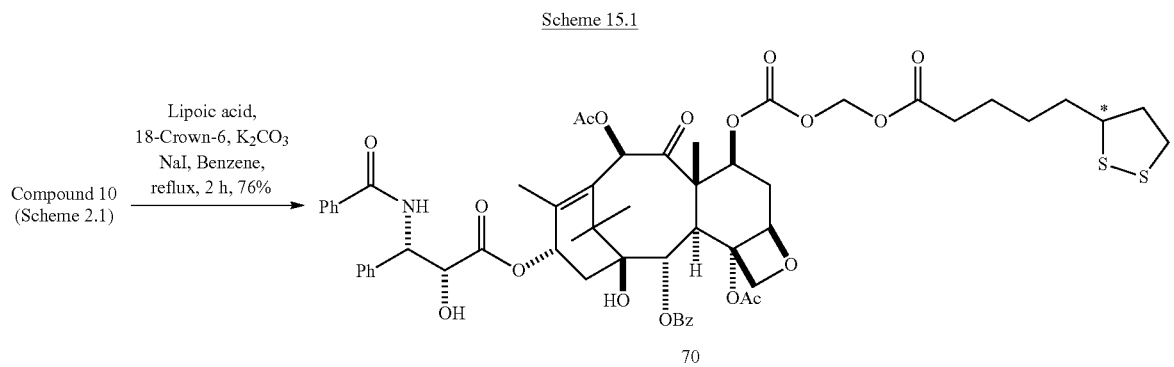

Synthesis of compound 70. A dry 25 mL round bottom flask was charged with a magnetic stirring bar, compound 10 (Scheme 2.1, 40 mg, 42.3 μmol) and sodium iodide (9.5 mg, 63.5 mol). Acetone (2 mL) was added via syringe to dissolve the solid. The flask was then equipped with a water condenser and the reaction mixture was allowed to reflux (~62° C., oil bath) for 10 h. The resulting yellow solution was concentrated by rotary evaporation (35° C.) to give a yellow residue. To the flask was added lipoic acid (17.0 mg, 82.6 μmol) and benzene (2 mL). After $K_2CO_3$ (17.5 mg, 126.9 μmol) and 18-crown-6 (67.1 mg, 253.8 μmol) was added, the flask was capped with a water condenser, warmed up to 65° C. and stirred for 3.5 h. TLC was used to examine the reaction progress. Decomposed product could be detected with prolonged reaction time. The reaction solution was allowed to cool down to room temperature and diluted with ethyl acetate (75 mL), washed with saturated aqueous sodium bicarbonate (2×4 mL), water (2×4 mL) and brine (2×4 mL) and dried with anhydrous $Na_2SO_4$. Rotary evaporation (35° C.) gave a slightly yellow oily residue, which was purified by preparative TLC (developed with hexane:ethyl acetate=1:1) to yield 70 (36 mg, 32.2 μmol, 76%) as a white powder. Unreacted 10 (8 mg) was recovered.

$^1$H NMR (CDCl$_3$) δ 8.10 (2H, dd, J=7.5, 1.5 Hz), 7.76 (2H, d, J=7.0, 1.5 Hz), 7.62 (1H, m), 7.47-7.52 (5H, m), 7.33-7.43 (4H, m), 7.04 (1H, d, J=9.0 Hz), 6.30 (1H, s), 6.18 (1H, dd, J=8.0, 8.0 Hz), 5.90 (1H, d, J=6.0 Hz), 5.79 (1H, dd, J=9.0, 2.0 Hz), 5.70 (1H, d, J=6.0 Hz), 5.66 (1H, d, J=7.0 Hz), 5.48 (1H, dd, J=10.0, 7.0 Hz), 4.94 (1H, d, J=8.0 Hz), 4.79 (1H, d, J=2.5 Hz), 4.31 (1H, d, J=8.5 Hz), 4.17 (1H, d, J=8.5 Hz), 3.91 (1H, d, J=7.5 Hz), 3.56 (2H, m), 3.08-3.18 (2H, m), 2.62 (1H, m), 2.45 (1H, m), 2.38 (3H, s), 2.31 (2H, dd, J=9.0, 4.0 Hz), 2.15 (3H, s), 1.96 (1H, m), 1.89 (1H, m), 1.84 (3H, s), 1.80 (3H, s), 1.67 (6H, m), 1.46 (2H, m), 1.21 (3H, s), 1.18 (3H, s).

Example 17.1

Synthesis of an M1 Type Compound of Substituent 20, 73 Below

Scheme 17.1

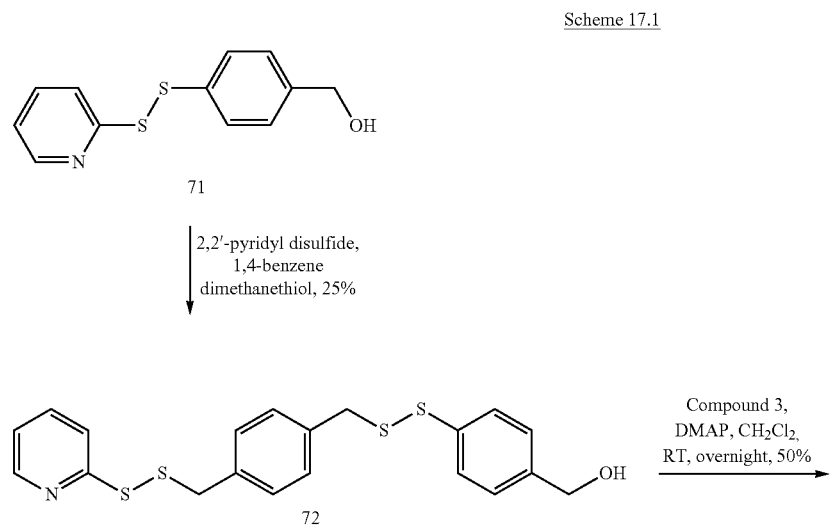

-continued

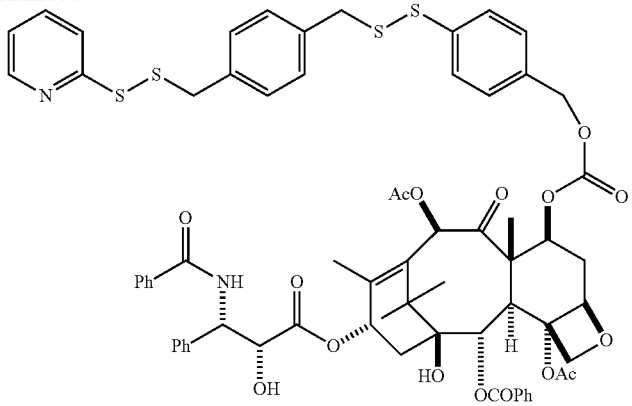

HF-pyridine, THF,   73 R = TBS
rt, overnight, 50%.   74 R = H

Synthesis of compound 72. To a deaerated (Ar) methanolic solution (1 mL) of compound 71 (96 mg, 385.6 μmol) was added a deaerated (Ar) methanolic solution (1 mL) of 1,4-benzenedimethanethiol (164 mg, 964 μmol) at 0° C. The reaction solution was maintained at 0° C. under Ar for 10 min, and then 2,2'-dipyridyl disulfide (466.7 mg, 2.12 mmol) was added. The reaction solution was maintained at 0° C. under Ar for 40 min. Workup as described above and purification by preparative TLC (30% EtOAc/hexanes) afforded compound 72 (Na, Y.; Wang, S.; Kohn, H. *J. Am. Chem. Soc.* 2002, 124, 4666-4677.) (40 mg, 25%): $^1$H NMR (CDCl$_3$) δ 8.38 (1H, d, J=4.8 Hz), 7.52 (1H, ddd, J=8.2, 7.2, 2 Hz), 7.49 (1H, d, J=7.2 Hz), 7.34 (2H, d, J=8.0 Hz), 7.24 (2H, d, J=8.0 Hz), 7.16 (2H, d, J=8.0 Hz), 7.12 (2H, d, J=8.0 Hz), 7.01 (1H, dd, J=8.2, 4.8 Hz), 4.64 (2H, s), 3.92 (2H, s), 3.84 (2H, s); $^{13}$C NMR (CDCl$_3$) δ 159.8, 149.4, 139.9, 136.9, 136.0, 135.8, 129.5 (×3), 127.8, 127.5, 120.6, 119.5, 64.6, 43.1, 43.0.

Synthesis of compound 73. To a solution of compound 72 (12 mg, 28.8 μmol) in dry dichloromethane (1 mL) was added to the stirred solution of bis(4-nitrophenyl) carbonate (13.1 mg, 43.2 μmol) and 4-(dimethylamino) pyridine (10.5 mg, 6.4 μmol) in dry dichloromethane (1 mL). The mixture was stirred at room temperature for 12 h. Then paclitaxel (49.1 mg, 57.6 μmol) was added, and the mixture was stirred at room temperature for another 12 h. Workup as described above and purification by column chromatography (30% EtOAc/hexanes) afforded compound 73 (Fardis, M.; Pyun, H.-J.; Tario, J.; Jin, H.; Kim, C. U.; Ruckman, J.; Lin, Y.; Green, L.; Hicke, B. *Bioorg. Med. Chem.* 2003, 11, 5051-5058; Liu, C.; Schilling, J. K.; Ravindra, R.; Bane, S.; Kingston, D. G. I. *Bioorg. Med. Chem.* 2004, 12, 6147-6161.) (30 mg, 80%): $^1$H NMR (CDCl$_3$) δ 8.42 (1H, d, J=4.6 Hz), 8.14 (2H, d, J. 8.5 Hz), 7.72 (2H, d, J=8.5 Hz), 7.61 (111, dd, J=7.6, 7.3 Hz), 7.25-7.55 (16H, m), 7.20 (2H, d, J=8.1 Hz), 7.14 (2H, d, J=8.1 Hz), 7.02 (1H, br dd, J=5.1, 3.3 Hz,), 6.92 (1H, d, J=9.2 Hz), 6.30 (2H, br s), 5.99 (1H, dd, J=9.2, 2.8 Hz), 5.70 (1H, d, J=7.1 Hz), 5.45 (1H, d, J=2.8 Hz), 5.15 (1H, d, J=12.2 Hz), 5.10 (1H, d, J=12.2 Hz), 4.98 (1H, br d, J=9.4 Hz), 4.45 (1H, m), 4.32 (1H, d, J=8.5 Hz), 4.21 (1H, d, J=8.5 Hz), 3.96 (2H, s), 3.87 (2H, s), 3.82 (1H, d, J=7.1 Hz), 2.57 (1H, m), 2.47 (3H, s), 2.40 (1H, dd, J=15.4, 9.4 Hz), 2.23 (3H, s), 2.19 (1H, dd, J=15.4, 8.7 Hz), 1.94 (3H, s), 1.89 (1H, m), 1.69 (3H, s), 1.25 (3H, s), 1.14 (3H, s); $^{13}$C NMR (CDCl$_3$) δ 203.8, 171.3, 169.9, 167.8, 167.1, 167.1, 159.9, 154.1, 149.5, 142.7, 138.1, 136.8, 136.7, 136.1, 135.8, 133.7, 133.5, 132.9, 132.8, 132.1, 130.3, 129.6, 129.5, 129.2, 129.1, 129.1, 128.8, 128.7, 128.5, 127.5, 127.2, 126.6, 120.6, 119.6, 84.5, 81.1 79.2, 76.9, 76.5, 75.6, 75.1, 72.2, 72.1, 70.2, 58.5, 52.7, 45.6, 43.2 (×2), 43.1, 35.6, 35.5, 26.8, 22.7, 22.2, 20.9, 14.8, 9.6; HRFABMS m/z 1297.3513 [M+H$^+$] (calcd for C$_{68}$H$_{69}$N$_2$O$_{16}$S$_4$, 1297.3530).

Compound 73. To a solution of compounds 3 (32 mg, 28.3 μmol) and 72 (24 mg, 57.6 mop in dry dichloromethane (2 mL) was added 4-(dimethylamino) pyridine (10 mg, 82 μmol), and the mixture was stirred at room temperature for 12 h. Workup as described above and purification by column chromatography (30% EtOAc/hexanes) afforded compound 73 (20 mg, 50%): $^1$H NMR (CDCl$_3$) δ 8.44 (1H, d, J=4.7 Hz), 8.13 (2H, d, J=8.5 Hz), 7.75 (2H, d, J=8.5 Hz), 7.62 (1H, dd, J=7.6, 7.3 Hz), 7.25-7.55 (xxH, m), 7.20 (2H, d, J=8.5 Hz), 7.13 (2H, d, J=8.5 Hz), 7.09 (2H, d, J=8.5 Hz), 6.43 (1H, s), 6.28 (1H, dd, J=9.2, 8.1 Hz), 5.73 (1H, br d, J=8.5 Hz), 5.71 (1H, d, J=6.9 Hz), 5.56 (1H, dd, J=11.0, 7.1), 5.18 (1H, d, J=12.1 Hz), 5.15 (1H, d, J=12.1 Hz), 4.98 (1H, d, J=8.0 Hz), 4.68 (1H, dd, J=2.1 Hz), 4.35 (1H, d, J=8.5 Hz), 4.21 (1H, d, J=8.5 Hz), 3.99, (2H, s), 3.98 (1H, d, J=6.9 Hz), 3.84, (2H, s), 2.60 (1H, m), 2.59 (3H, s), 2.40 (1H, dd, J=15.1, 9.4 Hz), 2.18 (3H, s), 2.15 (1H, m), 2.02 (3H, s), 2.00 (1H, m), 1.82 (3H, s), 1.23 (3H, s), 1.18 (3H, s), 0.81 (9H, s), −0.02 (3H, s), −0.30 (3H, s); $^{13}$C NMR (CDCl$_3$) δ 201.6, 171.4, 169.9, 169.0, 167.0, 166.9, 159.0, 154.1, 149.0, 141.0, 138.2, 134.2, 134.0, 133.7, 132.7, 131.8, 130.2, 129.6, 129.3, 129.0, 128.7, 128.7, 128.0, 127.7, 127.3, 127.0, 126.4, 120.6, 120.0, 83.9, 80.9, 78.6, 76.4, 75.5, 75.3, 75.1, 74.4, 71.3, 69.5, 56.0, 55.6, 46.8, 43.5, 43.3, 42.7, 35.5, 33.4, 26.4, 25.5, 23.0, 21.5, 20.8, 18.1, 14.6, 10.7, −5.2, −5.8; HRFABMS m/z 1411.4497 [M+H$^+$] (calcd for C$_{74}$H$_{83}$N$_2$O$_{16}$S$_4$Si, 1411.4395).

To a solution of compound 73 (17.4 mg, 12.3 μmol) in 1 mL of anhydrous THE was added 0.1 mL of anhydrous pyridine, then the solution was cooled to 0° C. and 0.2 mL of HF-pyridine was added. The reaction mixture was allowed to warm to RT and stirred for 6 h. Workup as described above and purification by preparative TLC (50% EtOAc/hexane) gave 74 (14.4 mg, 90%): $^1$H NMR (CDCl$_3$) δ 8.41 (1H, d, J=4.7 Hz), 8.12 (2H, d, J=8.3 Hz), 7.77 (2H, d, J=8.6 Hz), 7.62 (1H, dd, J=7.6, 7.3 Hz), 7.25-7.55 (16H, m), 7.21 (2H, d, J=8.0 Hz), 7.14 (2H, d, J=8.0 Hz), 7.05 (1H, d, J=8.6 Hz), 7.03 (1H, br dd, J=5.1, 3.3 Hz), 6.38 (1H, s), 6.20 (1H, t, J=8.6 Hz), 5.81 (1H, dd, J=8.6, 2.2 Hz), 5.68 (1H, d, J=6.9 Hz), 5.50 (1H, dd, J=10.8, 7.2 Hz), 5.19 (1H, d, J=12.1 Hz), 5.14 (1H, d, J=12.1 Hz), 4.95 (1H, d, J=9.4 Hz), 4.82 (1H, dd, J=5.0, 2.2 Hz), 4.32 (1H, d, J=8.8 Hz), 4.19 (1H, d, J=8.8 Hz), 3.98, (2H, s), 3.94 (1H, d, J=6.9 Hz), 3.86, (2H, s), 3.69 (1H, d, J=5.0 Hz), 2.60 (1H, m), 2.39 (3H, s), 2.35 (2H, d, J=8.6 Hz), 2.19 (3H, s), 1.97 (1H, m, H-6), 1.88 (3H, s), 1.82 (3H, s), 1.23 (3H, s), 1.18 (3H, s); $^{13}$C NMR (CDCl$_3$) δ 201.5, 172.5, 170.4, 169.0, 166.9, 166.8, 159.0, 154.0, 149.2, 140.5, 138.0, 137.2, 137.0, 135.9, 135.8, 134.0, 133.8, 133.6, 133.0, 131.9, 130.1, 129.5, 129.5, 129.2, 129.0, 128.7, 128.7, 128.3, 127.6, 127.0, 127.0, 127.0, 120.6, 119.6, 83.8, 80.9, 78.5, 76.4, 75.5, 75.3, 74.2, 73.1, 72.2, 69.5, 56.2, 54.9, 47.0, 43.2, 43.2, 42.9, 35.5, 33.4, 26.5, 22.5, 20.9, 20.8, 14.6, 10.7; HRFABMS m/z 1297.3513 [M+H$^+$] (calcd for C$_{68}$H$_{69}$N$_2$O$_{16}$S$_4$, 1297.3530).

Example 17.3

Synthesis of an M3 Type Compound of Substituent 20, 76 Below compound 76 (Fardis, M.; Pyun, H.-J.; Tario, J.; Jin, H.; Kim, C. U.; Ruckman, J.; Lin, Y.; Green, L.; Hicke, B. *Bioorg. Med. Chem.* 2003, 11, 5051-5058; Liu, C.; Schilling, J. K.; Ravindra, R.; Bane, S.; Kingston, D. G. I. *Bioorg. Med. Chem.* 2004, 12, 6147-6161.) (30 mg, 80%): $^1$H NMR (CDCl$_3$) δ 8.42 (1H, d, J=4.6 Hz), 8.14 (2H, d, J=8.5 Hz), 7.72 (2H, d, J=8.5 Hz), 7.61 (1H, dd, J=7.6, 7.3 Hz), 7.25-7.55 (16H, m), 7.20 (2H, d, J=8.1 Hz), 7.14 (2H, d, J=8.1 Hz), 7.02 (1H, br dd, J=5.1, 3.3 Hz,), 6.92 (1H, d, J=9.2 Hz), 6.30 (2H, br s), 5.99 (1H, dd, J=9.2, 2.8 Hz), 5.70 (1H, d, J=7.1 Hz), 5.45 (1H, d, J=2.8 Hz), 5.15 (1H, d, J=12.2 Hz), 5.10 (1H, d, J=12.2 Hz), 4.98 (1H, br d, J=9.4 Hz), 4.45 (1H, m), 4.32 (1H, d, J=8.5 Hz), 4.21 (1H, d, J=8.5 Hz), 3.96 (2H, s), 3.87 (2H, s), 3.82 (1H, d, J=7.1 Hz), 2.57 (1H, m), 2.47 (3H, s), 2.40 (1H, dd, J=15.4, 9.4 Hz), 2.23 (3H, s), 2.19 (1H, dd, J=15.4, 8.7 Hz), 1.94 (3H, s), 1.89 (1H, m), 1.69 (3H, s), 1.25 (3H, s), 1.14 (3H, s); $^{13}$C NMR (CDCl$_3$) δ 203.8, 171.3, 169.9, 167.8, 167.1, 167.1, 159.9, 154.1, 149.5, 142.7, 138.1, 136.8, 136.7, 136.1, 135.8, 133.7, 133.5, 132.9, 132.8, 132.1, 130.3, 129.6, 129.5, 129.2, 129.1, 129.1, 128.8, 128.7, 128.5, 127.5, 127.2, 126.6, 120.6, 119.6, 84.5, 81.1 79.2, 76.9, 76.5, 75.6, 75.1, 72.2, 72.1, 70.2, 58.5, 52.7, 45.6, 43.2 (×2), 43.1, 35.6, 35.5, 26.8, 22.7, 22.2, 20.9, 14.8, 9.6; HRFABMS m/z 1297.3513 [M+H$^+$] (calcd for C$_{68}$H$_{69}$N$_2$O$_{16}$S$_4$, 1297.3530).

Example 18

Proposed Mechanisms of Paclitaxel Release

The mechanisms of paclitaxel release from analogs II and IV are likely to be similar, so the representative mechanism

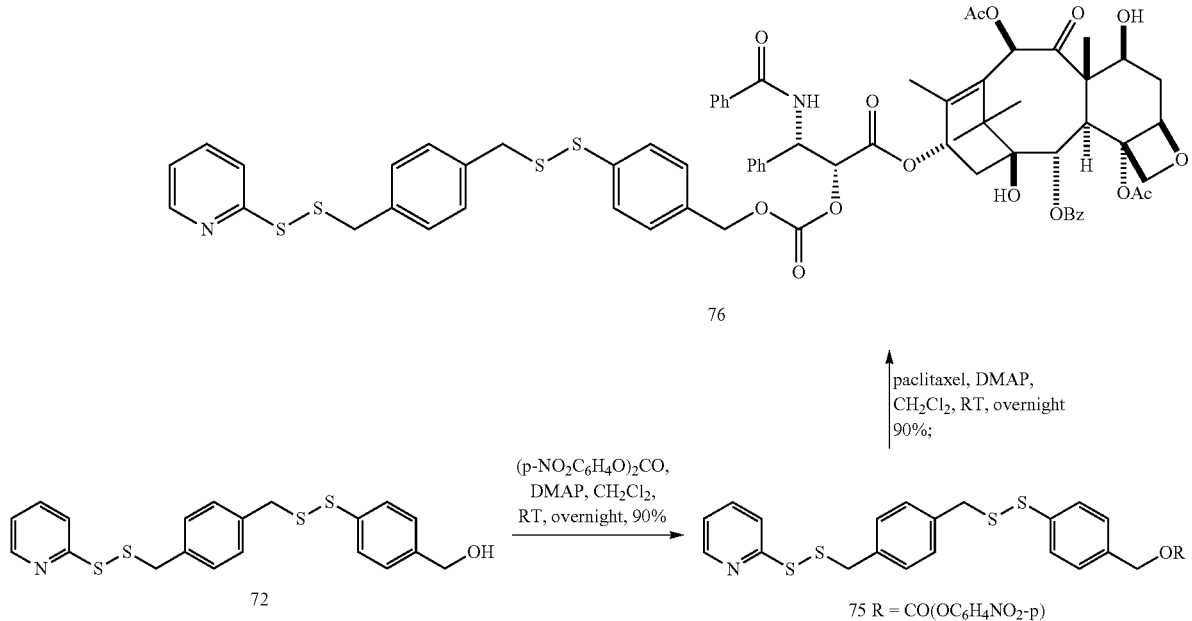

Scheme 17.3

To a solution of compound 72 (12 mg, 28.8 μmol) in dry dichloromethane (1 mL) was added to the stirred solution of bis(4-nitrophenyl) carbonate (13.1 mg, 43.2 μmol) and 4-(dimethylamino) pyridine (10.5 mg, 6.4 μmol) in dry dichloromethane (1 mL). The mixture was stirred at room temperature for 12 h. Then paclitaxel (49.1 mg, 57.6 μmol) was added, and the mixture was stirred at room temperature for another 12 h. Workup as described above and purification by column chromatography (30% EtOAc/hexanes) afforded for analog II is provided (FIG. 5). Though not wishing to be bound by the following theory, it is assumed that a simple gold-thiol linkage is created when the precursors react with gold nanoparticles. In this case a complex such as 6-Au would be formed.

There are then two possible mechanisms for the release of active paclitaxel. The first, which is considered the most likely, is simple hydrolysis of the carbonate linkage. Paclitaxel with 2'-carbonate substituents have been shown to be cytotoxic, presumably due to enzymatic hydrolysis by esterases present in the plasma (Damen, E. W. P.; Nevalainen, T. J.; van den Bergh, T. J. M.; de Groot, F. M. H.; Scheeren, H. W. Synthesis of novel paclitaxel prodrugs designed for bioreductive activation in hypoxic tumor tissue. *Bioorg. & Med. Chem.* 2002, 10, 71-77). It is thus likely that 6-Au would undergo hydrolysis to paclitaxel (PTX) and 16, which would then spontaneously lose carbon dioxide to form 17.

A second pathway could occur in the event that the gold-sulfur bond was susceptible to reductive cleavage. In this case the thiol 18 would result, which would undergo self-immolation (arrows) to give PTX and the unstable thioquinone methide 19, which would react with a nucleophile (most probably water) to give the final product 20. Regardless of mechanism when bound to gold the hydrolytic conversion of these analogs to paclitaxel occurs at a significantly slower rate. The novel finding herein therefore is that binding the analog stabilizes that particle against hydrolytic conversion in plasma.

In the case of analog XIII (FIG. 6) the mechanism is almost certainly hydrolytic. The other hydrolysis products would be the gold-bound PEG acid 21, carbon dioxide, and formaldehyde. Although the latter is undesirable, the amounts would be very small, and probably negligible based on natural abundance levels of this compound. The MFL Occupational Health Center (see the Web site located at www.mflohc.mb.ca) states: "Formaldehyde is also produced in the body and is normally found in the blood. It has been estimated that the body produces 50 grams (1¾ ounces) of formaldehyde per day. The fact that the body metabolizes such large amounts of formaldehyde suggests that formaldehyde is not a poison to the internal organs." Based on this evidence, the very small amounts of formaldehyde produced by hydrolysis will not be a health concern.

Example 19

Conversion of Thiolated Paclitaxel Analogs to Paclitaxel

Figure 7:
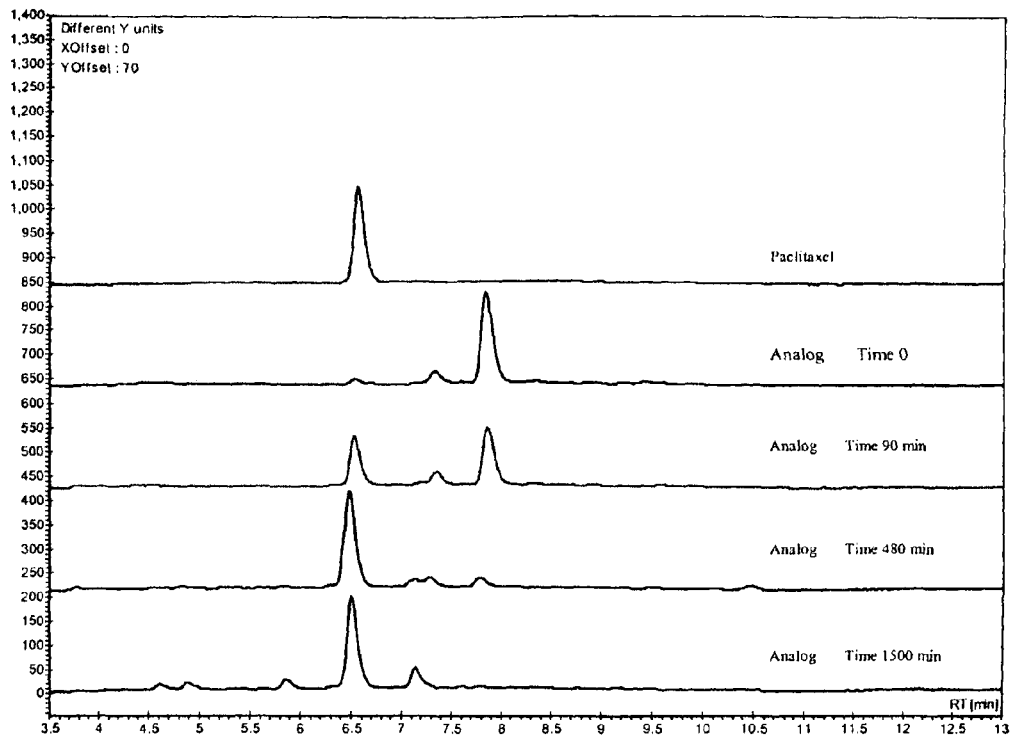
FIG. 7 provides data showing the time dependent hydrolytic conversion of analog XIII into paclitaxel. 1 mg of the thiolated paclitaxel analog XIII was diluted in 1 ml of a hydrolysis buffer (0.25 mg/mL NaHCO$_3$, 1 mg/ml dithiolthreitol, dissolved in a 59% MeOH/H$_2$O diluent). Samples were incubated at the indicated times and analyzed by RP-HPLC. The data show the time dependent hydrolysis of analog XIII into paclitaxel.

To monitor the conversion of analogs II, IV and XIII to paclitaxel a reverse phase high performance liquid chromatography (RP-HPLC) method was developed that clearly identifies both entities during the reaction. For these studies the inventors induced the full conversion of the analogs by incubating them in a buffer containing dithiolthreitol (DTT), to induce self-immolation, and $NaHCO_3$, to induce hydrolysis. The progressive conversion of the analog XIII to paclitaxel over time is shown in FIG. 7. These analyses illustrate that at the beginning of the experiment (T=0) only the analog is present. Then with continued incubation in the hydrolytic buffer the peak corresponding to the analog begins to decrease with a simultaneous appearance of a peak corresponding to paclitaxel. For analog XIII the conversion is complete by 4-6 hours. Similar patterns were observed for analogs II and IV.

Figure 8:
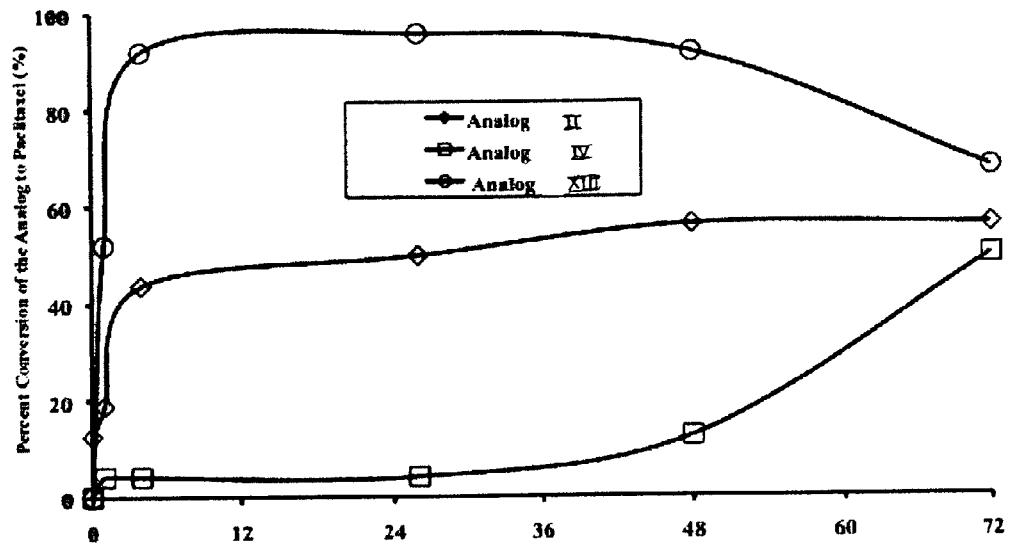
FIG. 8 provides differences in the in vitro hydrolytic conversion of the thiolated paclitaxel analogs II, IV and XIII in tissue culture media.

In the next series of studies the inventors monitored the conversion of the analogs to paclitaxel under more physiologic conditions. For these studies an aliquot of each analog was spiked into serum containing tissue culture media and samples were analyzed over a period of 72 hours. Shown in FIG. 8 are differences in the hydrolytic conversion of each analog to paclitaxel. For example it is apparent that analog XIII is most sensitive to hydrolytic cleavage since within 4 hours of incubation most of the analog is converted to paclitaxel. In contrast, only 50% of the total amount of analogs II and IV were converted to paclitaxel over the same 72-hour period, albeit the conversion occurred over a different timeframe. For analog II this hydrolysis occurred between 0 and 4 hours whereas the conversion of analog IV occurred between 48 and 72 hours.

Example 20

Characterization of the binding of Analogs II, IV, and XIII to Colloidal Gold Nanoparticles Having confirmed the ability of the analogs to form paclitaxel the inventors began optimizing the analogs' binding to the colloidal gold nanoparticles. The binding of the analogs to the colloidal gold nanoparticles was evaluated by determining the pH and saturation binding optima. For the pH-based studies the pH of various aliquots is adjusted from a base value of 4 to 10 using 1N NaOH. Subsequently, 50 µg of each analog was added to the gold aliquots. The samples were incubated for 20 minutes and followed by 10% v/v addition of a 150 mM NaCl solution. Typically the addition of the salt solution to "uncoated" gold particles causes their immediate precipitation: a phenomenon documented by a color change of the particles from red to black. Thus, the pH optimum is identified as the pH that allows the analogs to bind to the gold nanoparticles and prevent their precipitation by NaCl. Although all of the analogs bound between pH 6-10 all formulation work was conducted at pH 7 or below to avoid potential hydrolysis of the analogs at higher pH.

The second analysis defined the binding capacity of the particles for each analog. For these studies the pH of the colloidal gold nanoparticles was adjusted to the pH binding optimum for each analog, and then increasing amounts of each analog were added to a fixed volume of the pH-adjusted gold and incubated as described above. To separate bound and free analog the various preparations were centrifuged at 13600 rpm for 20 minutes. The resultant colloidal gold pellet, containing the bound analog, and supernatant, containing the unbound analog, were separated and analyzed for paclitaxel content. Prior to analysis each sample was incubated with the $NaHCO_3$/DTT buffer to induce the hydrolytic conversion of the analogs to paclitaxel. The samples were subsequently analyzed by a paclitaxel specific ELISA (Hawaii Biotech).

Figure 9:
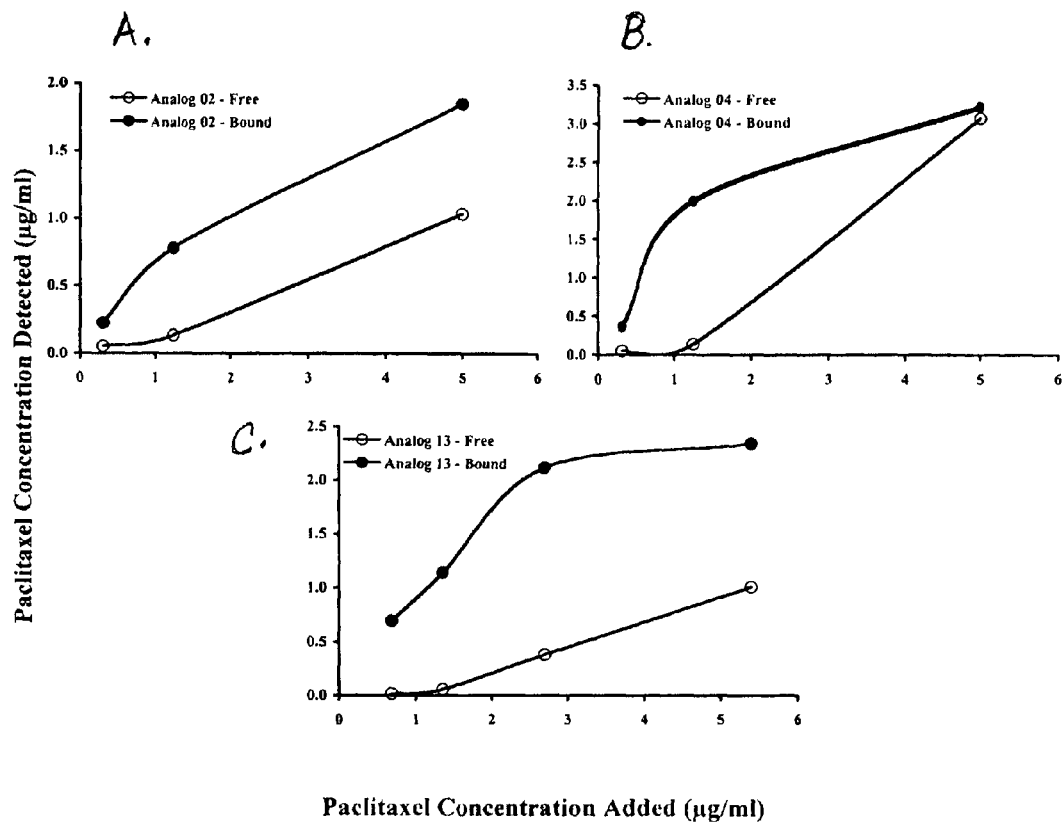
FIGS. 9A-C. Graphic representation of saturation binding of analogs II, IV and XIII on colloidal gold nanoparticles. A, analog II; B, analog IV; C, analog XIII.

The data shown in FIG. 9 are consistent with the binding characteristics of therapeutics to gold nanoparticles. Briefly, at relatively low concentrations all the added compounds bind to the available binding sites on the gold nanoparticles. As the analog concentrations are increased more analog is able to bind to the available binding sites on the gold particles, resulting in an increase in the amount of analog bound to the nanoparticles. At saturation all the binding sites are occupied; any additional analog will not bind and will be measured as "free". These data demonstrate that the particles possess a finite number of binding sites.

Example 21

Analog Formulations

The paclitaxel analogs, along with TNF and PEG-THIOL, were formulated into their respective formulations. The optimized formulation for each analog has been generated and designated as Formulation II for analog II, Formulation IV for analog IV and Formulation XIII for analog XIII.

One of the challenges in developing these formulations was to ensure the binding of all three constituents (i.e., the analog, TNF and PEG-THIOL) onto the gold particles. To optimize the interaction of all three moieties with the nanoparticles the inventors developed an apparatus (depicted schematically in FIG. 10) that vigorously mixes the colloidal gold nanoparticles with the three main components. The apparatus includes two large glass containers 10 and 20. Container 10 contains a solution of TNF, the paclitaxel analog and PEG-THIOL; and container 20 contains the colloidal gold particles. Once the two containers 10 and 20 are loaded with their respective solutions (i.e., pH adjusted gold sol or the TNF/analog/PEG-THIOL mixture) the solutions are physically drawn into T-connector 30 by a single peristaltic pump 40 at a flow rate of 1 L/min. In effect, this configuration enables the reduction of large volumes of reactants (e.g., 5 L for a bench scale preparation) into a small reaction volume (100 µl mixing chamber in T-connector 30). An in-line mixer (vortex) 50, placed immediately downstream of T-connector 30, ensures vigorous mixing of the colloidal gold particles with the TNF/paclitaxel/PEG-THIOL solutions as they exit T-connector 30. The resultant mixture is collected in a collection flask 60 and allowed to stir (e.g. on stir plate 70) for 15 minutes, and then HSA (5% v/v at 600 µg/ml in $DIH_2O$) is added to the solution. Once the mixing step is complete the colloidal gold bound reactants are concentrated and separated from free reactants by ultrafiltration through a 100 kD MW filter (not shown).

Figure 10:
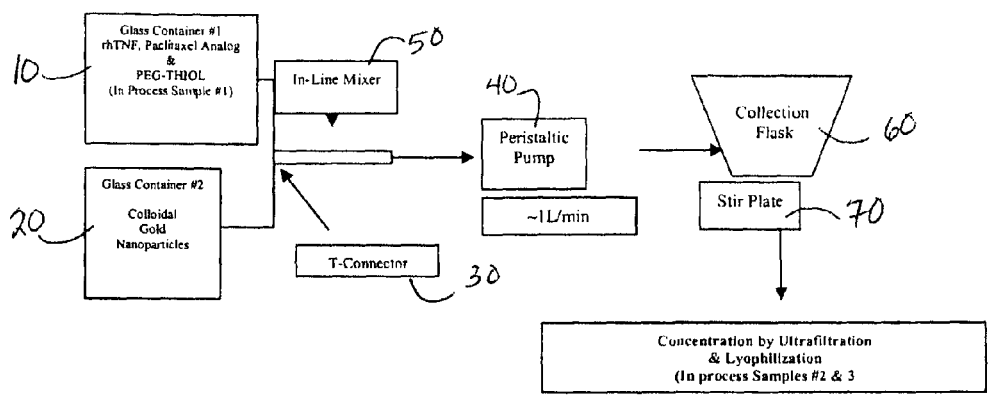
FIG. 10 provides a schematic for manufacturing of colloidal gold bound analogs.

To estimate the recoveries of both the analog and TNF throughout the manufacturing process, in-process samples were collected, as shown in FIG. 10, and analyzed for the respective analyte. For example, an initial sample is collected immediately after the working solutions are made in container 10. After binding and concentration, an aliquot of the permeate, which contains TNF and the analog and which are not bound to the particles, is collected. The retentate, which contains a concentrate of the colloidal gold nanoparticles bound with TNF and analog, is prepared for lyophilization. Upon lyophilization, samples are analyzed for TNF, analog, and hydrolyzed paclitaxel content by their respective method.

Example 22

In Vitro Characterization of Formulations II, IV and XIII a. Recovery of TNF and the Paclitaxel Analogs Throughout the Manufacturing Process.

The data presented in Table I tracks the recovery of the key components of the nanodrug formulations throughout the manufacturing process. In this Example, all formulations were manufactured with initial binding concentrations of 0.1, 2.5 and 15 µg/ml of TNF, paclitaxel analog and PEG-THIOL, respectively. The data presented below illustrate that a majority of the two active pharmaceutical ingredients used to manufacture the formulations are found in the final lyophilized product. The reactants completely bind to the particles since there are no detectable levels of the reactants in the permeate (i.e., the fluid that was removed during concentration.). Finally, minimal quantities of the reactants are released during lyophilization since negligible quantities are detected after centrifugation of the reconstituted final product.

TABLE I

Recovery of TNF and the paclitaxel analogs throughout the manufacturing of the CYT-20000 series of colloidal gold-based nanotherapies.

| In-Process Samples Analog Used in Formulation | TNF Recovery | | | Paclitaxel Recovery | | |
|---|---|---|---|---|---|---|
| | II | IV | XIII | II | IV | XIII |
| In Process Sample #1 (µg/ml) | 0.12 | 0.11 | 0.13 | 2.2 | 2.3 | 1.7 |
| In Process Sample #2 Unbound Material (µg/ml) Final Product Specifications | 0 | 0 | 0 | 0 | 0 | 0 |
| In Process Sample #3 Concentration (µg/ml) | 28 | 23 | 33 | 744 | 743 | 726 |
| Percent Free in Final Product (%) | 6.0 | 14.2 | 1.2 | 0.3 | 7.8 | 2.1 | b. Binding Thiolated Paclitaxel Analogs to Gold Alters the In Vitro Hydrolytic Profile of the Analogs The products described above were tested for their ability to undergo in vitro hydrolysis to generate paclitaxel. For these studies the lyophilized material was reconstituted with $DIH_2O$ and equal amounts of either the soluble analog or its gold bound variant were spiked into tissue culture media. The samples were subsequently treated and analyzed by RP-HPLC as described above.

The colloidal gold bound analogs exhibited a much slower rate of hydrolysis when compared to the soluble analog (FIG. 11). As described above, soluble analog XIII was completely converted to paclitaxel within 4 hours. Over the same time period only 5-8% of the total amount of Formulation XIII was converted to paclitaxel and by 72 hours the percentage only increase to 25% of available drug. The data for Formulation II and Formulation IV also showed a slower rate of conversion with only 20% and 2%, respectively, of each colloidal gold bound analog being converted to paclitaxel at 72 hours.

Though not wanting to be bound by the following theory, it is believed that two possibly related mechanisms may explain these results. First, the gold nanoparticle may slow the rate of hydrolysis of the analogs by preventing the self-immolation of the analog. Thus, the formation of the gold-sulfur bond may protect the sulfhydryls from oxidation and thus prevent the self-destructive pathway of hydrolysis. Second, the orientation of the analog on the particle surface may also prevent hydrolysis by preventing $H_2O$ from accessing the carbonate linkage. The latter possibility is interesting given that the formulations contains a hydrophilic polymer (PEG-THIOL) that, in its role to block RES uptake, serves to hydrate the nanoparticle drug by drawing twice its molecular weight in water to the particle surface.

c. Paclitaxel Bioassay

The manufactured final products were also analyzed for paclitaxel activity with an in vitro bioassay using the A2780 indicator cell line, a cell line that is not sensitive to TNF. Briefly, after manufacturing the formulations with the various analogs, increasing doses of paclitaxel, analog, or the respective formulations were incubated with 5000 A2780 cells growing in 96-well plates. The cells were incubated with the drugs for a period of 3 days and cell proliferation was determined colorimetrically.

Figure 12A:
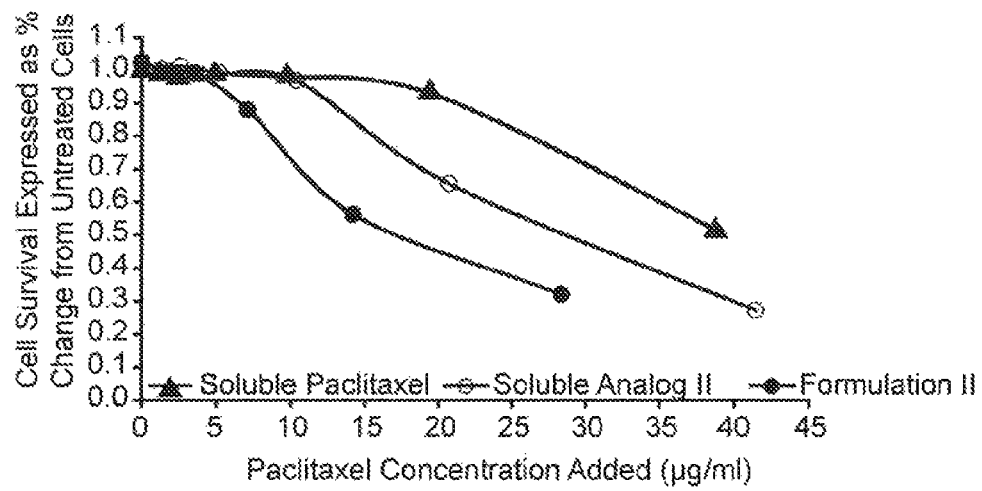
FIGS. 12A-C provide graphic representations showing the biologic activity of the unformulated and colloidal gold bound formulations of the paclitaxel analogs: comparison to paclitaxel. A, analog II; B, analog IV; C, analog XIII.
Figure 12B:
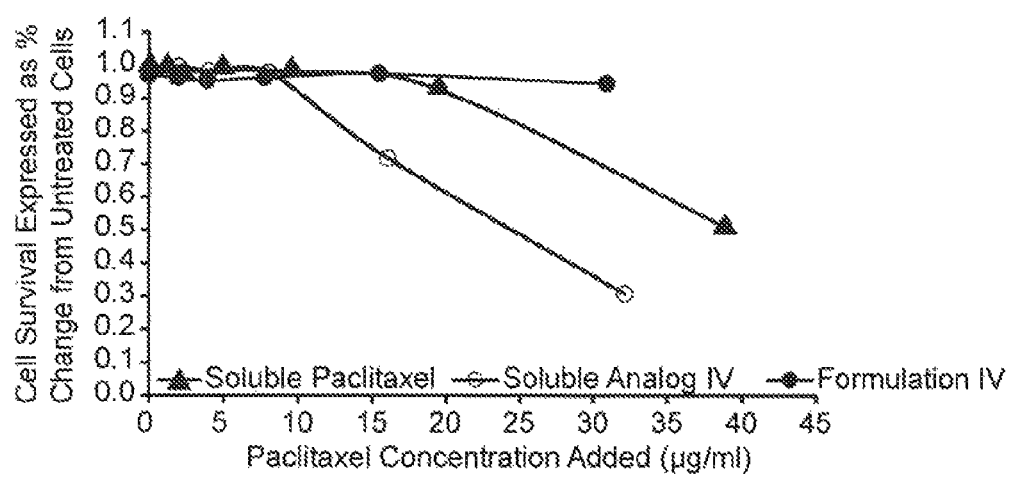
Figure 12C:
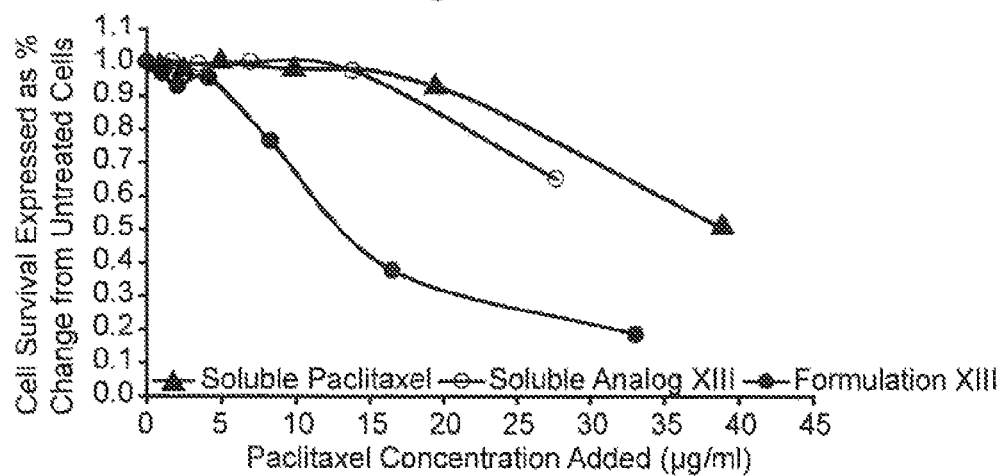
Figure 13A:
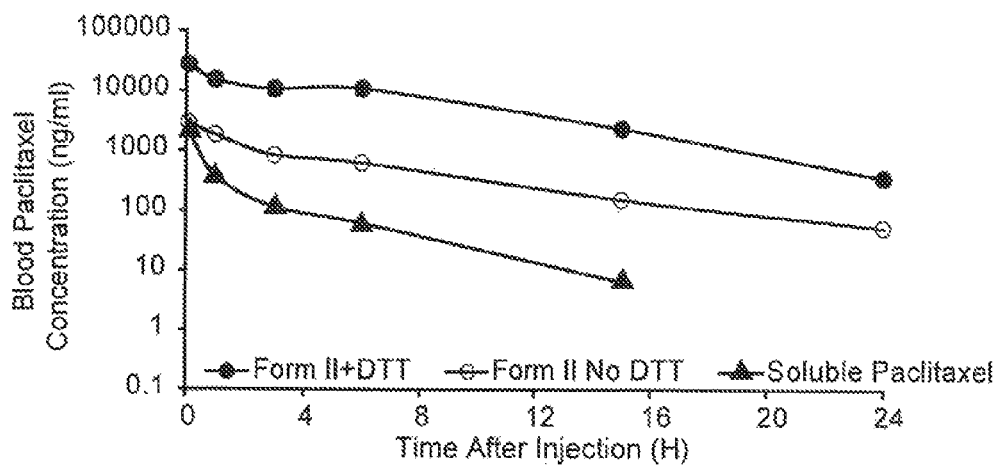
FIGS. 13A-C provide pharmacokinetic data of unformulated paclitaxel or the formulations of colloidal gold-based nanotherapies. Two representations for the nanodrugs are shown: "Form +DTT" denotes total paclitaxel in the blood while "Form No DTT" represents the fraction of the total analogs that was converted to paclitaxel in the blood. A, Formulation II; B, Formulation IV; C, Formulation XIII.
Figure 13B:
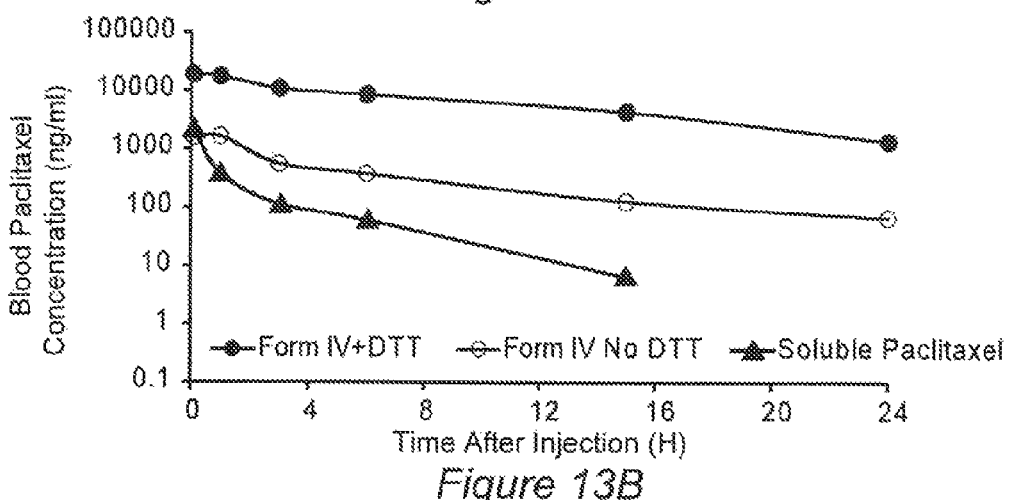
Figure 13C:
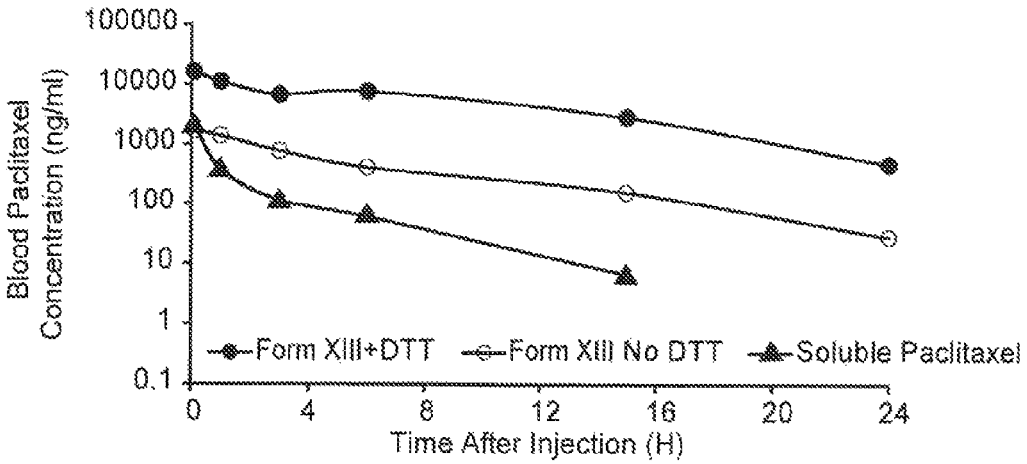

The data shown in FIGS. 12A-C indicate that binding the analogs to the colloidal gold nanoparticles results in analog specific in vitro biologic responses. For example, Formulation II and Formulation XIII exhibit significantly increased paclitaxel activity whereas Formulation IV, over the dose range tested, exhibits no apparent paclitaxel activity. The combination of increased potency with the differences in the rate of hydrolysis described above suggest that the gold bound formulations may act as slow release depots that generate paclitaxel over an extended period of time, accounting for the increased paclitaxel activity in vitro for Formulation II and Formulation XIII.

With respect to Formulation IV the data herein support the hypothesis that interaction of the analog with the gold surface strongly protects the analog from any interaction with the surrounding microenvironment. Nevertheless, the in vivo pharmacology data, described below, suggests that Formulation IV exhibits in vivo activity in tumor burdened mice.

Example 23

In Vivo Pharmacology a. Pharmacokinetic of the Analog Formulations in Tumor Burdened Mice The following studies were designed to compare the pharmacokinetics of the various formulations with either analog or paclitaxel. For these studies B16/F10 tumor burdened C57BL/6 mice (n=3/time point/formulation) were intravenously injected with either 50 μg of paclitaxel (dissolved in the Cremaphor EL diluent), the analog or equal doses of one of the three formulations (Formulation II, Formulation IV and formulation XIII). At selected time points after injection the mice were bled through the retro-orbital sinus. The blood was immediately diluted 1:1 with PBS containing 1 mg/ml heparin, frozen at $-20°$ C., and subsequently batch analyzed for paclitaxel concentration by ELISA.

Prior to analysis the samples were defrosted and divided into 2 equal aliquots. One aliquot was measured directly in the assay without any modification. This analysis provided a quantitative assessment of the percentage of the colloidal gold bound analogs undergoing hydrolysis in the blood. The second sample was treated with the hydrolysis buffer (DTT, $NaHCO_3$) to gauge the total amount of drug present in the blood.

As shown in FIGS. 14A-C, all three formulations significantly increased the half-life of paclitaxel, present as intact or hydrolyzed drug, in the circulation. For example, the amount of free paclitaxel (i.e., the amount that was hydrolyzed off the particle and present in the blood) present at 15 hours post injection was an average 20 times higher in animals receiving the formulations when compared to unformulated paclitaxel treatment. This difference was more dramatic when comparing the total amount of intact drug still remaining bound to the particle at this time. For example, blood levels in mice receiving Formulation II, Formulation IV and Formulation XIII were 360, 670 and 440 times higher at 15 hours when compared to unformulated paclitaxel treatment. Pharmacokinetic analysis of these data using the WinNonLin computer program reveals that over the 24-hour sampling time the nanodrugs increased overall exposure to paclitaxel, as measured by the area under the curve, by an average of 5-fold for the endogenously hydrolyzed fraction and 70-fold for the total drug.

Similar patterns were observed when comparing the pharmacokinetics of the colloidal gold-based drugs with the unformulated analogs (FIG. 14). Briefly, the CYT-20000 series possessed significantly longer half-lives when compared to unformulated analogs since blood levels 3 hours post injection were 10-50 times higher in the animals receiving the gold formulations. Moreover, these data demonstrate that binding the analogs to the colloidal gold nanoparticles prevents their hydrolysis in the circulation as these levels ranged between 5-10% of the total drug present in the circulation at any given time during the study.

These data also support the hypothesis that binding the analogs to the colloidal gold nanoparticles results in the generation of a depot that slowly releases paclitaxel over time. For example, comparing the pharmacokinetics of the hydrolyzed versus unhydrolyzed drugs reveals parallel profiles suggesting that a conversion of the analogs to paclitaxel occurs at some constant rate. Although this holds true for both the soluble and gold bound formulations the rate at which hydrolysis occurs is significantly slower for the gold bound preparations. Thus, the formulated nanodrugs act as slow release depots. Given the fact that the analogs do not hydrolyze on the surface of the particles indicates that they remain bound to the particles while in the circulation which in turn allows for the delivery to solid tumors (see below).

In addition to targeting the delivery of paclitaxel to solid tumors the formulations of the invention may also significantly reduce the known toxicities associated with paclitaxel administration. First, the well-known toxicities of the Cremaphor EL diluent are eliminated since the formulated nanodrugs are administered in a physiologic buffer. Furthermore, the ability of the analogs to remain bound to the particles also suggests that the formulated nanodrugs may also reduce the severity of a known dose limiting toxicity (neutropenia) of soluble paclitaxel.

b. Tumor Uptake Studies

Upon harvesting, the tumor samples described above were flash frozen and subsequently homogenized in PBS using a Polytron tissue disrupter. Debris was removed by allowing the homogenate to stand on ice for 20 minutes. The resultant supernatant was analyzed for paclitaxel concentration, by ELISA, and for total protein using a commercial protein assay (BioRad, Hercules, Calif., USA). Organ TNF concentrations were normalized to total protein. As with the PK studies, paclitaxel was measured.

Figure 15A:
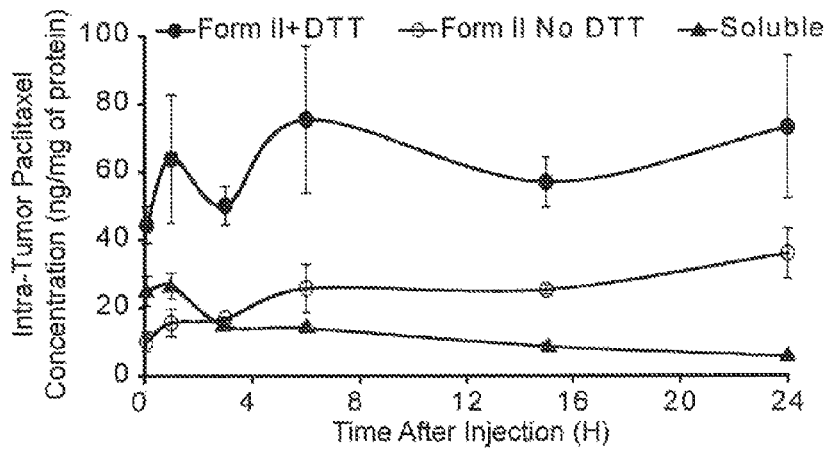
FIGS. 15A-C show graphic representation of uptake of either unformulated paclitaxel or the formulations by B16/F10 tumors. Both total and hydrolyzed fractions are reported for the formulations. A, Formulation II; B, Formulation IV; C, Formulation XIII.
Figure 15B:
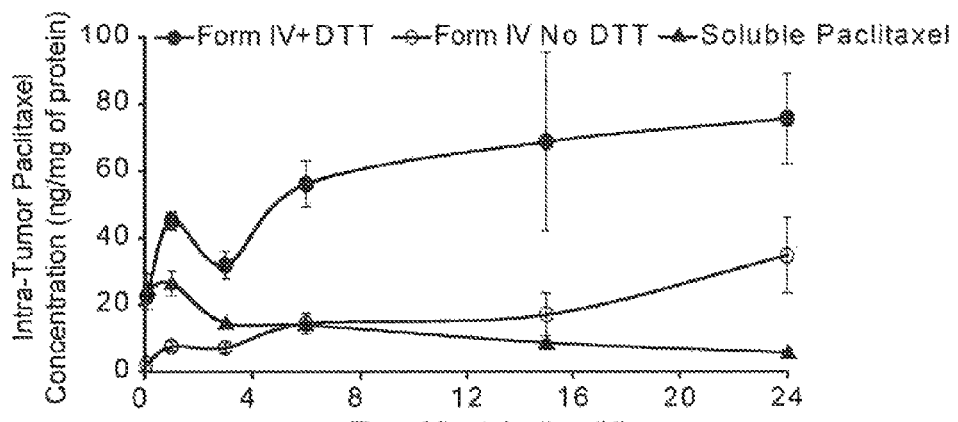
Figure 15C:
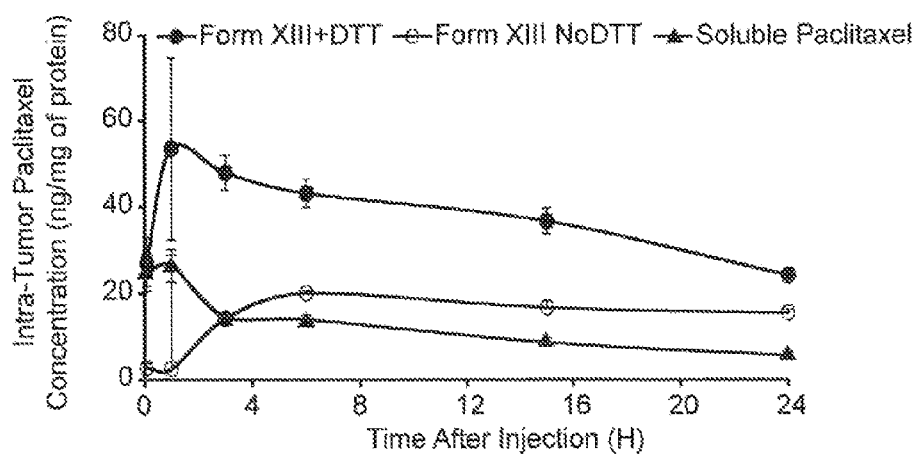

The data shown in FIGS. 15A-C demonstrates that all three gold-based formulations are able to deliver paclitaxel to B16/F10 solid tumors when compared to unformulated paclitaxel injection. This is supported by the data illustrating that while concentrations of paclitaxel in blood decreased over time, intra-tumor paclitaxel content, regardless of gold preparation, increased. This data shows that, in addition to targeting the delivery of paclitaxel to solid tumors, the formulations act as slow release depots upon "arrival" at the tumor. In addition the data presented herein further support this since it is observed that shortly after intravenous injection the formulations rapidly accumulate their respective analogs within the tumor. However, as shown in FIG. 15 there is an apparent lag time between the arrival of the gold bound analog and conversion to paclitaxel. For Formulation II and Formulation IV, the data reveal that the production of paclitaxel from the nanoparticle-based drugs increases over time, whereas for Formulation XIII, paclitaxel production increases from a baseline value and achieves a steady state over the remainder of the sampling time.

Formulation IV exhibited no biological activity in vitro. Nevertheless its ability to induce an anti-tumor response in vivo suggests that once bound to gold the analog acts as a pro-drug, in that it can release paclitaxel under certain conditions. In this prodrug form Formulation IV does not release paclitaxel in the circulation. Rather, by virtue of the tumor target delivery afforded by the gold nanoparticles, Formulation IV generates paclitaxel within the solid tumor.

Example 24

Role for TNF

Figure 16:
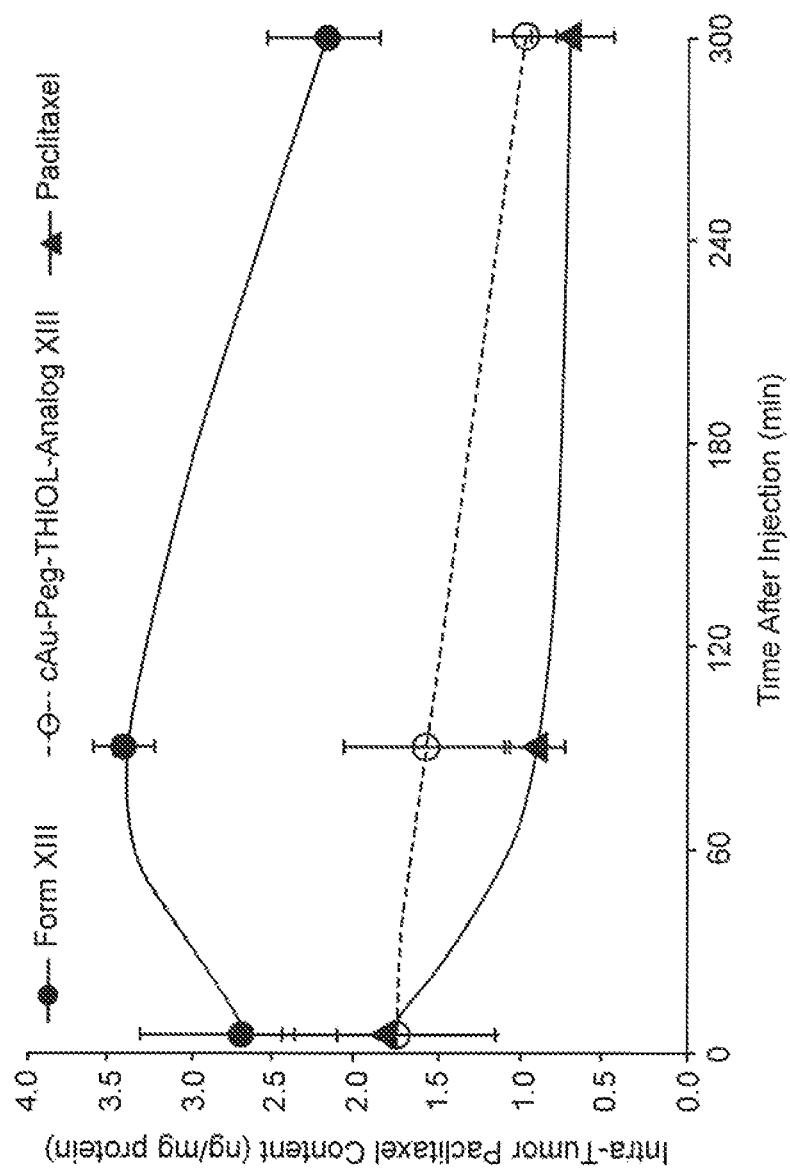
FIG. 16 provides graphic representation showing the effect of TNF on the intra-tumor accumulation of Formulation XIII, paclitaxel analog XIII, and paclitaxel. The lower intra-tumor levels of paclitaxel are solely due to the dose administered. For example, in FIG. 15 the dose of formulation administered corresponded to a paclitaxel dose of 50 µg whereas for the data in this figure, only 5 µg of paclitaxel were administered.

The data presented thus far have exclusively focused on the pharmacology of paclitaxel. The data clearly demonstrates that the formulated series of nanodrugs, which are made with TNF, a paclitaxel analog and PEG-THIOL, significantly alter the biology and pharmacology of not only paclitaxel but also the analog used to make the drug. Am initial hypothesis was that TNF acts as a tumor targeting ligand since preliminary data obtained with a control formulation (i.e., particles bound only with analog, with no TNF) delivered less paclitaxel to the B16/F10 tumors when compared to formulated nanodrugs (not shown). Indeed, the data shown in FIG. 16 further supports this hypothesis and shows that Formulation XIII, accumulates significantly more paclitaxel analog than either gold bound analog XIII (cAu-Peg-THIOL-Analog XIII) or unformulated paclitaxel.

In addition to its tumor targeting function, the inventors further propose that the TNF contained in the formulated nanodrugs also exhibits a therapeutic function. Data supporting this hypothesis comes from studies conducted a nanodrug comprised solely of TNF and PEG-THIOL bound to the surface of a gold nanoparticles surface. In these studies, (data not shown) the inventors observed that repeated injections of the nanodrug were not only safe, but also caused significant disruption of the tumor neovasculature that ultimately causes tumor regression and necrosis in tumor cells which themselves do not respond to the cytokine in vitro (i.e., TNF insensitive cancer cells).

Example 25

Efficacy Studies

Figure 17:
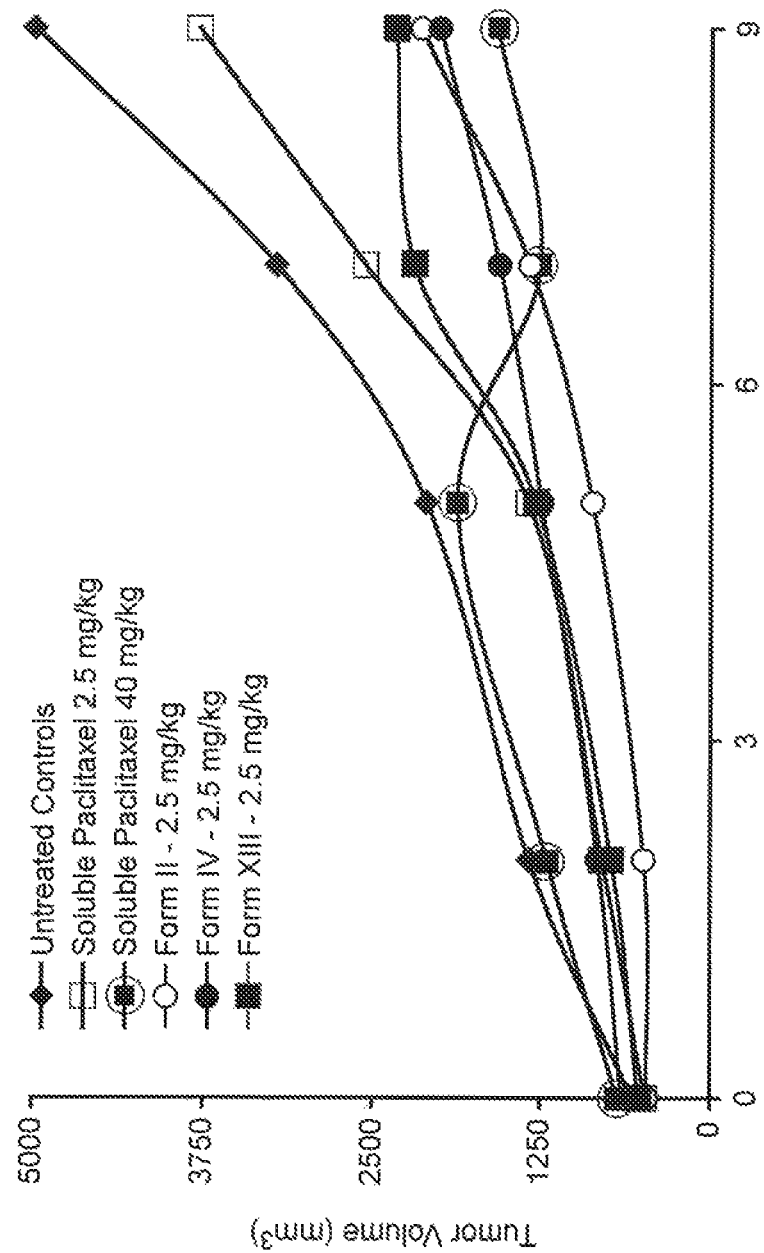
FIG. 17 provides graphic representation showing anti-tumor efficacy of either unformulated paclitaxel or Formulations II, IV and XIII.

The efficacy of the formulated nanodrugs was compared to that of unformulated paclitaxel for the treatment of tumor-burdened mice. For these studies C57BL/6 mice were implanted with B16/F10 melanoma cells. Once the cells formed tumors with an approximate volume of 500 mm³ the mice (n=4/group/formulation) received an injection of either unformulated paclitaxel or one of the formulations (Formulations II, IV and XIII). Paclitaxel was given at a dose of 40 mg/kg, whereas the formulated drugs were administered at a dose of 2.5 mg/kg. The mice were treated on day 0, 2, 5 and 7 of the days and tumor responses were determined by measuring tumor volume during the course of the study The data shown in FIG. 17 are consistent with the hypothesis that by targeting the delivery of paclitaxel to solid tumors the formulated nanodrugs induce a paclitaxel mediated anti-tumor response at a significantly lower dose of drug. For example, the formulated nanodrugs at a dose of 2.5 mg/kg were more effective than the same dose of unformulated paclitaxel. Based on these data, the formulated nanodrugs appear to be 16-fold more effective than paclitaxel since 2.5 mg/kg was as effective as 40 mg/kg of paclitaxel. This study was replicated 2 additional times with similar results.

Furthermore, although toxicological data were not collected in this study, the data also suggest that the nanodrugs may improve the safety of paclitaxel administration since: 1) A formulated nanodrug, as described herein, is a Cremaphor free preparation of paclitaxel and thus the known toxicities of the diluent are eliminated; and 2) in these studies, unformulated paclitaxel caused a 75% mortality rate whereas for Formulation IV, Formulation XIII and Formulation II the mortality rates were 0%, 0% and 25%, respectfully.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A compound of formula 1

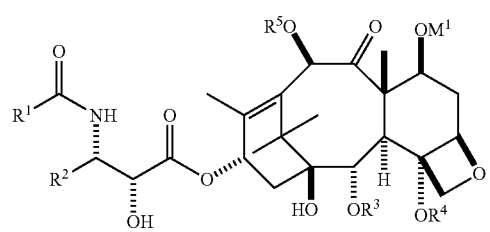

wherein
$R^1$ is phenyl, tert-butoxy, or $C_{1-6}$ alkyloxy;
$R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl;
$R^3$ is benzoyl, m-methoxybenzoyl, m-azidobenzoyl, or m-chlorobenzoyl;
$R^4$ is $C(O)R^x$ where $R^x$ is: H; $C_{1-6}$ alkyl, optionally substituted with one to six halogen atoms, which may be the same or different; $C_{3-6}$ cycloalkyl; or $C_{2-6}$ alkenyl or hydroxyl;
$R^5$ is H; or methyl; or $C(O)R^x$, where $R^x$ is: H, $C_{1-6}$ alkyl, optionally substituted with one to six halogen atoms, which may be the same or different; $C_{3-6}$ cycloalkyl; $C_{2-6}$ alkenyl or hydroxyl; and
M1 is sulfur bearing substituent linked to a colloidal metal particle, wherein the compound has a structure selected from the group consisting of structures 2-4, 6-11, 16-18, 27 and 33

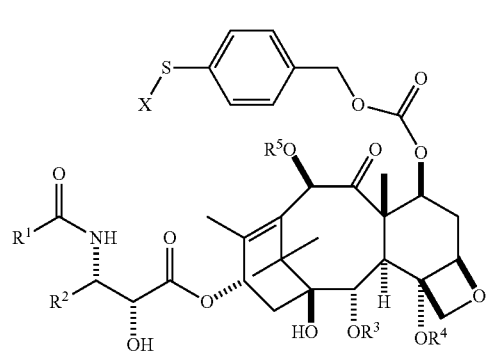

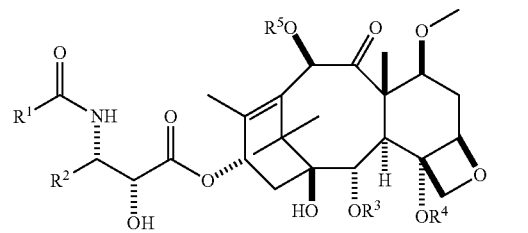

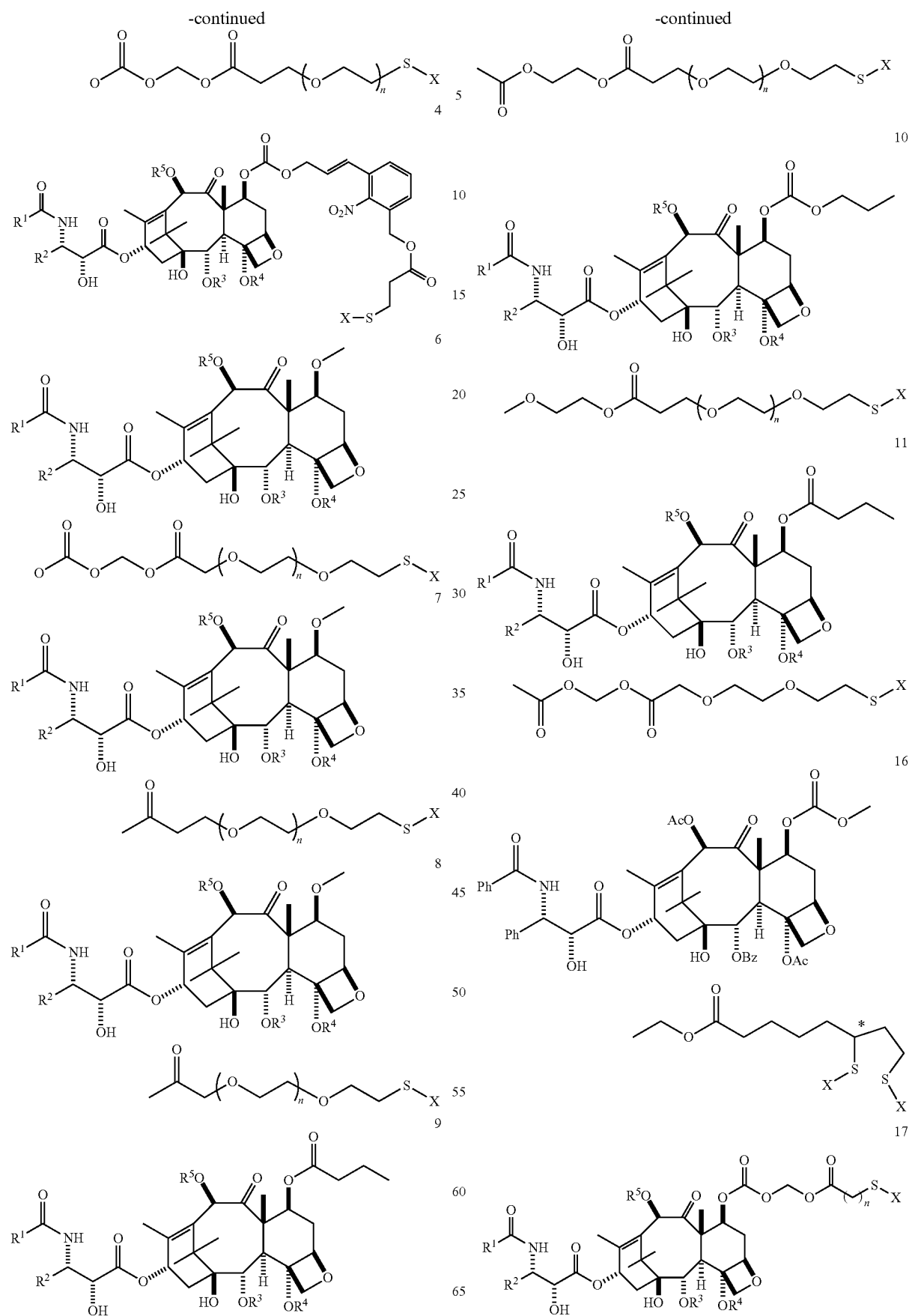

105
-continued

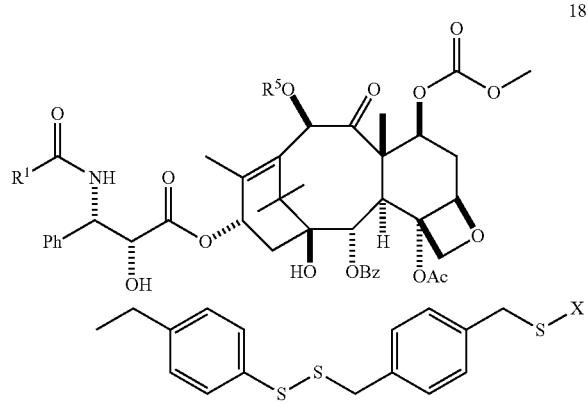

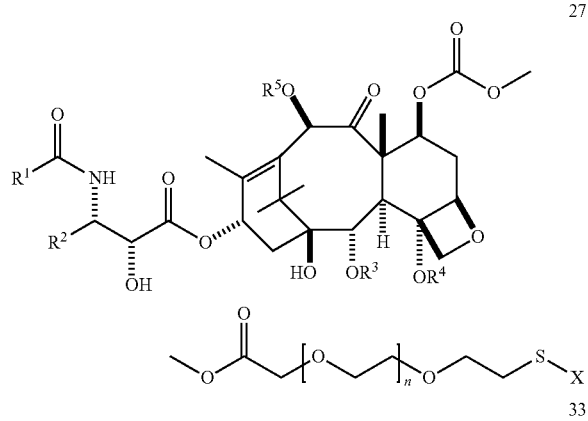

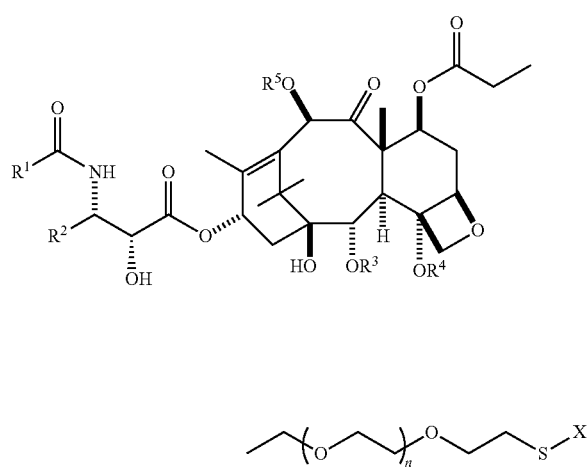

106
-continued

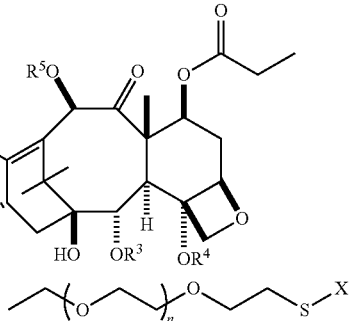

where n is an integer between 0 and 100, and X is said colloidal metal nanoparticle.

2. The compound as set forth in claim 1, wherein said colloidal metal nanoparticle contains gold.

3. A compound of formula 1

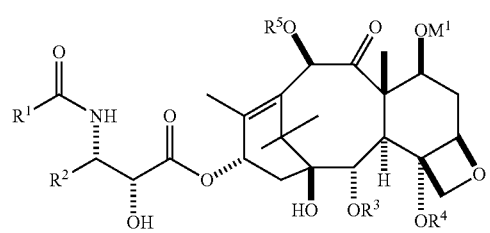

wherein
$R^1$ is phenyl, tert-butoxy, or $C_{1-6}$ alkyloxy;
$R^2$ is phenyl, 4-fluorophenyl, 4-methylphenyl, 2-furanyl, 2-thienyl, isopropyl, isobutenyl, cyclopropyl, 3-furanyl, 3-thienyl, or 2-propenyl;
$R^3$ is benzoyl, m-methoxybenzoyl, m-azidobenzoyl, or m-chlorobenzoyl;
$R^4$ is $C(O)R^x$ where $R^x$ is: H; $C_{1-6}$ alkyl, optionally substituted with one to six halogen atoms, which may be the same or different; $C_{3-6}$ cycloalkyl; or $C_{2-6}$ alkenyl or hydroxyl;
$R^5$ is H; or methyl; or $C(O)R^x$, where $R^x$ is: H, $C_{1-6}$ alkyl, optionally substituted with one to six halogen atoms, which may be the same or different; $C_{3-6}$ cycloalkyl; $C_{2-6}$ alkenyl or hydroxyl; and
M1 is a thiopyridyl or lipoic acid sulphur-bearing substituent.

4. The compound of claim 3, wherein the compound has a structure selected from the group consisting of structures 12-16, 20, 60, 64 and 70

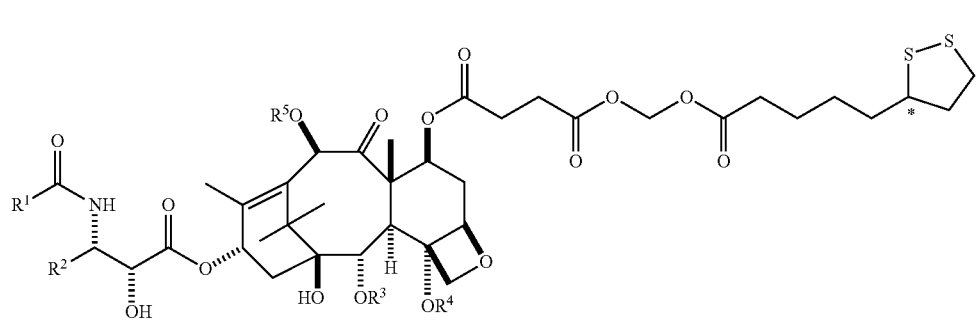

-continued
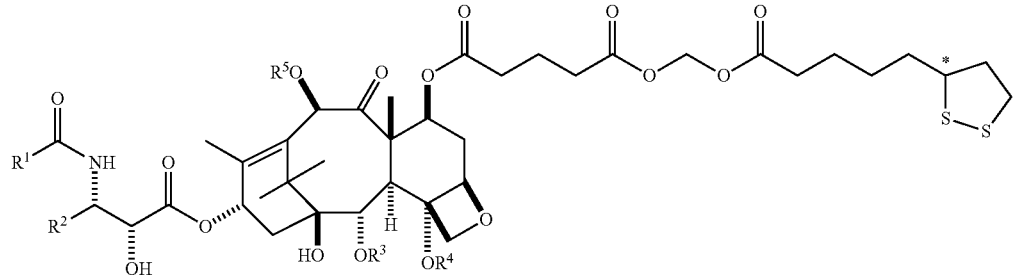
13
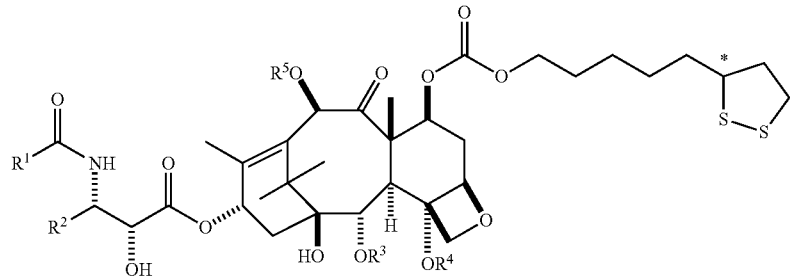
14
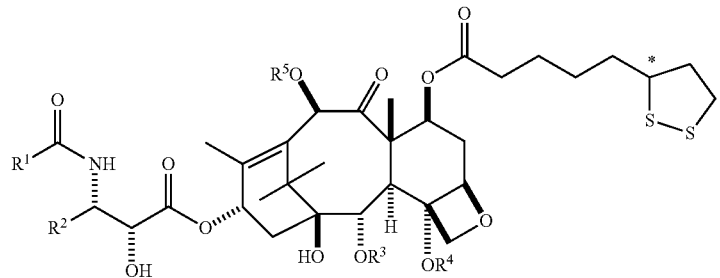
15
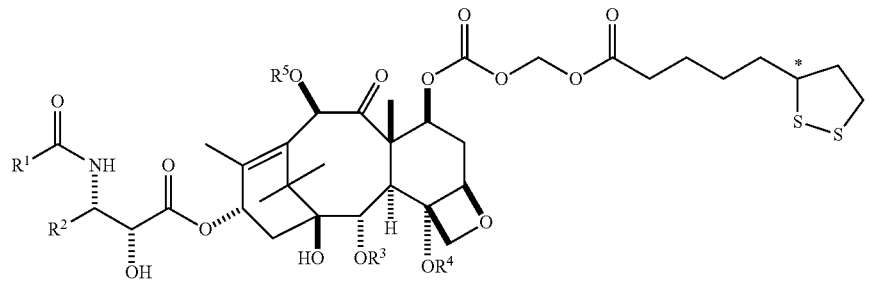
16
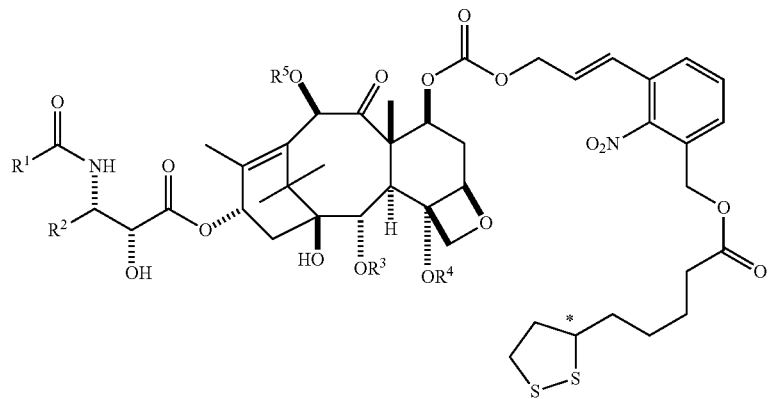
20

-continued
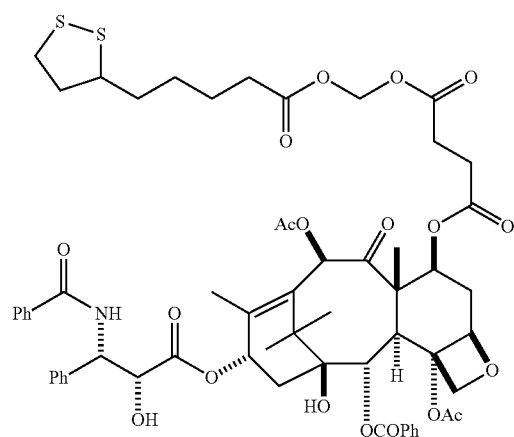
60
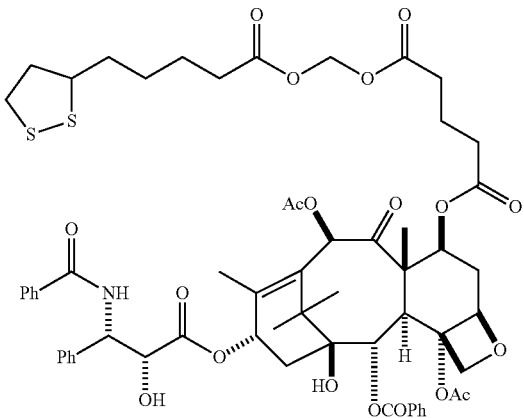
64
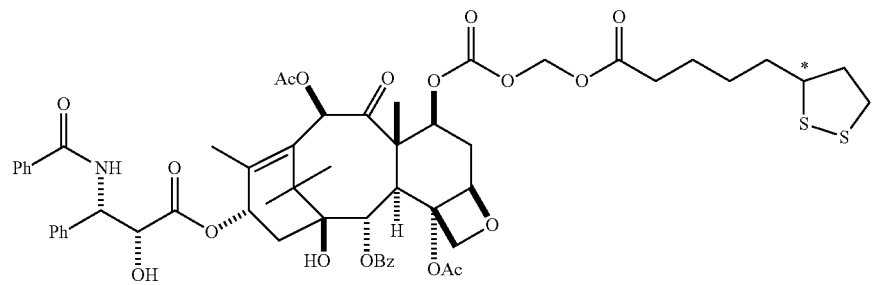
70
where * is a chiral center.
5. The compound of claim 3, wherein the compound has a structure selected from the group consisting of structures 19, 36, 6, 13, 5.1B, 28, 47, 74, 54 and 56
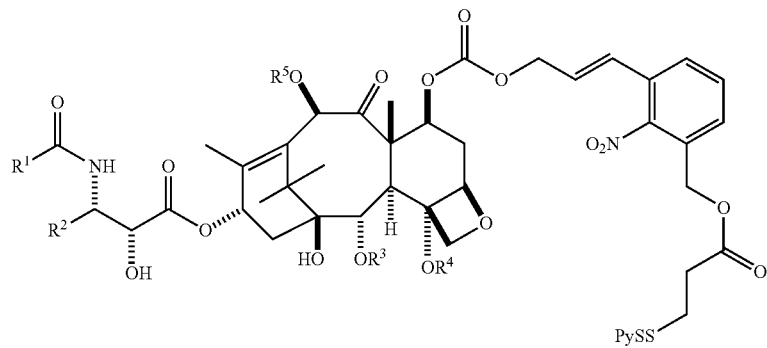
19
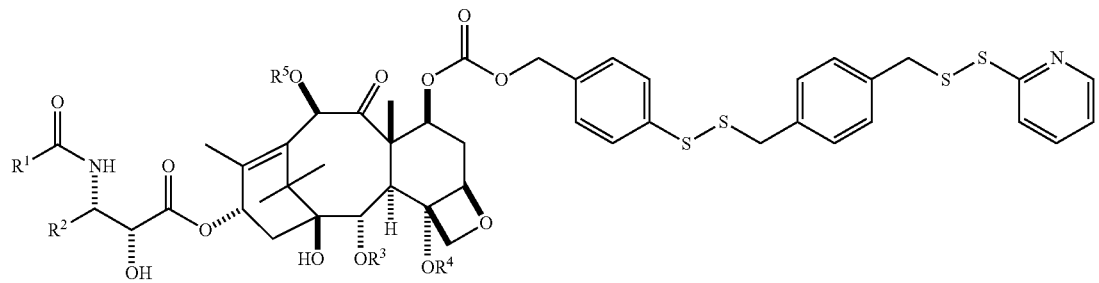
36

6
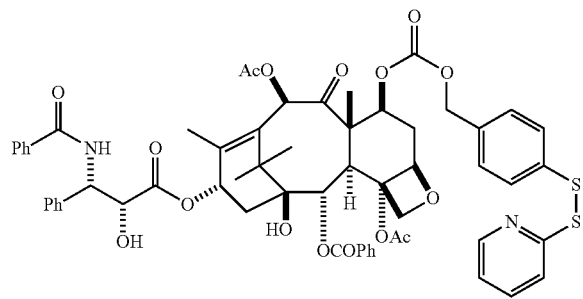
13
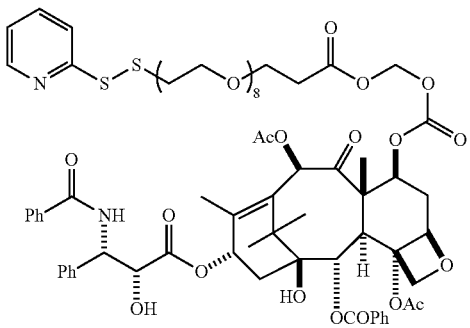
5.1B
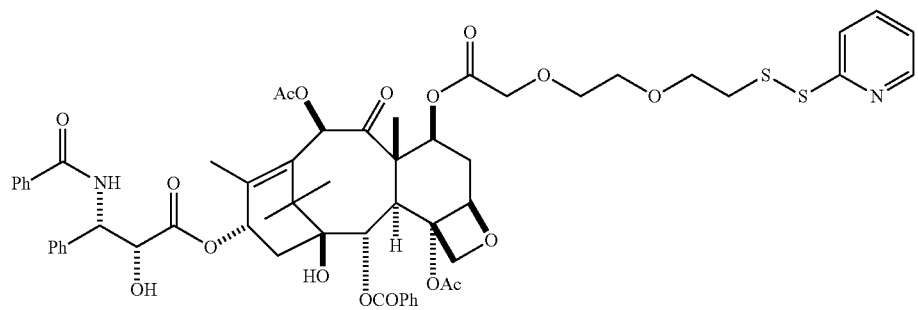
28
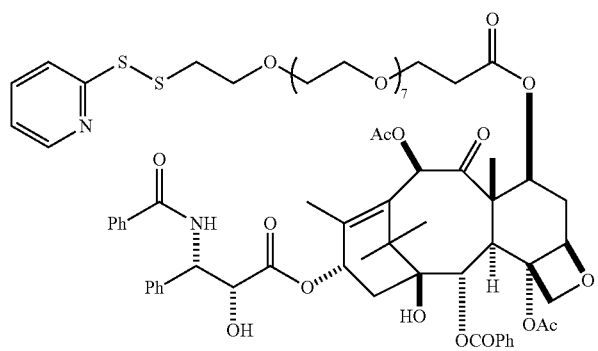
47
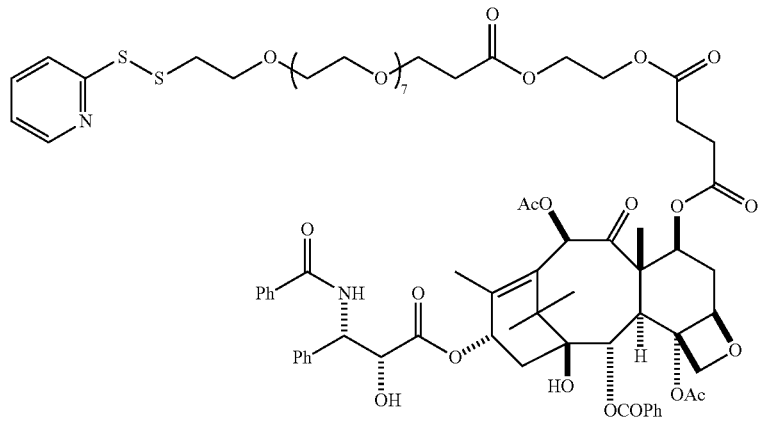

113                                                        114
-continued
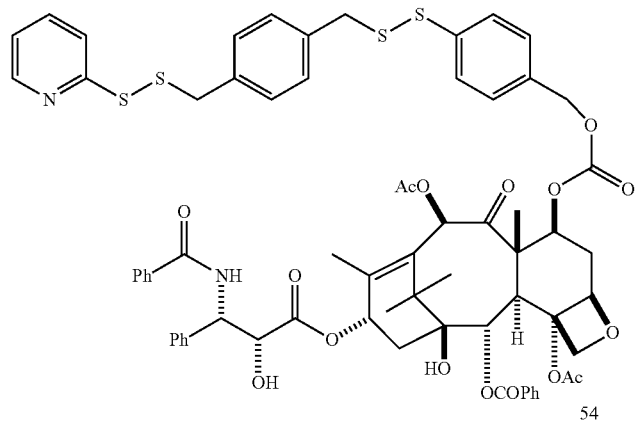
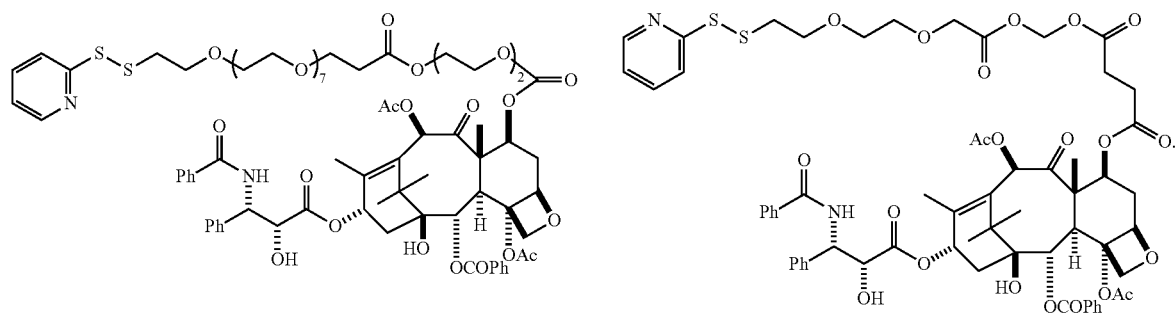
* * * * *